(12) United States Patent
Lamarque et al.

(10) Patent No.: US 10,597,409 B2
(45) Date of Patent: Mar. 24, 2020

(54) WATER-SOLUBLE TRIAZAPYRIDINOPHANE-BASED COMPLEXING AGENTS AND CORRESPONDING FLUORESCENT LANTHANIDE COMPLEXES

(71) Applicants: CISBIO BIOASSAYS, Codolet (FR); UNIVERSITE PAUL SABATIER, Toulouse (FR); CENTRE NATIONAL DE LA RECHERCHE SCIENTIFIQUE, Paris (FR)

(72) Inventors: Laurent Lamarque, Saint-Victor Lacoste (FR); Claude Picard, Auzeville-Tolosane (FR); Chantal Galaup, Rebigue (FR); Nadine Leygue, Ramonville Saint Agne (FR); Jurriaan Zwier, Rochefort du Gard (FR); Emmanuel Bourrier, Bagnols-sur-Ceze (FR)

(73) Assignees: CISBIO BIOASSAYS, Codolet (FR); UNIVERSITE PAUL SABATIER, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/060,291

(22) PCT Filed: Dec. 9, 2016

(86) PCT No.: PCT/FR2016/053296
§ 371 (c)(1),
(2) Date: Jun. 7, 2018

(87) PCT Pub. No.: WO2017/098180
PCT Pub. Date: Jun. 15, 2017

(65) Prior Publication Data
US 2018/0362549 A1 Dec. 20, 2018

(30) Foreign Application Priority Data
Dec. 9, 2015 (FR) .................................. 15 62068

(51) Int. Cl.
| | |
|---|---|
| C07F 5/00 | (2006.01) |
| C07F 15/00 | (2006.01) |
| G01N 33/58 | (2006.01) |
| C07D 401/14 | (2006.01) |

(52) U.S. Cl.
CPC ............ C07F 5/003 (2013.01); C07D 401/14 (2013.01); G01N 33/582 (2013.01); *G01N 2458/40* (2013.01)

(58) Field of Classification Search
CPC ... C07F 15/00; C07F 5/00; C07F 3/00; G01N 33/582
See application file for complete search history.

(56) References Cited

U.S. PATENT DOCUMENTS

| | | | |
|---|---|---|---|
| 4,761,481 | A | 8/1988 | Hale et al. |
| 4,859,777 | A | 8/1989 | Toner |
| 4,920,195 | A | 4/1990 | Kankare et al. |
| 5,202,423 | A | 4/1993 | Kankare et al. |
| 5,216,134 | A | 6/1993 | Mukkala et al. |
| 5,324,825 | A | 6/1994 | Kankare et al. |
| 5,385,893 | A | 1/1995 | Kiefer |

(Continued)

FOREIGN PATENT DOCUMENTS

| | | |
|---|---|---|
| EP | 0180492 | 5/1986 |
| EP | 0321353 | 6/1989 |

(Continued)

OTHER PUBLICATIONS

Goretti Castro et al, Lanthanide (III) complexation with an amide derived pyridinophane, Inorg. Chem, 54, 1671-1683. (Year: 2015).*
International Search Report issued in International Application No. PCT/FR2016/053296 dated Feb. 22, 2017 (5 pages).
Written Opinion issued in International Application No. PCT/FR2016/053296 dated Feb. 22, 2017 (5 pages).
Castro et al.: "Lanthanide(III) Complexation with an Amide Derived Pyridinophane"; Inorganic Chemistry, vol. 54, pp. 1671-1683.

(Continued)

*Primary Examiner* — Michael G. Hartley
*Assistant Examiner* — Jagadishwar R Samala
(74) *Attorney, Agent, or Firm* — Hamre, Schumann, Mueller & Larson, P.C.

(57) ABSTRACT

The invention relates to complexing agents of formula (I)

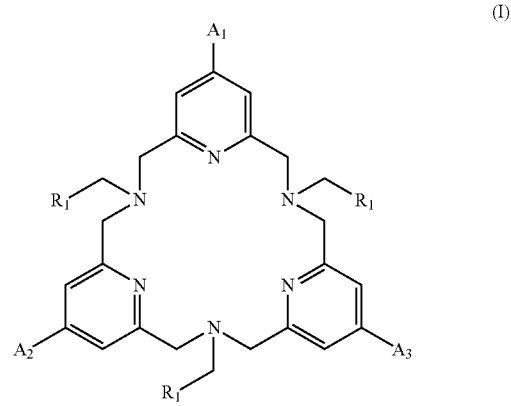

in which $A_1$, $A_2$, $A_3$ and $R_1$ are as defined in the description. The invention also relates to lanthanide complexes obtained from said complexing agents.

The invention can be used for marking biological molecules.

19 Claims, 1 Drawing Sheet

(56) References Cited

U.S. PATENT DOCUMENTS

| | | |
|---|---|---|
| 5,622,821 A | 4/1997 | Selvin et al. |
| 5,662,821 A | 9/1997 | Ruckl |

FOREIGN PATENT DOCUMENTS

| | | |
|---|---|---|
| EP | 0601113 | 6/1994 |
| WO | 9305049 | 3/1993 |
| WO | 9423276 | 11/1994 |
| WO | 200196877 | 12/2001 |
| WO | 2008063721 | 5/2008 |
| WO | 2014111661 | 7/2014 |

OTHER PUBLICATIONS

Zwier, J. M. et al., "Luminescent Lanthanide Cryptates: from the Bench to the Bedside," Inorganic Chemistry, 2014, 53, pp. 1854-1866.

Bunzli, Jean-Claude G., "Lanthanide Luminescence for Biomedical Analyses and Imaging," Chemical Reviews, 2010, vol. 110, No. 5, pp. 2729-2755.

Lee, G., et al., "Efficient Synthesis of 2,11,20-Triaza[3.3.3](2,6)pyridinophane," Journal of Organic Chemistry, 1996, 61, pp. 8304-8306.

Nolan, C. et al., "Improved synthesis of a C3-symmetrical pyridinophane," Tetrahedron Letters, 2008, 49, pp. 1993-1996.

Gastro, G. et al., "Lanthanide(III) Complexation with an Amide Derived Pyridinophane," Inorganic Chemistry, 2015, 54, pp. 1671-1683.

Gastro, G. et al., "Pyridinophane Platform for Stable Lanthanide(III) Complexation," Inorganic Chemistry, 2013, 52, pp. 6062-6072.

\* cited by examiner ically, on the one hand the laser sources used in bioassays for exciting the donor fluorophores emit at various wavelengths: 337 nm (nitrogen laser), 355 nm (Nd:YAG laser), 349 nm (Nd:YLF) and on the other hand the flash lamps that enable excitation between 310 and 350 nm: the compounds from the prior art, optimally absorbing at 267 nm, cannot be excited by these devices.

WATER-SOLUBLE TRIAZAPYRIDINOPHANE-BASED COMPLEXING AGENTS AND CORRESPONDING FLUORESCENT LANTHANIDE COMPLEXES

The present invention relates to novel water-soluble complexing agents based on macrocycles of triazapyridinophane type, fluorescent lanthanide complexes obtained from these complexing agents, and the use of these fluorescent lanthanide complexes for labeling molecules and detecting them by time-resolved fluorescence techniques.

PRIOR ART

Europium and terbium complexes are from now on accepted by the whole of the scientific community as being fluorescent probes of choice (Inorganic Chemistry 2014, 53, 1854, Chemical Reviews 2010, 110, 2729). Indeed, owing to their very specific photophysical properties, these molecules have been widely used in industry and studied by university laboratories in the field of life sciences. These fluorescent compounds are particularly suitable for being used in conjunction with compatible fluorophores to carry out FRET (Förster resonance energy transfer) measurements, the application of which for studying the interactions between biomolecules is exploited commercially by several companies, including Cisbio Bioassays and its HTRF® product range. The relatively long emission lifetime of lanthanide complexes also makes it possible to carry out time-resolved fluorescent measurements, i.e. with a delay after excitation of the fluorophores, which makes it possible to limit the fluorescence interferences due to the measurement medium. The latter feature is all the more useful as the measurement medium approaches a biological medium, which comprises numerous proteins whose fluorescence could interfere with that of the compounds studied.

Many lanthanide complexes have been disclosed and some are exploited commercially: mention may in particular be made of the macropolycyclic cryptates of lanthanides (EP 0 180 492, EP 0 321 353, EP 0 601 113, WO 2001/96877, WO2008/063721), the lanthanide complexes comprising a unit derived from coumarin bonded to a diethylenetriamine penta-acid unit (U.S. Pat. No. 5,622,821), and those comprising derivatives of pyridine (U.S. Pat. Nos. 4,920,195, 4,761,481), of bipyridine (U.S. Pat. No. 5,216,134), or of terpyridine (U.S. Pat. No. 4,859,777, 5,202,423, 5,324,825).

U.S. Pat. No. 5,385,893 describes derivatives of triazapyridinophanes, the three nitrogens of which are substituted by (carboxylic or phosphonic) acid groups, and complexes of these compounds with a gadolinium, manganese or iron atom. The complexes described are not fluorescent and may be used as contrast agents. The triazapyridinophanes according to U.S. Pat. No. 5,385,893 are not very suitable for the preparation of fluorescent complexes due to the size of the macrocyclic cage that enables exchanges of water molecules relatively easily. The synthesis of this triazapyridinophane macrocycle was carried out with a yield of 2%. Obtaining this compound is not direct and inevitably passes through the use of an intermediate, from which the three nitrogen atoms belonging to the macrocycle are protected by tosyl groups. The latter are eliminated at the end of the synthesis under extreme conditions.

Slightly more recently, the improvement in the synthesis was reported by Lee et al. (Journal of Organic Chemistry 1996, 61, 8304) who obtain better yields. The macrocyclic compound is obtained according to a convergent synthesis comprising 8 steps, the last one of which consists in deprotecting the tosyl groups, here too in a highly acid medium. These macrocycles are not used as complexing ligands.

In 2008 Nolan et al. attempted to reproduce the synthesis process described by Lee but failed, which led them to develop a new convergent synthesis strategy (Tetrahedron Letters 2008, 49, 1993). The final step of tosyl deprotection is once again carried out in a very acid medium.

Recently, the studies by Castro et al. on triazapyridinophane-type macrocyclic systems (Inorganic Chemistry 2015, 54, 1671 and Inorganic Chemistry 2013, 52, 6062) have made it possible to characterize the corresponding lanthanide complexes by X-ray diffraction. However, the synthesis method used is the same as that described previously by Lee et al.

The triazapyridinophane macrocycles from the prior art are not suitable for use for FRET bioassays:

The triazapyridinophane macrocycles complexed with a europium or terbium atom described previously have optimal absorption wavelengths at 267 nm which is unacceptable for use as donor fluorescent compounds for FRET measurements. Specifically, on the one hand the laser sources used in bioassays for exciting the donor fluorophores emit at various wavelengths: 337 nm (nitrogen laser), 355 nm (Nd:YAG laser), 349 nm (Nd:YLF) and on the other hand the flash lamps that enable excitation between 310 and 350 nm: the compounds from the prior art, optimally absorbing at 267 nm, cannot be excited by these devices.

The triazapyridinophane macrocycles from the prior art are relatively hydrophobic, which is a problem for their use in bioassays in aqueous media and may result in a considerable non-specific signal in FRET measurements. Furthermore, the complexes not very soluble in aqueous media very simply cannot be used.

The methods for synthesizing these macrocycles comprise several steps, the last of which requires very extreme experimental conditions for the release of the secondary amine functions protected by tosyl groups, namely several hours of reaction in concentrated sulfuric acid at 120° C. This is a real obstacle for the synthesis of more elaborate molecules that can be used as fluorophore in FRET-type bioassays, since these conditions are not compatible with the addition of functions sensitive to these conditions.

It is furthermore important to note that the methods for synthesizing triazapyridinophanes described in the literature only make it possible to attain compounds of $C_3$ symmetry and therefore do not make it possible to differentiate the substituents borne by the three pyridine rings in order to obtain compounds suitable for use as fluorophore in FRET bioassays.

Finally, the triazapyridinophane macrocycles from the prior art are not only unsuitable for use as fluorophore in FRET-type bioassays, due to their spectroscopic properties and their hydrophobicity, but in addition the methods described for their syntheses make any adaptation of these molecules to this application impossible (molecules of $C_3$ symmetry, excessively extreme conditions for deprotection of the amines).

There is therefore a need for triazapyridinophane macrocycles and corresponding lanthanide complexes that can be used in FRET-type bioassays.

The present invention aims to overcome the drawbacks of the compounds from the prior art and to provide fluorescent lanthanide complexes that have better brightness than the compounds from the prior art when they are excited between 310 and 350 nm, if possible a good solubility in aqueous media, an emission spectrum suitable for the use thereof in FRET experiments, and also being very convenient for labeling biomolecules.

DESCRIPTION OF THE INVENTION

Figure 1:
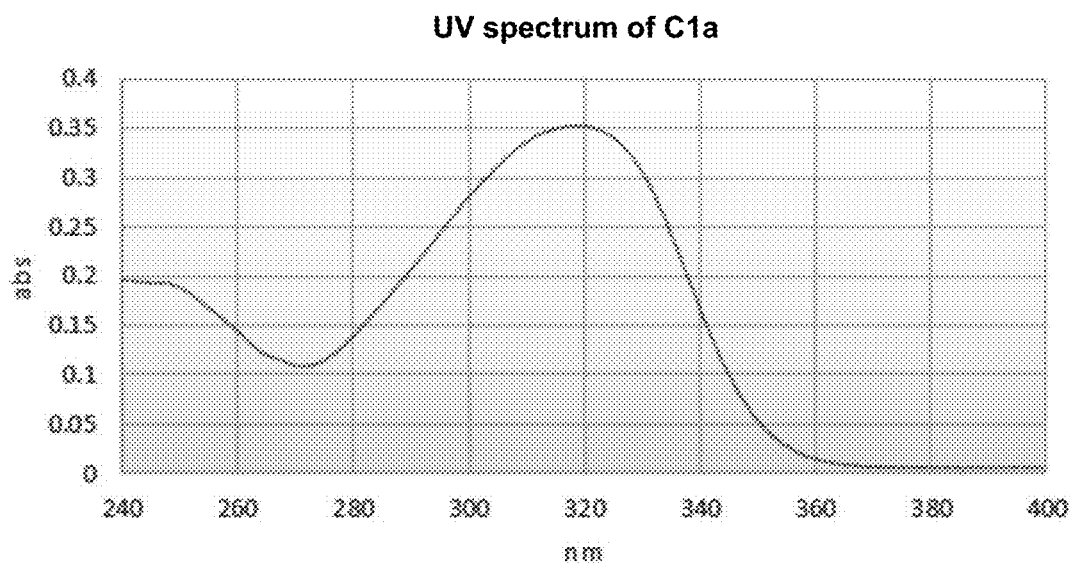
FIG. 1 shows the absorption spectrum of a complex of the invention.

The inventors have gone beyond the technical prejudice according to which triazapyridinophanes are not very suitable for preparing fluorescent complexes due to the size of the macrocyclic cage that enables exchanges of water molecules relatively easily. The abovementioned problems have been solved owing to the creation of a synthesis protocol enabling the preparation of complexing agents made up of a triazapyridinophane macrocycle, the pyridines of which are substituted by para-methoxyphenylacetylene or 2,4,6-trimethoxyphenyl groups, these groups themselves bearing groups capable of increasing the water solubility of the macrocycles, and optionally a group that enables the conjugation of the macrocycles with other molecules, in particular biological molecules that it is desired to label with a fluorescent compound.

The invention therefore relates to complexing agents based on a triazapyridinophane macrocycle, fluorescent lanthanide complexes consisting of a lanthanide atom complexed by a complexing agent according to the invention, and organic molecules of interest labeled by a complex according to the invention.

Complexing Agents

The complexing agents according to the invention are the compounds of formula (I):

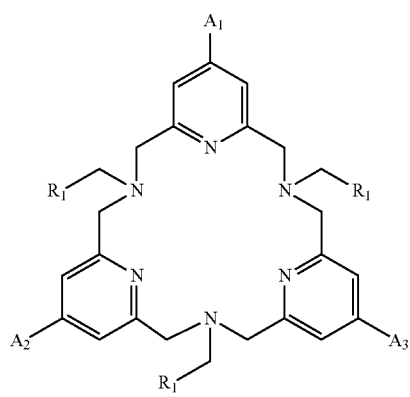

(I)

wherein:
the $R_1$ groups are identical and are chosen from: —$CO_2H$, —PO(OH)R, R being chosen from the groups: phenyl, phenyl substituted by an —$SO_3H$ group, preferably in the ortho or para position, benzyl, methyl, ethyl, propyl, n-butyl, sec-butyl, isobutyl, tert-butyl;
the $A_1$, $A_2$ groups are identical or different and are chosen from: a group of formula -$L_1$-E; a group of formula (II) or (II');

the $A_3$ group is chosen from: a group of formula —O-$L_3$-G, a group of formula (II), (II'), (III) or (III');

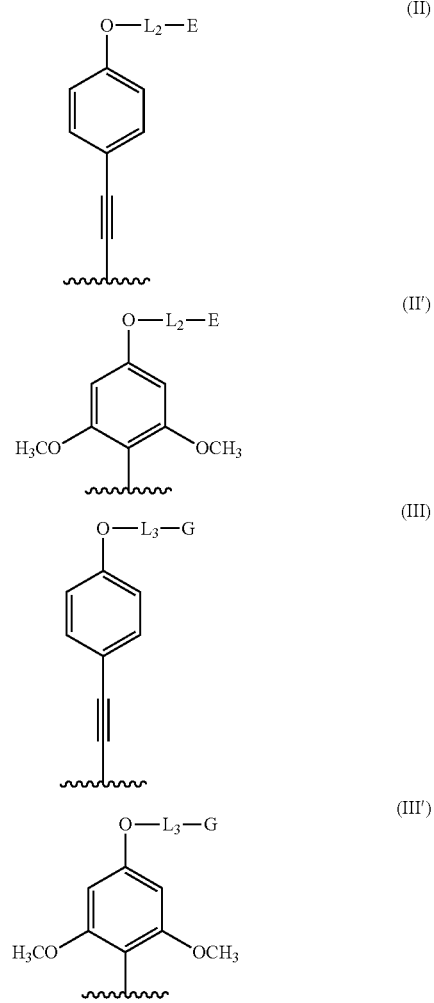

$L_1$, $L_2$ and $L_3$ are identical or different and represent a divalent linkage group;
E is a group that renders the complexing agent water-soluble, chosen from: —$SO_3H$, —PO(OH)$_2$, —$CO_2H$, —$N^+Alk_1Alk_2Alk_3$, a carbohydrate residue, a sulfobetaine; a PEG group;
G is a reactive group;
$Alk_1$, $Alk_2$, $Alk_3$, which may be identical or different, represent a ($C_1$-$C_6$)alkyl.

A carbohydrate is understood to mean: a glucose residue in cyclic or linear form, or else a group of formula —(CHOH)$_k$—CH$_2$OH, k being an integer ranging from 3 to 12, preferably equal to 4.

A sulfobetaine is understood to mean a group chosen from:

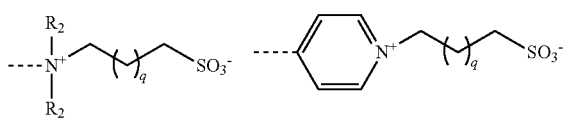

with $R_2$ which represents an alkyl group having 1 to 6 carbon atoms, and preferably a methyl or ethyl, and q which is equal to 1, 2, 3, 4, 5 or 6, and preferably which is equal to 1 or 2, the sulfobetaine of formula —$(CH_3)_2N^+$—$(CH_2)_3$—$SO_3^-$ being preferred.

Depending on the pH, the —$SO_3H$, —$CO_2H$ and —$PO(OH)_2$ groups are optionally in deprotonated form. These groups therefore also denote, in the remainder of the text, the —$SO_3^-$, —$CO_2^-$ and —$PO(OH)O^-$ groups, and vice versa.

A PEG group is understood to mean a polyethylene glycol group of formula —$CH_2$—$(CH_2OCH_2)_y$—$CH_2OCH_3$, y being an integer ranging from 1 to 5.

The (II), (II'), (III) and (III') groups contribute to the formation of antennae that contribute to the spectroscopic properties of the fluorophores. The -$L_1$-E, (II) and (II') groups bear E groups which render the complexing agents water-soluble, and the —O-$L_3$-G, (III) and (III') groups bear a reactive group G that makes it possible to conjugate the fluorescent complexes according to the invention with a molecule of interest that it is desired to label.

According to the invention, the antennae comprise 2,4,6-methoxyphenyl (II'), (III') groups or para-methoxyphenylacetylene (II), (III) groups, the latter being preferred. Furthermore, the compounds according to the invention may comprise 1, 2 or 3 antennae, and the complexing agents according to the invention may thus be subdivided into the following preferred subfamilies, based on para-methoxyphenylacetylene antennae:

Complexing agents with 3 antennae, comprising 2 solubilizing groups and one reactive group that correspond to the compounds of formula (I) in which $A_1$ and $A_2$ are identical and are groups of formula (II) and $A_3$ is a group of formula (III).

Complexing agents with 2 antennae comprising 2 solubilizing groups and one reactive group that correspond to the compounds of formula (I) in which $A_1$ is a group of formula (II), $A_2$ is an -$L_1$-E group and $A_3$ is a group of formula (III).

Complexing agents with 2 antennae comprising 2 solubilizing groups and one reactive group that correspond to the compounds of formula (I) in which $A_1$ and $A_2$ are identical and are groups of formula (II), and $A_3$ is a group of formula —O-$L_3$-G.

Complexing agents with 1 antenna, comprising 2 solubilizing groups and one reactive group that correspond to the compounds of formula (I) in which $A_1$ and $A_2$ are identical and are groups of formula -$L_1$-E and $A_3$ is a group of formula (III).

The same subfamilies based on para-methoxyphenyl antennae are distinguished by replacing the groups of formula (II) and (III) with the groups of formula (II') and (III'), respectively, namely:

Complexing agents with 3 antennae, comprising 2 solubilizing groups and one reactive group that correspond to the compounds of formula (I) in which $A_1$ and $A_2$ are identical and are groups of formula (II') and $A_3$ is a group of formula (III').

Complexing agents with 2 antennae comprising 2 solubilizing groups and one reactive group that correspond to the compounds of formula (I) in which $A_1$ is a group of formula (II'), $A_2$ is an -$L_1$-E group and $A_3$ is a group of formula (III').

Complexing agents with 2 antennae comprising 2 solubilizing groups and one reactive group that correspond to the compounds of formula (I) in which $A_1$ and $A_2$ are identical and are groups of formula (II'), and $A_3$ is a group of formula —O-$L_3$-G.

Complexing agents with 1 antenna, comprising 2 solubilizing groups and one reactive group that correspond to the compounds of formula (I) in which $A_1$ and $A_2$ are identical and are groups of formula -$L_1$-E and $A_3$ is a group of formula (III').

For each of these subfamilies, the $R_1$ groups that participate in the complexing of the lanthanide may be either a carboxylate —$CO_2H$ or a phosphinate —PO(OH)R as defined above (and preferably in the latter case a methylphosphinate).

For each of these subfamilies, the compounds for which the E groups are either —$SO_3^-$ groups, or a glucose residue, or an ammonium —$N^+(CH_3)_3$ or else a sulfobetaine of formula below are preferred

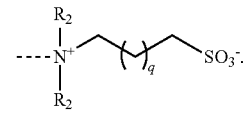

The compounds for which the E groups are either —$SO_3^-$ groups, or a glucose residue, or a sulfobetaine of formula above are particularly preferred.

The reactive group G borne by a spacer arm $L_3$ makes it possible to couple the compounds according to the invention with a species that it is desired to render fluorescent, for example an organic molecule, a peptide or a protein. The techniques for conjugating two organic molecules are based on the use of reactive groups and come under the general knowledge of a person skilled in the art. These conventional techniques are described for example in Bioconjugate Techniques, G. T. Hermanson, Academic Press, Second Edition 2008, p. 169-211.

Typically, the reactive group is an electrophilic, nucleophilic, diene or dienophile group which may form a covalent bond when it is placed in the presence of an appropriate nucleophilic, electrophilic, dienophile or diene group, respectively. The conjugation reaction between a compound according to the invention comprising a reactive group and an organic molecule, a peptide or a protein bearing a functional group leads to the formation of a covalent bond comprising one or more atoms of the reactive group.

Preferably, the reactive group G is a group derived from one of the compounds below: an acrylamide, an activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine or dichlorotriazine, a hydrazine (including hydrazides), an imido ester, an isocyanate, an isothiocyanate, a maleimide, a sulfonyl halide, a thiol, a ketone, an amine, an acid halide, a succinimidyl ester, a hydroxysuccinimidyl ester, a hydroxysulfosuccinimidyl ester, an azidonitrophenyl, an azidophenyl, a glyoxal, a triazine, an acetylenic group, and the groups of formula:

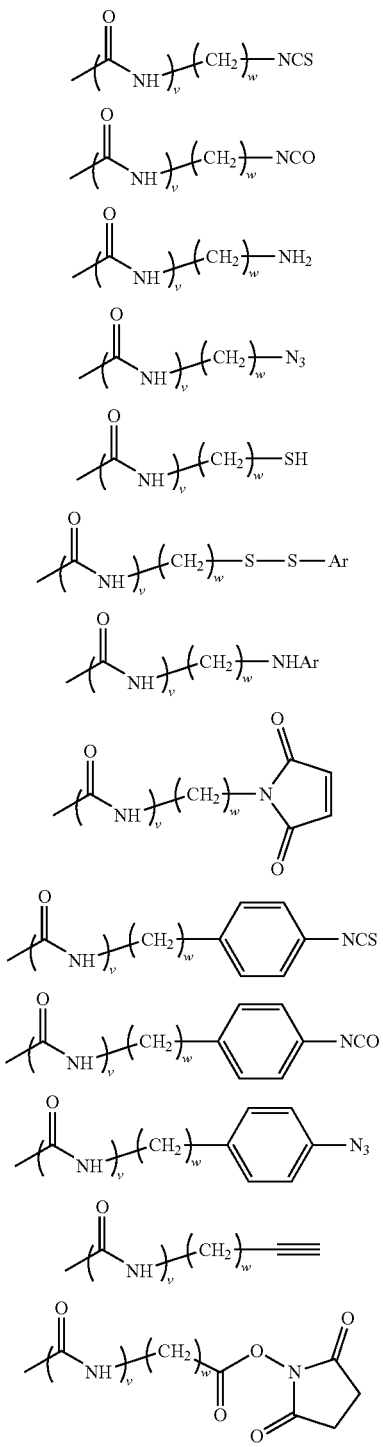

-continued

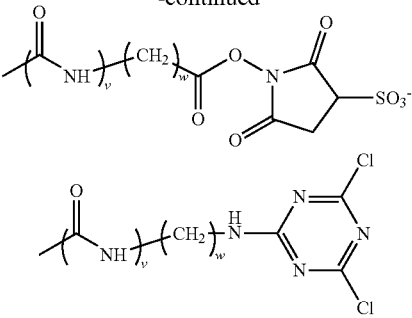

wherein w varies from 0 to 8 and v is equal to 0 or 1, and Ar is a saturated or unsaturated 5- or 6-membered heterocycle, comprising 1 to 3 heteroatoms, optionally substituted by a halogen atom.

Preferably, the reactive group G is a carboxylic acid, an amine, preferably an aliphatic amine (optionally protected in —NHBoc form), a succinimidyl ester, haloacetamide, a hydrazine, an isothiocyanate, a maleimide group or a carboxylic acid (optionally protected in the form of a —CO$_2$Me or —CO$_2$tBu group). In that case, the acid will have to be activated in ester form in order to be able to react with a nucleophilic species.

An organic molecule, a peptide or a protein capable of being labeled by a compound according to the invention will therefore comprise a functional group with which the reactive group of the lanthanide complex or of the complexing agent will react. For example, the organic molecule, the protein or the peptide comprises one of the following groups: amine, amide, thiol, alcohol, aldehyde, ketone, hydrazine, hydroxylamine, secondary amine, halide, epoxide, ester (alkyl carboxylate), carboxylic acid, groups comprising double bonds or a combination of these functional groups. The amine or thiol groups naturally present on the proteins are often used to carry out the labeling of these molecules.

The reactive group and the solubilizing groups E are bound to the complexing agent via a spacer arm ($L_1$, $L_2$, $L_3$) advantageously formed by a divalent organic radical, chosen from:

a linear or branched $C_1$-$C_{20}$ alkylene group optionally containing one or more double or triple bonds;

a $C_5$-$C_8$ cycloalkylene group or a $C_8$-$C_{14}$ arylene group, said alkylene, cycloalkylene or arylene groups optionally containing one or more heteroatoms, such as oxygen, nitrogen, sulfur, phosphorus or one or more carbamoyl or carboxamido groups, and said alkylene, cycloalkylene or arylene groups being optionally substituted by $C_1$-$C_8$ alkyl, $C_8$-$C_{14}$ aryl, sulfonate or oxo groups, a group chosen from the divalent groups of following formulae:

$$—(CH_2)_n—;$$
$$—(CH_2)_n—O—(CH_2)_m—O—(CH_2)_p—;$$

-continued

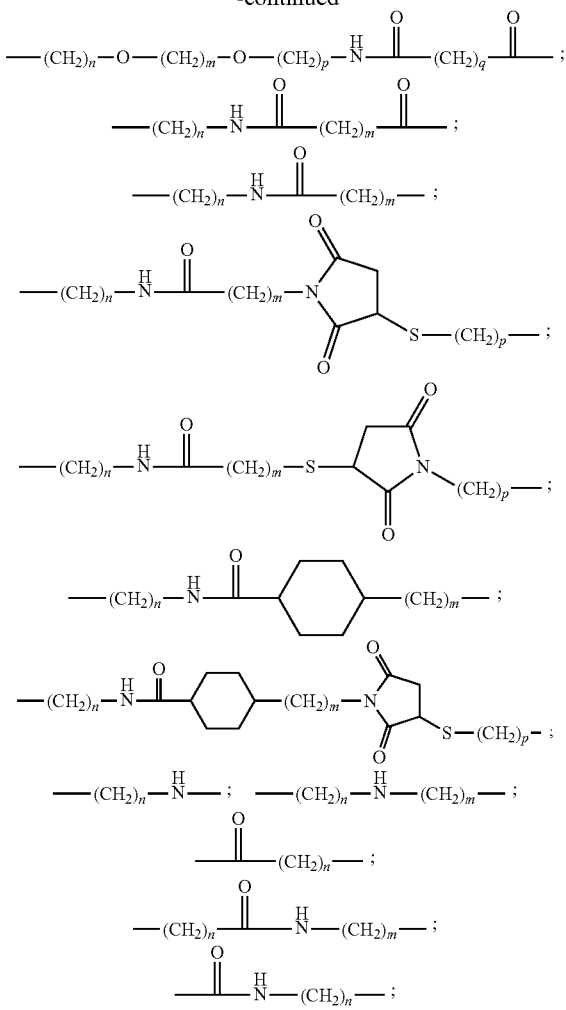

wherein n, m, p, q are integers from 1 to 16, preferably from 1 to 5.

Preferably, the -L$_3$G group consists of a reactive group G chosen from: a carboxylic acid (optionally protected in the form of a —CO$_2$Me or —CO$_2$tBu group), an amine, preferably an aliphatic amine (optionally protected in —NHBoc form), a succinimidyl ester, a haloacetamide, a hydrazine, an isothiocyanate, a maleimide group, and a spacer arm L$_3$ consisting of an alkylene chain comprising from 1 to 5 carbon atoms. More preferably still, the -L$_3$G group is an amine borne by an alkylene chain comprising from 1 to 5 carbon atoms.

As regards L$_1$, the following divalent group is preferred:

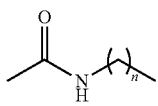

where n is an integer from 1 to 16, preferably from 1 to 5.

As regards L$_2$, the following divalent group is preferred:

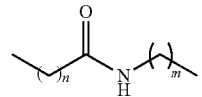

where n and m are integers from 1 to 16, preferably from 1 to 5.

As regards L$_3$, the following divalent group is preferred:

where n is an integer from 1 to 16, preferably from 1 to 5.

The subfamilies in which, simultaneously,

L$_1$ is the divalent group of formula:

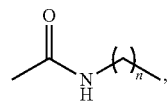

and

L$_2$ is the divalent group of formula

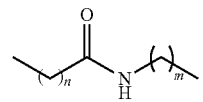

and

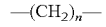

L$_3$ is the divalent group of formula are also preferred.

Complexes

The invention also relates to the fluorescent lanthanide complexes consisting of a lanthanide atom complexed by a complexing agent as described above. Preferably, the lanthanide is Tb$^{3+}$, Eu$^{3+}$ or Sm$^{3+}$ and more preferably still Eu$^{3+}$.

These complexes are prepared by bringing the complexing agents according to the invention and a lanthanide salt into contact. Thus, the reaction between one equivalent of complexing agent and 1 to 5 equivalents of lanthanide salt (europium, terbium or samarium for example in the form of chlorides) in an aqueous medium at pH 6 results, after reacting for several hours or even several days at room temperature, in the corresponding complex.

As indicated previously, the fluorescent complexes obtained have excellent photophysical properties, in particular as regards their quantum efficiency, the lifetime of their luminescence and their excitation spectrum which is very well suited to a laser excitation at around 337 nm. Furthermore, the distribution of the bands of their emission spectra is centered around 620 nm thus giving the complexes exceptional properties that are highly favorable when using FRET with acceptors of the cyanine or allophycocyanin type (such as XL665 sold by Cisbio Bioassays).

Advantageously, the invention relates to the following complexes:

(IV)
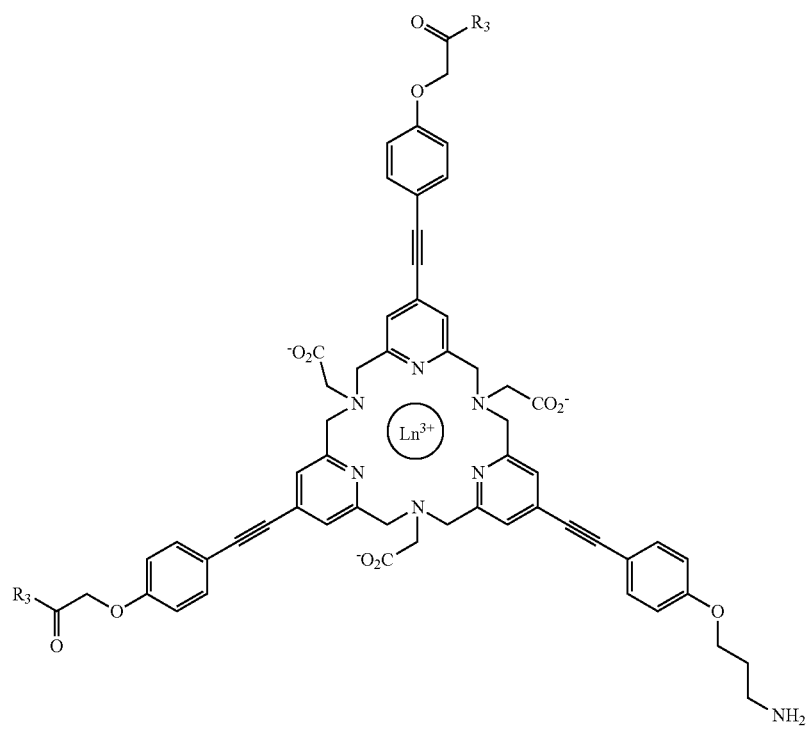
(V)
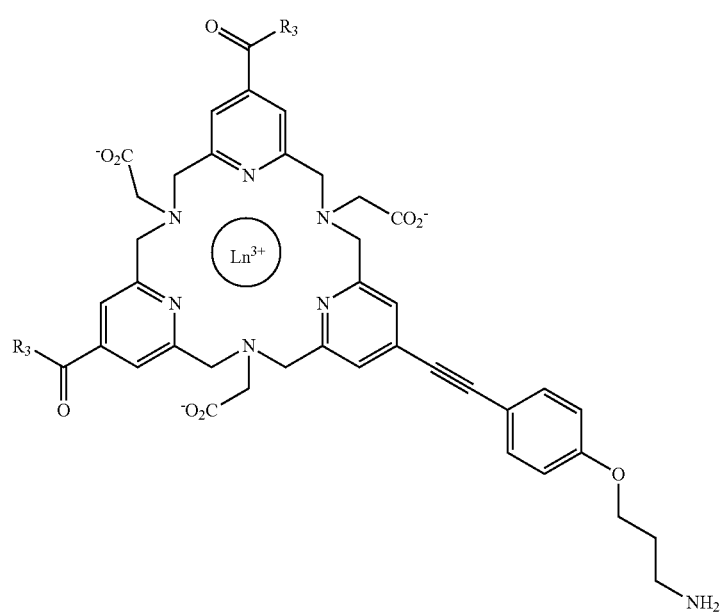

-continued
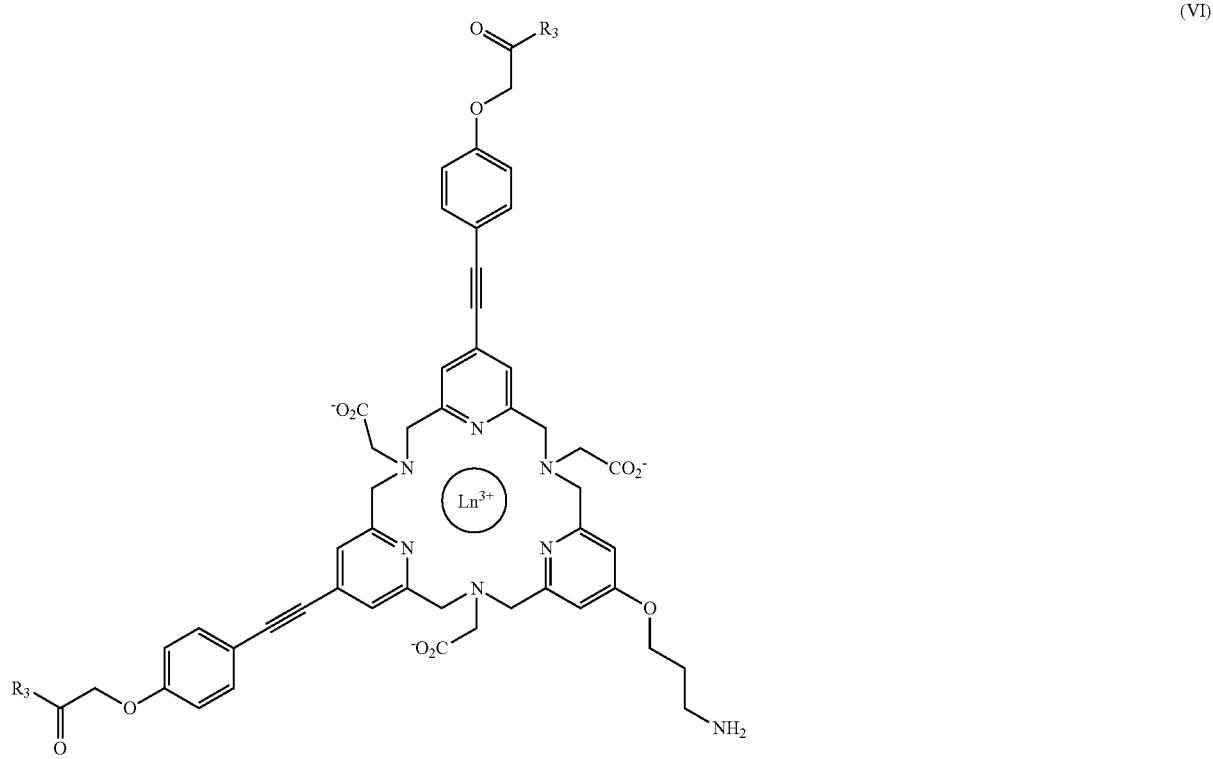
(VI)
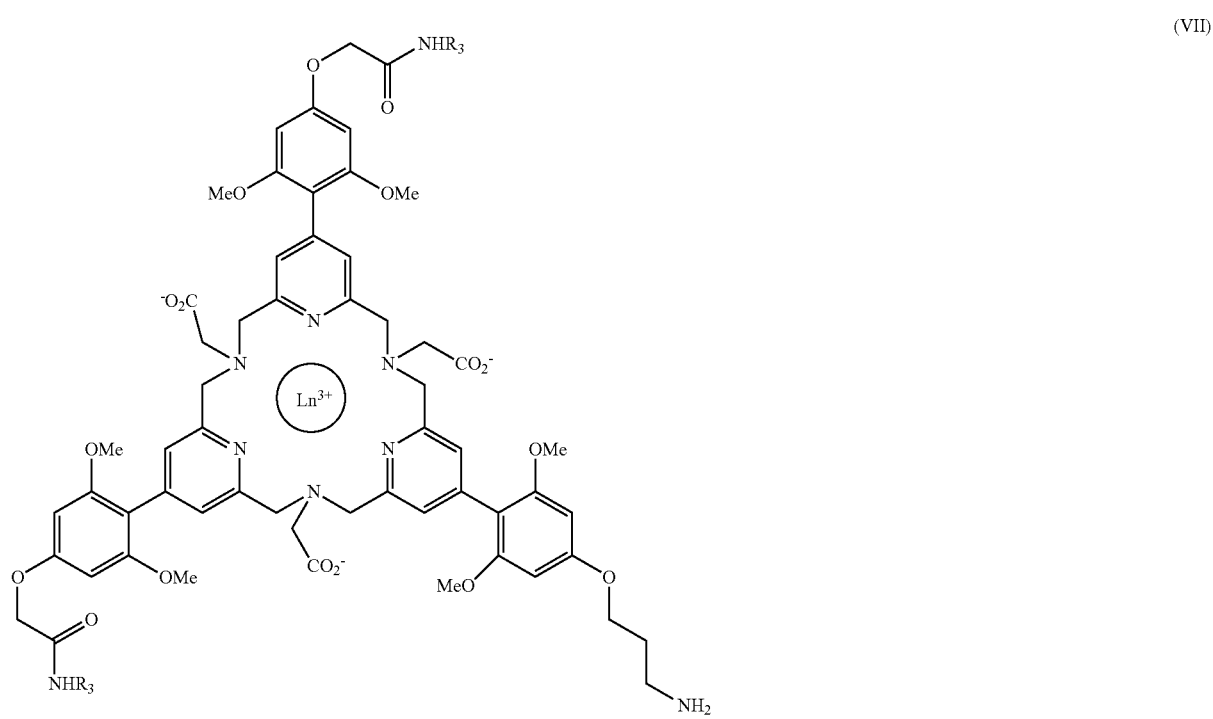
(VII)

wherein:
Ln$^{3+}$ is chosen from: Eu$^{3+}$, Tb$^{3+}$, Sm$^{3+}$;
R$_3$ is chosen from the following groups: OH

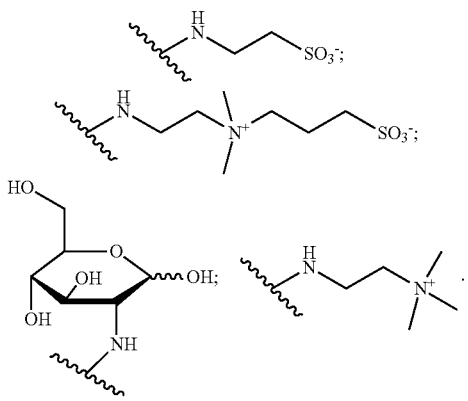

Conjugates

The complexing agents and complexes according to the invention comprising a reactive group are particularly suitable for labeling organic or biological molecules comprising a functional group capable of reacting with the reactive group to form a covalent bond. Thus, the invention also relates to the use of complexes for labeling biological molecules (proteins, antibodies, enzymes, hormones, etc.).

The invention also relates to the molecules labeled with a complex according to the invention. All organic or biological molecules may be conjugated with a complex according to the invention if they possess a functional group capable of reacting with the reactive group. In particular, the conjugates according to the invention comprise a complex according to the invention and a molecule chosen from: an amino acid, a peptide, a protein, an antibody, a sugar, a carbohydrate chain, a nucleoside, a nucleotide, an oligonucleotide, an enzyme substrate (in particular a suicide enzyme substrate such as a benzylguanine or a benzylcytosine (substrates of the enzymes sold under the names SNAP-Tag® and CLIP-Tag®)), a chloroalkane (substrate of the enzyme sold under the name Halo-tag), coenzyme A (substrate of the enzyme sold under the name ACP-tag or MCP-tag). The conjugates of the invention are obtained by bringing a lanthanide complex according to the invention, comprising a reactive group G, into contact with a molecule of interest.

Syntheses

The preparation of the complexing agents and of the lanthanide complexes according to the invention is described schematically below, and in more detail in the experimental section.

Synthesis of tri-antennae
(pyridyl-acetylene-4-O-phenyl) systems

The synthesis of complexes comprising 3 antennae, 2 solubilizing groups and 1 reactive group is described in schemes 1-4 and is based on a convergent synthesis. The compounds comprising other solubilizing groups/reactive groups may be prepared in a similar manner from the intermediate 24.

Scheme 1

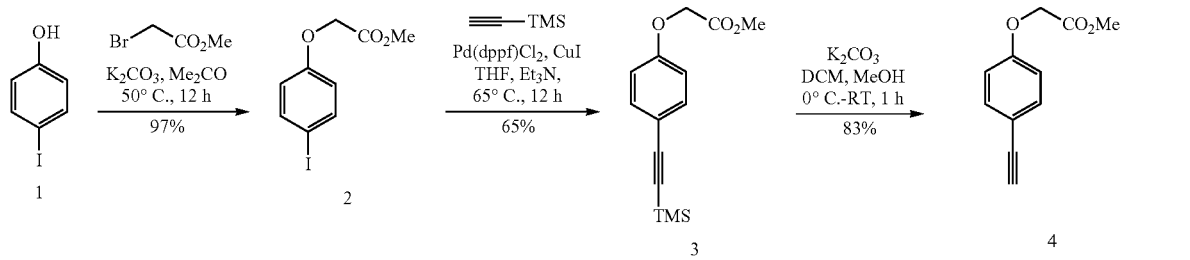

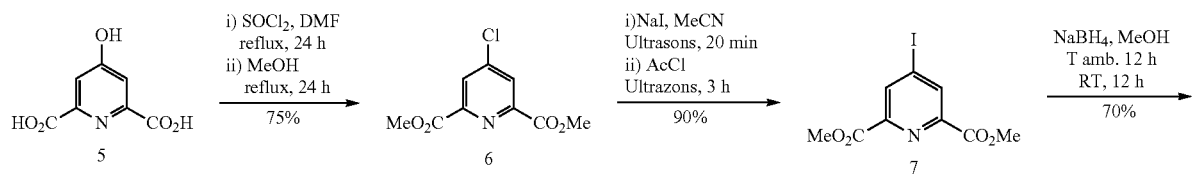

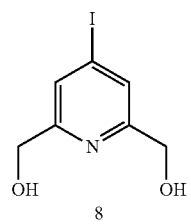

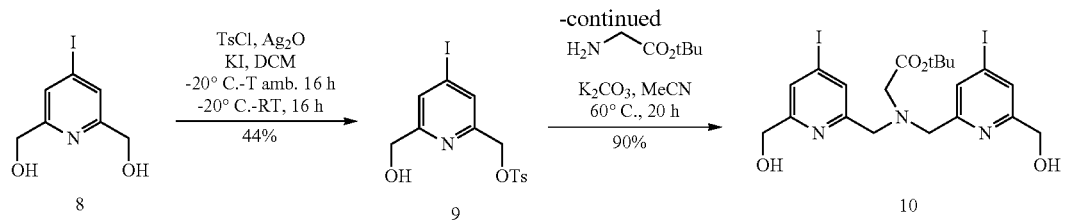

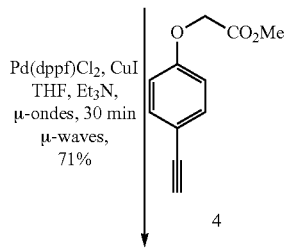

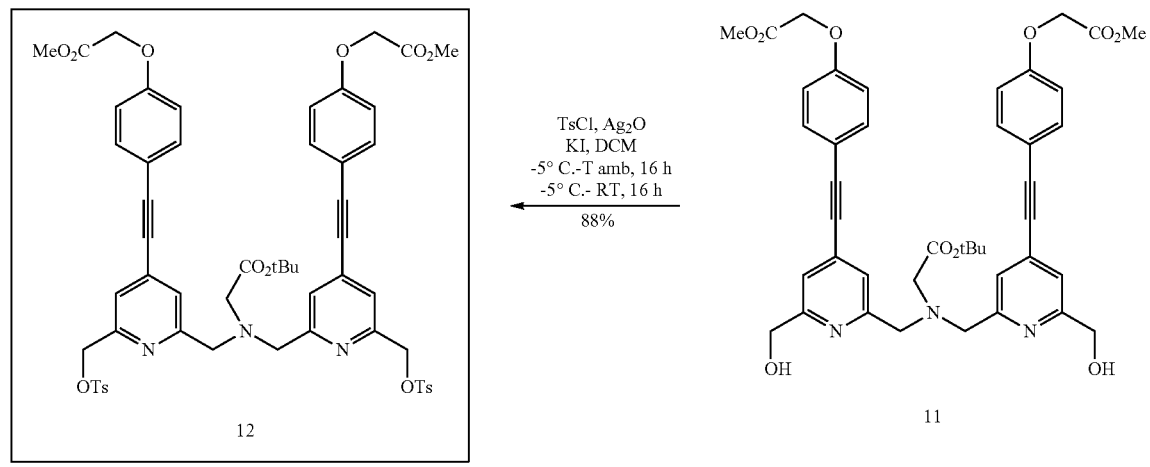

The introduction of the ester function that subsequently enables the attachment of a solubilizing function of sulfonate, sulfobetaine, ammonium or sugar derivative type is carried out by an alkylation reaction on 4-iodophenol. A Sonogashira type coupling reaction between the derivative 2 and trimethylsilylacetylene makes it possible to obtain the compound 3. The (trimethylsilyl) protecting group is removed using a mixture of methanol-dichloromethane solvents in the presence of potassium carbonate. These conditions make it possible to spare the methyl ester function which is relatively sensitive to hydrolysis. The diol 8 is obtained from chelidamic acid in 3 steps as described in the literature (Tetrahedron 2005, 61, 1755; Tetrahedron 2008, 64, 399; European Journal of Organic Chemistry 2002, 21, 3680). The monotosylation reaction is carried out in the presence of silver salts. These conditions were developed on the non-halogenated analogue (Tetrahedron 2004, 49, 11117; and Angewandte Chemie, International Edition 2014, 53, 5872). The condensation reaction makes it possible to obtain the dipyridinyl moiety 10 on which a double Sonogashira reaction is carried out that leads to the backbone of the first key synthon. The diol functions are activated by the introduction of tosyl groups under conditions quite similar to those of the monotosylation.

Scheme 2

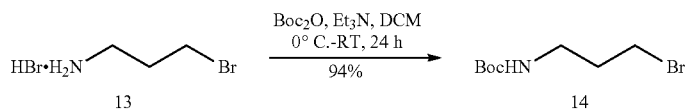

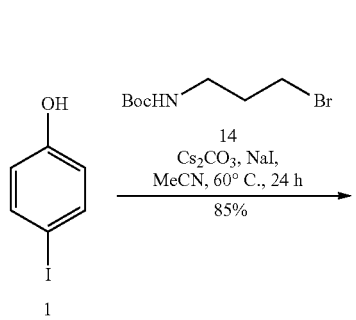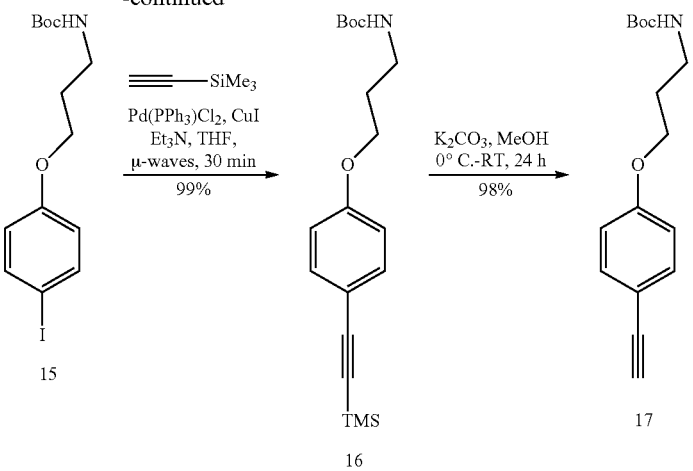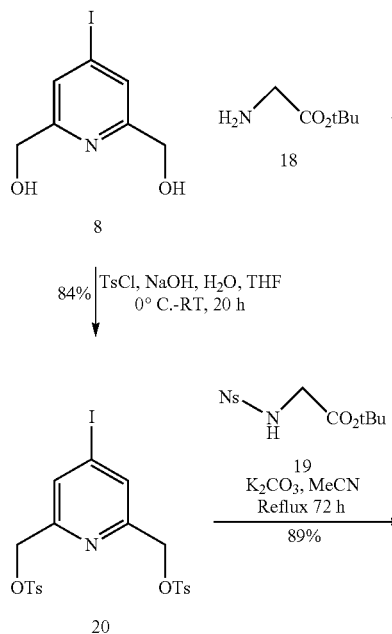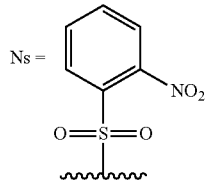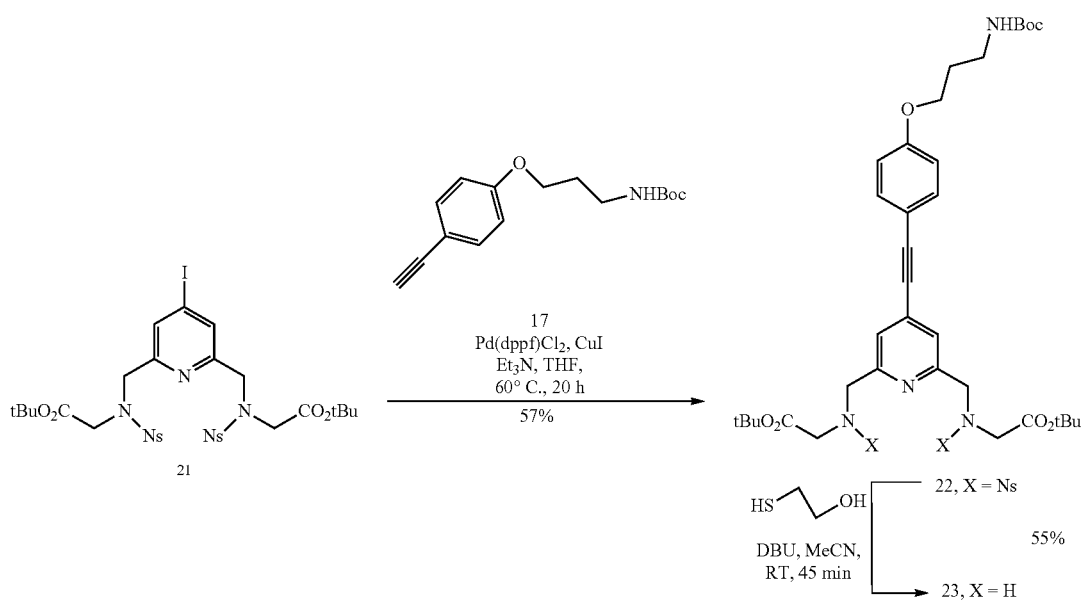

The synthesis of the second key synthon 23 is described in scheme 2. This synthon will bear a masked (Boc protecting group) amine function enabling for example a bioconjugation reaction with an antibody or a biomolecule. The compound 17 was prepared according to the procedures describned in the literature (WO 2014/111661). The diol 8 is activated in ditosylate form then condensed with the compound 19 resulting in the compound 21 with a good yield. The Sonogashira reaction followed by the deprotection of the nosyl group enables the synthon 23 to be obtained.

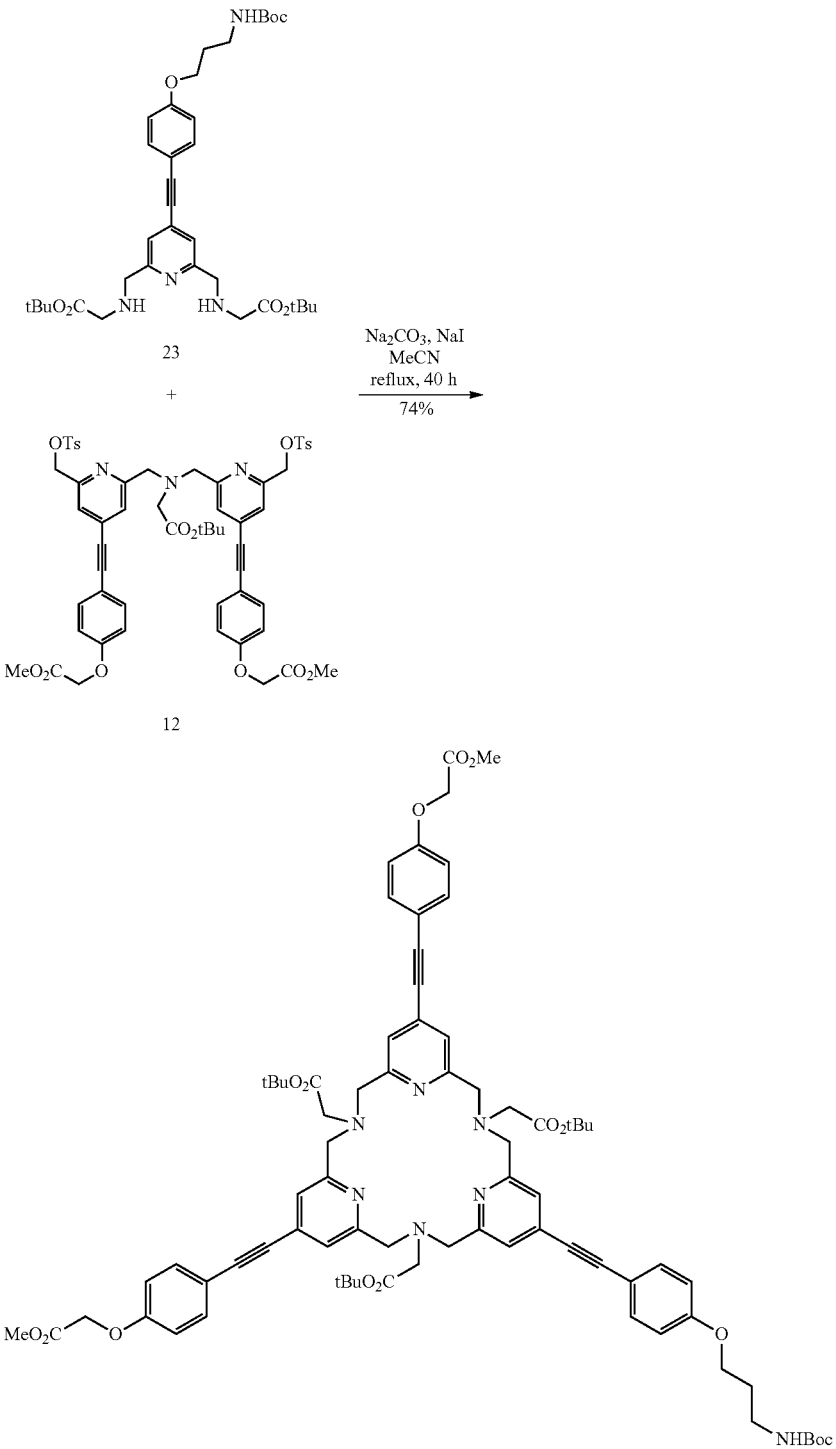

Scheme 3

The trickiest step is represented in scheme 3. It is the macrocyclization step which, after optimization, resulted in the ligand 24 with a very reasonable yield. This intermediate forms a platform for producing series of complexes of lanthanides (europium, terbium and samarium) bearing various solubilizing groups as described in scheme 4.

Scheme 4
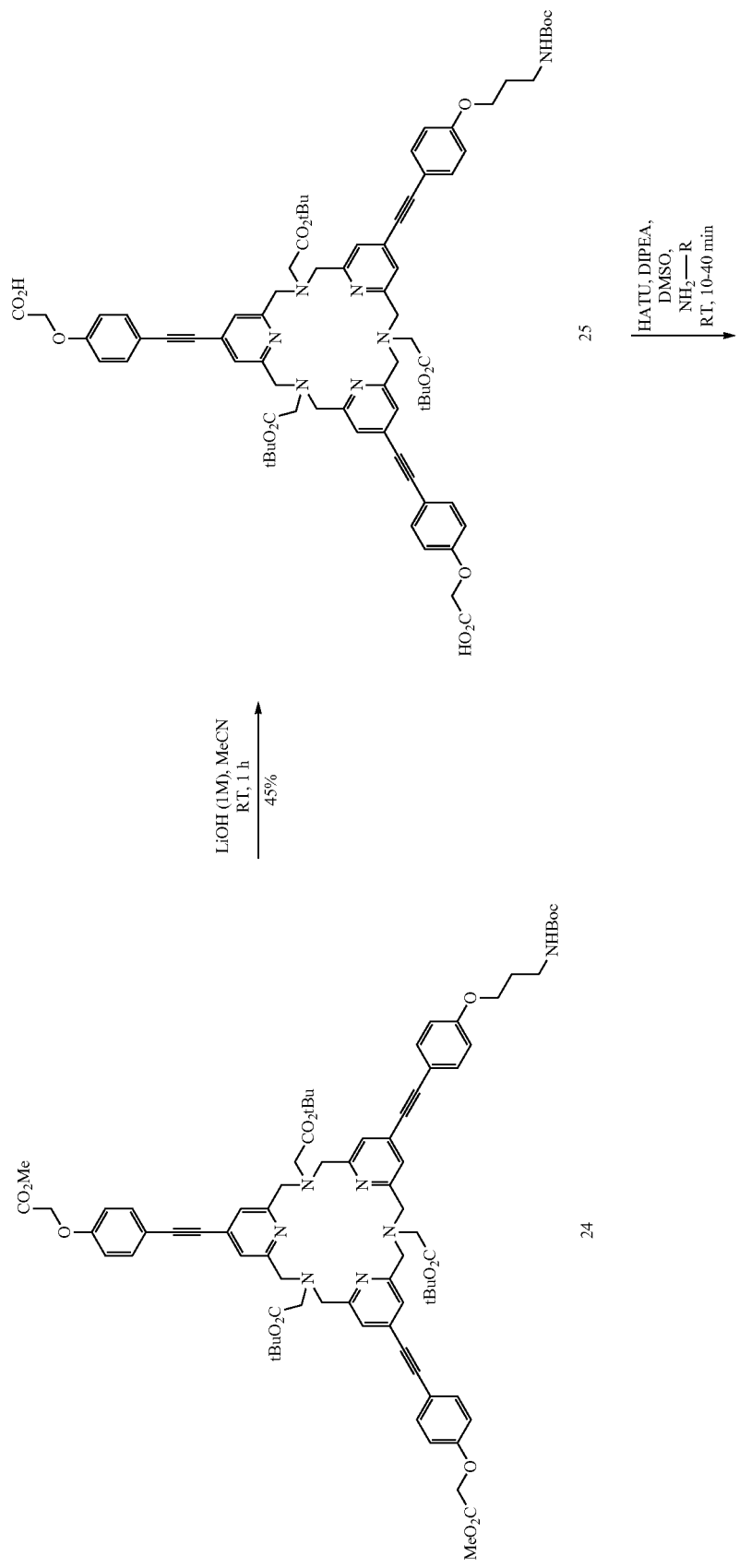

-continued
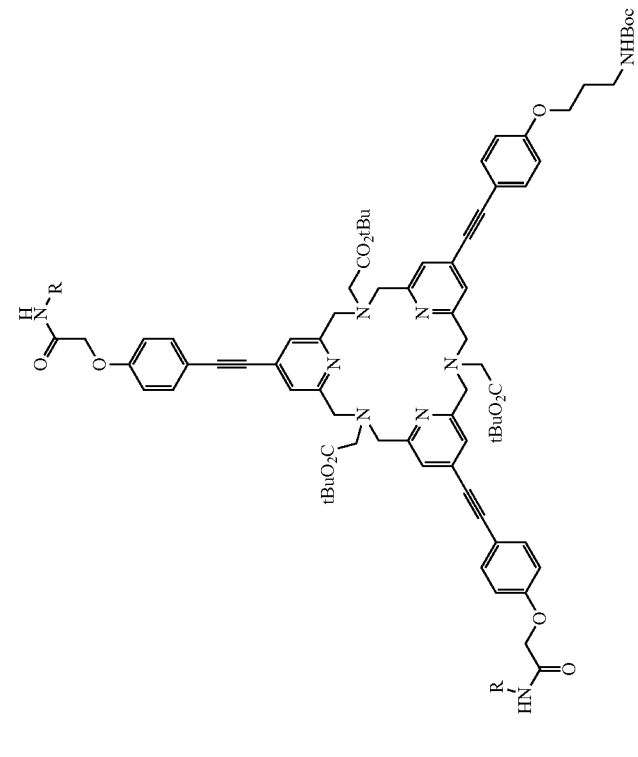
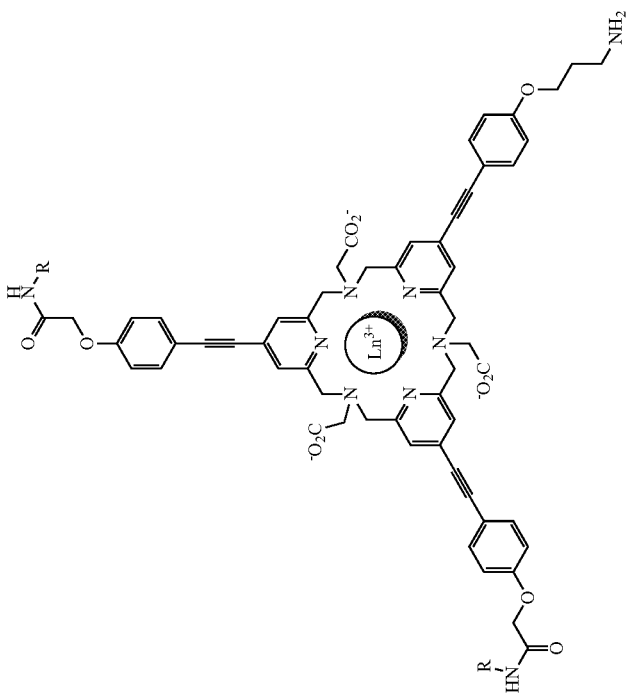

By using an analogous strategy, the mono-antenna and di-antennae pyridinophane complexes may be prepared. The synthesis schemes are described below.

Synthesis of mono-antenna (pyridinyl-acetylene-4-O-phenyl) systems

The synthesis of these systems is described in schemes 5-7.

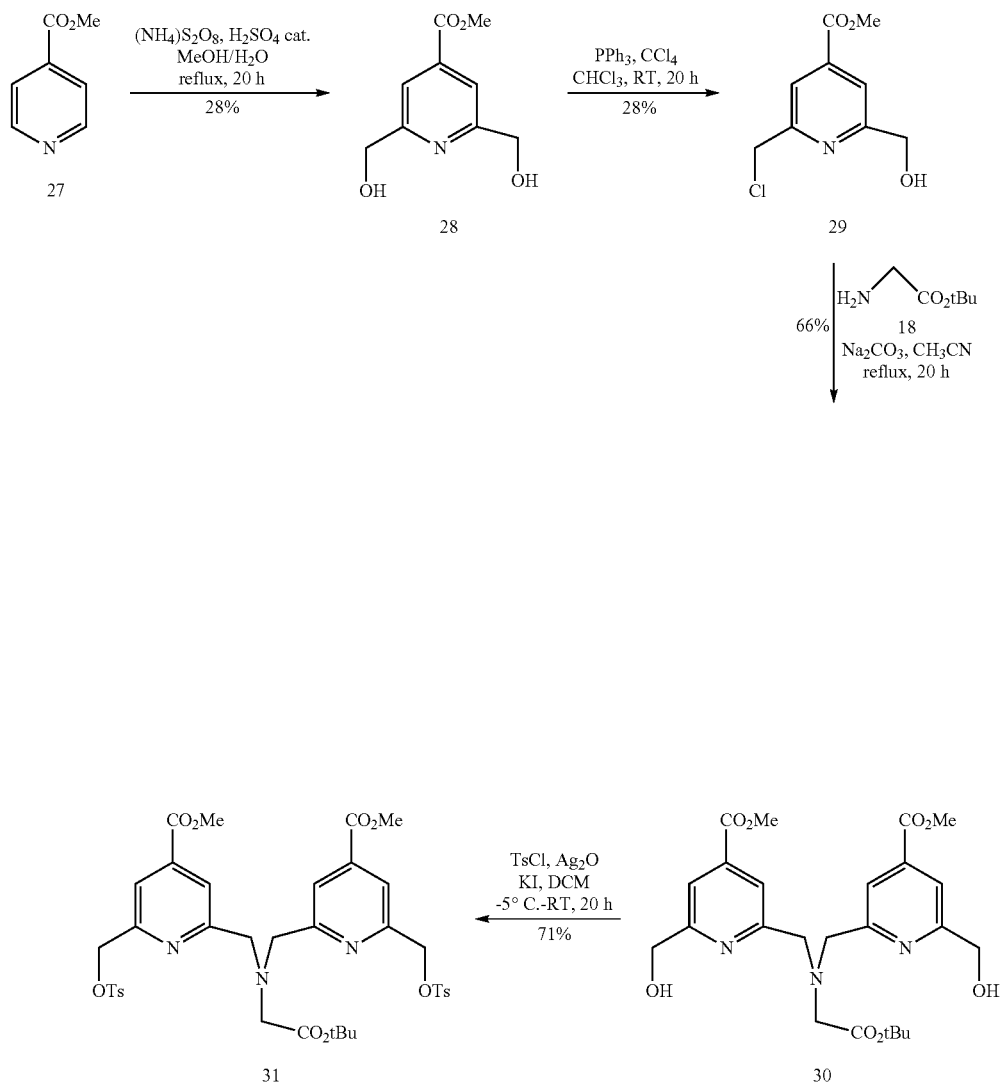

Scheme 5

The methyl isonicotinate treated under oxidizing conditions results in the diol 28 with a yield of 28%. Although this yield is mediocre, this reaction makes it possible to simultaneously introduce two hydroxymethylene groups at position 2 and 6 of the pyridinyl ring, in a single step. The monochlorination of the diol makes it possible to obtain the compound 29 which then reacts with the compound 18 resulting in the dipyridinyl backbone 30. The alcohol functions are activated in tosylate form then the macrocyclization step is carried out as described previously on the tri-antennae systems and results in the key intermediate 32.

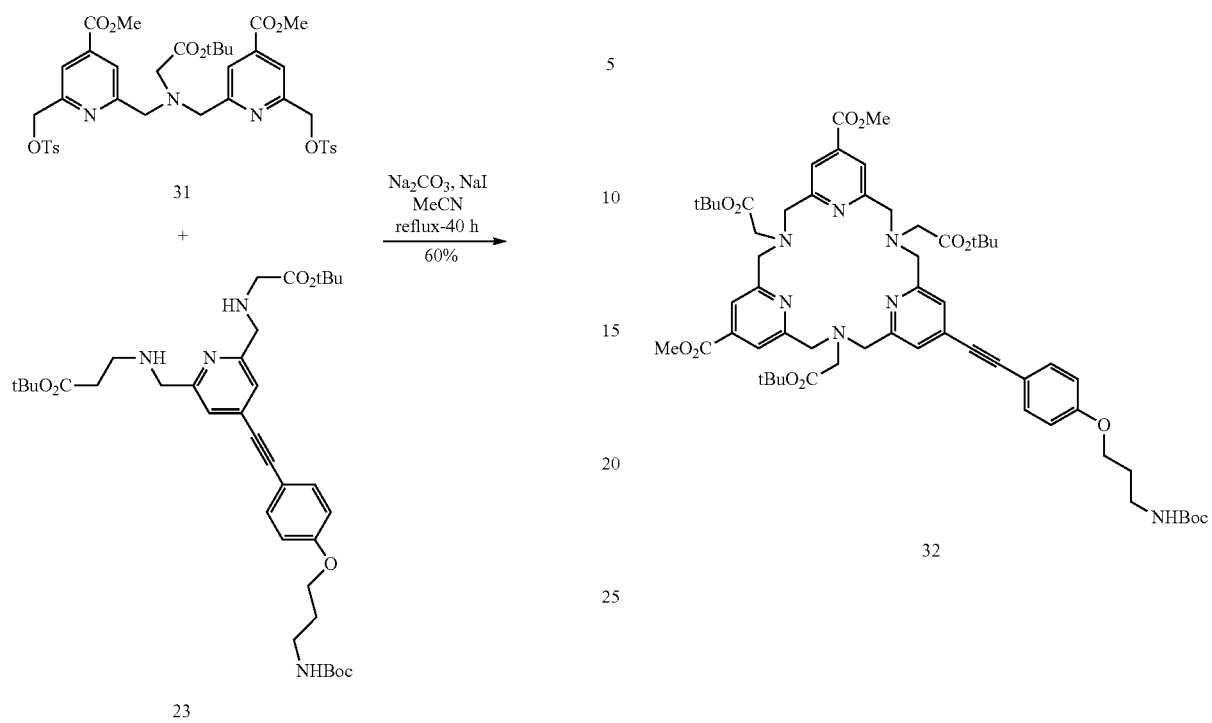

Scheme 7
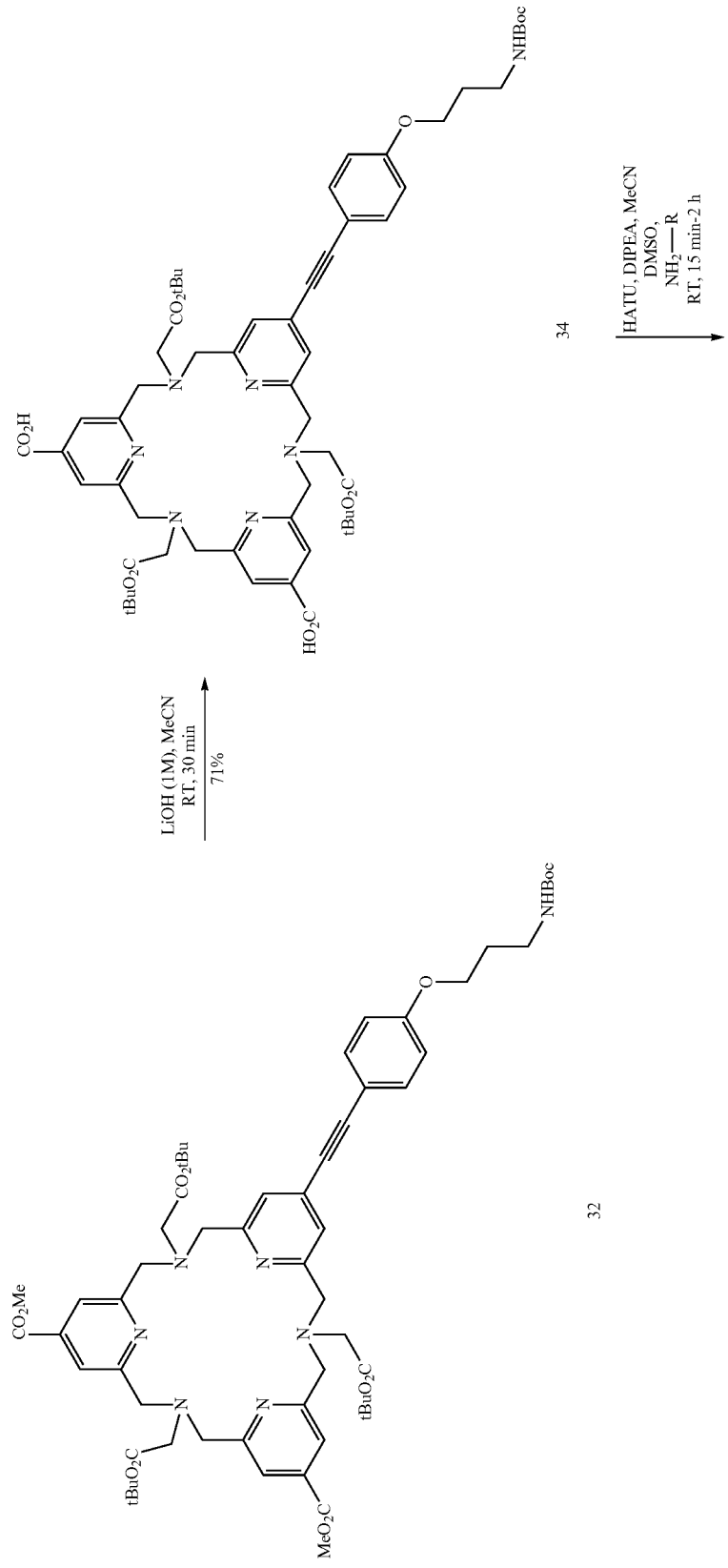

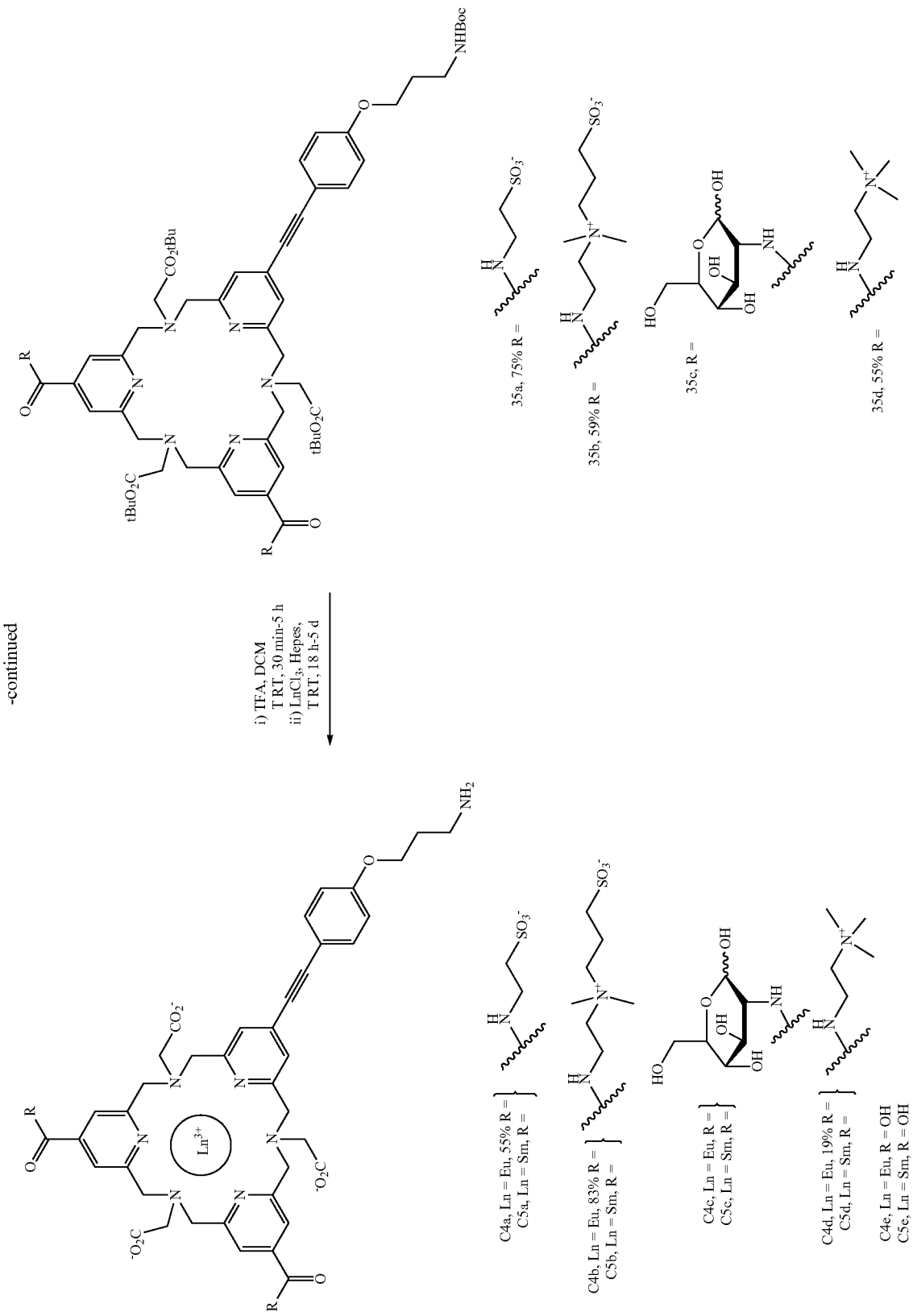

The hydrolysis of the two methyl ester functions results in the diacid compound 34 onto which two water-solubilizing functions (of anionic 35a, zwitterionic 35b, neutral 35c, or cationic 35d nature) are grafted. The deprotection of the butyl esters and of the Boc protecting group is carried out in the presence of pure trifluoroacetic acid. The lanthanide atom is complexed in the cavity of the ligand when the latter is treated in a HEPES buffer in the presence of an aqueous solution of europium or samarium chloride.

Synthesis of di-antennae
(pyridinyl-acetylene-4-O-phenyl) systems

The synthesis of these systems is described in schemes 8-10.

As regards the di-antennae systems, the synthesis begins with an esterification reaction on the chelidamic acid 36 which is commercially available (procedure described in Inorganic Chemistry 2000, 39, 4678). The arm acting as a link between the complex and the biomolecule is introduced at this level of the synthesis using a Mitsunobu reaction (procedure described in Organic Biomolecular Chemistry 2012, 10, 9183). The diol 39 is obtained by a double reduction reaction using sodium borohydride in ethanol, then the latter is subsequently activated in ditosylated form (procedure described in Organic & Biomolecular Chemistry 2012, 10, 9183). The synthon 42 is prepared as above (tri-antennae system) by condensing 19 with 40 (prepared according to the procedure described in Organic & Biomolecular Chemistry 2012, 10, 9183) then by deprotecting the

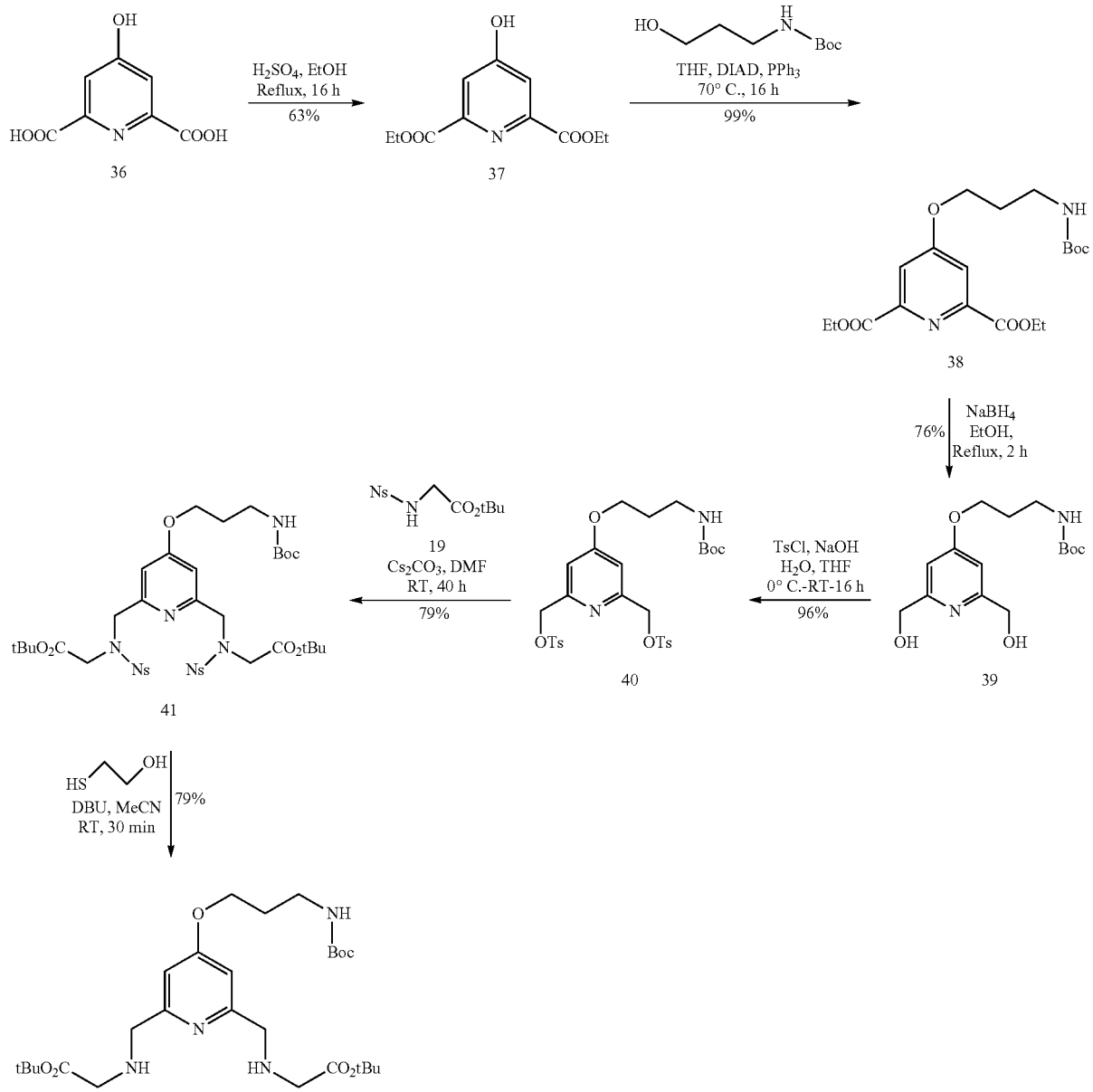

Scheme 8 nosyl protecting groups. The two compounds 12 and 42 are used for the preparation of the key intermediate 43 constituting the base of the di-antennae systems (schemes 9 and 10).

Scheme 9
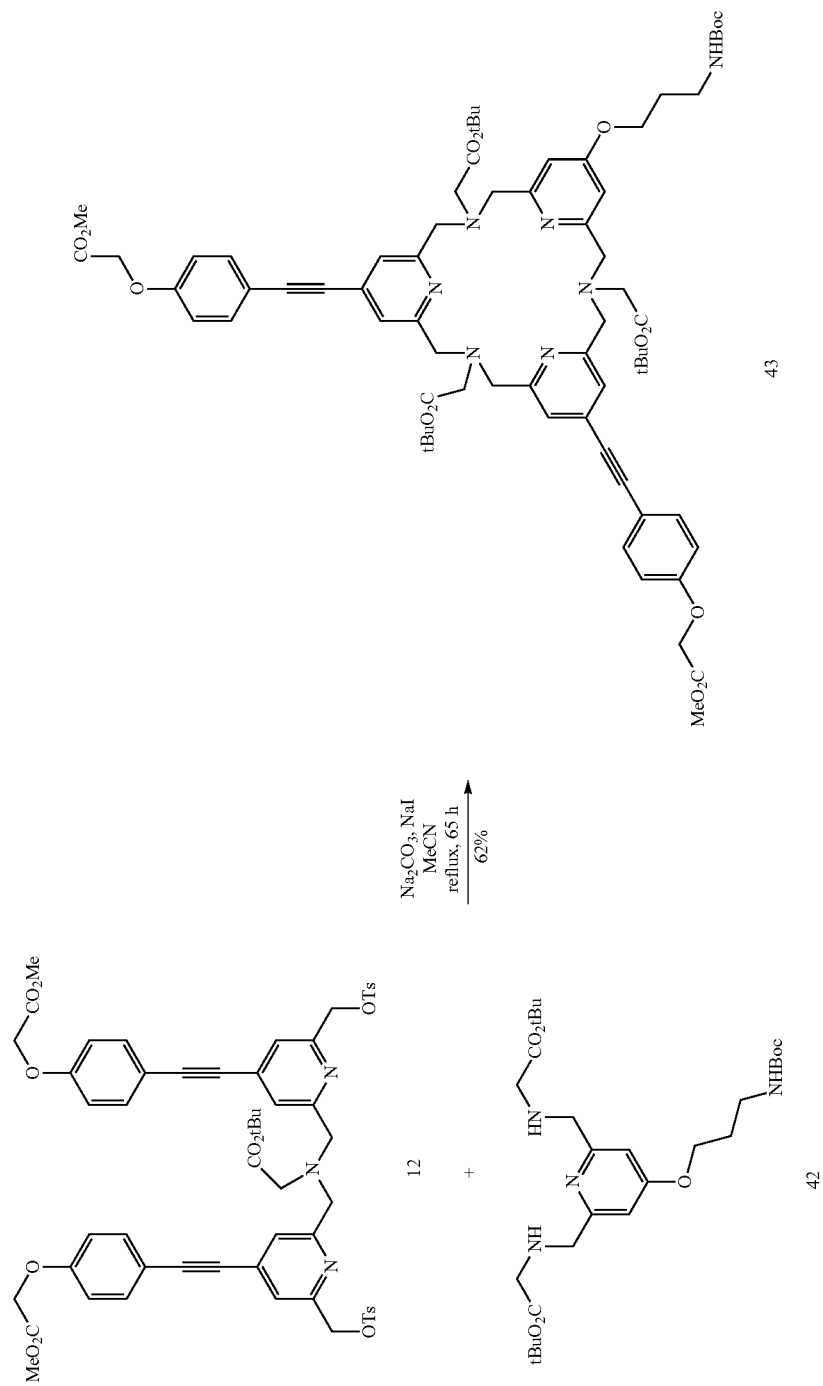

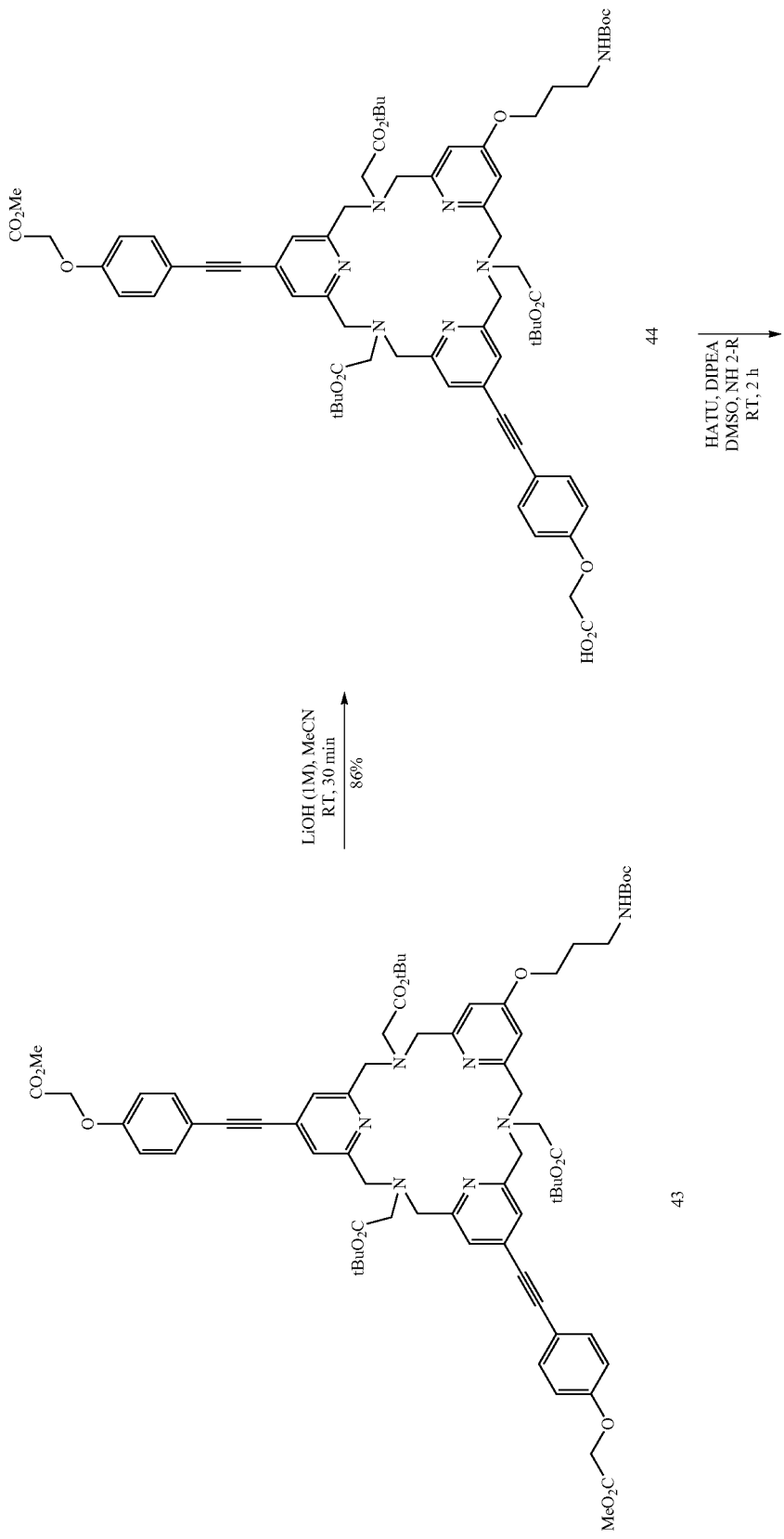

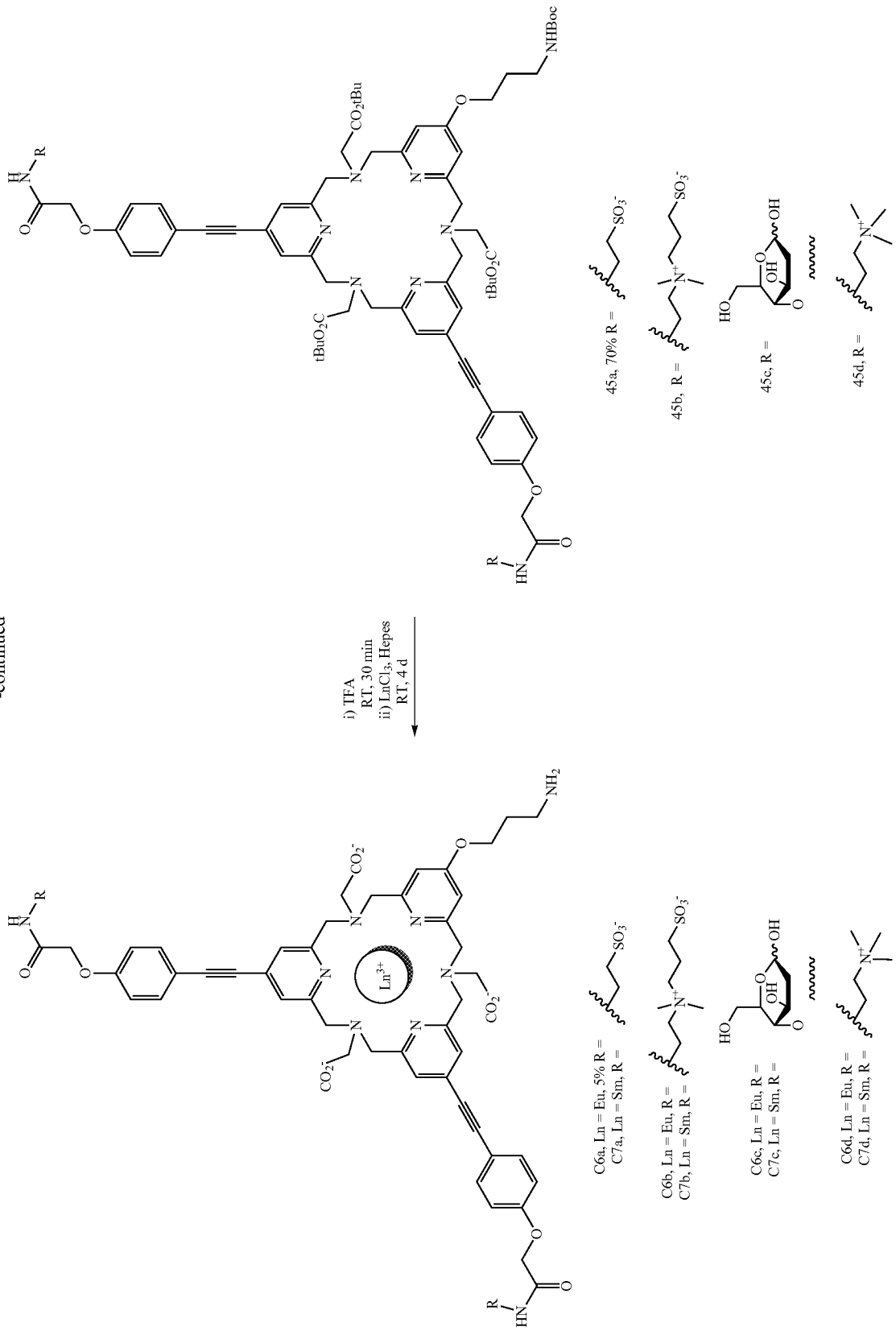

The ester functions are hydrolyzed and the water-solubilizing functions are introduced as above but this time on the antennae directly. The remainder of the synthesis is identical to that which was described for the tri-antennae and mono-antenna systems.

These fluorescent probes may be activated by introducing conventional functions: NHS ester, azido, maleimide or isothiocyanate. One example describes the activation in maleimide form enabling the bioconjugation to proteins, or to secondary messengers of cAMP type. Schemes 11 and 12 describe two examples of these molecules.

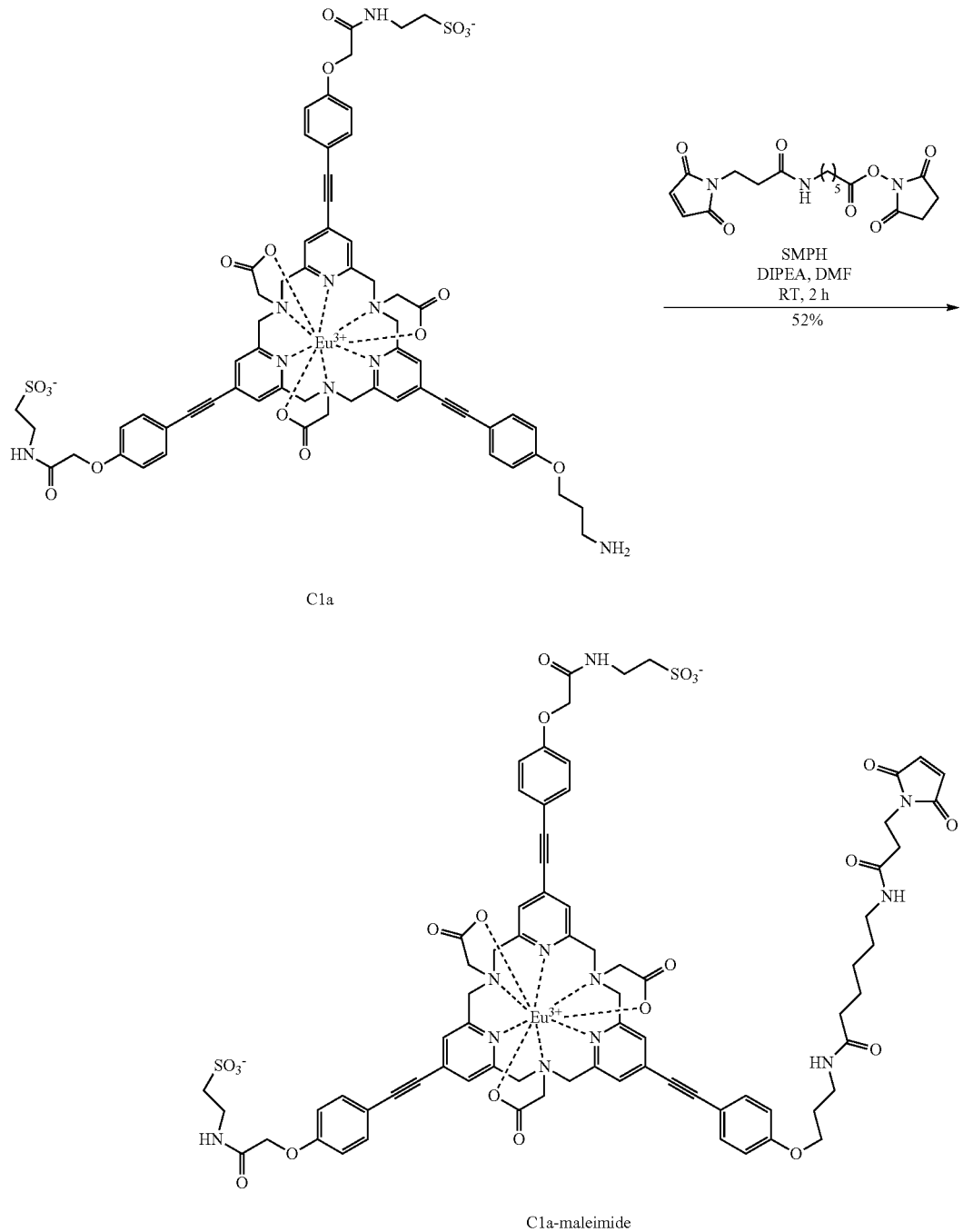

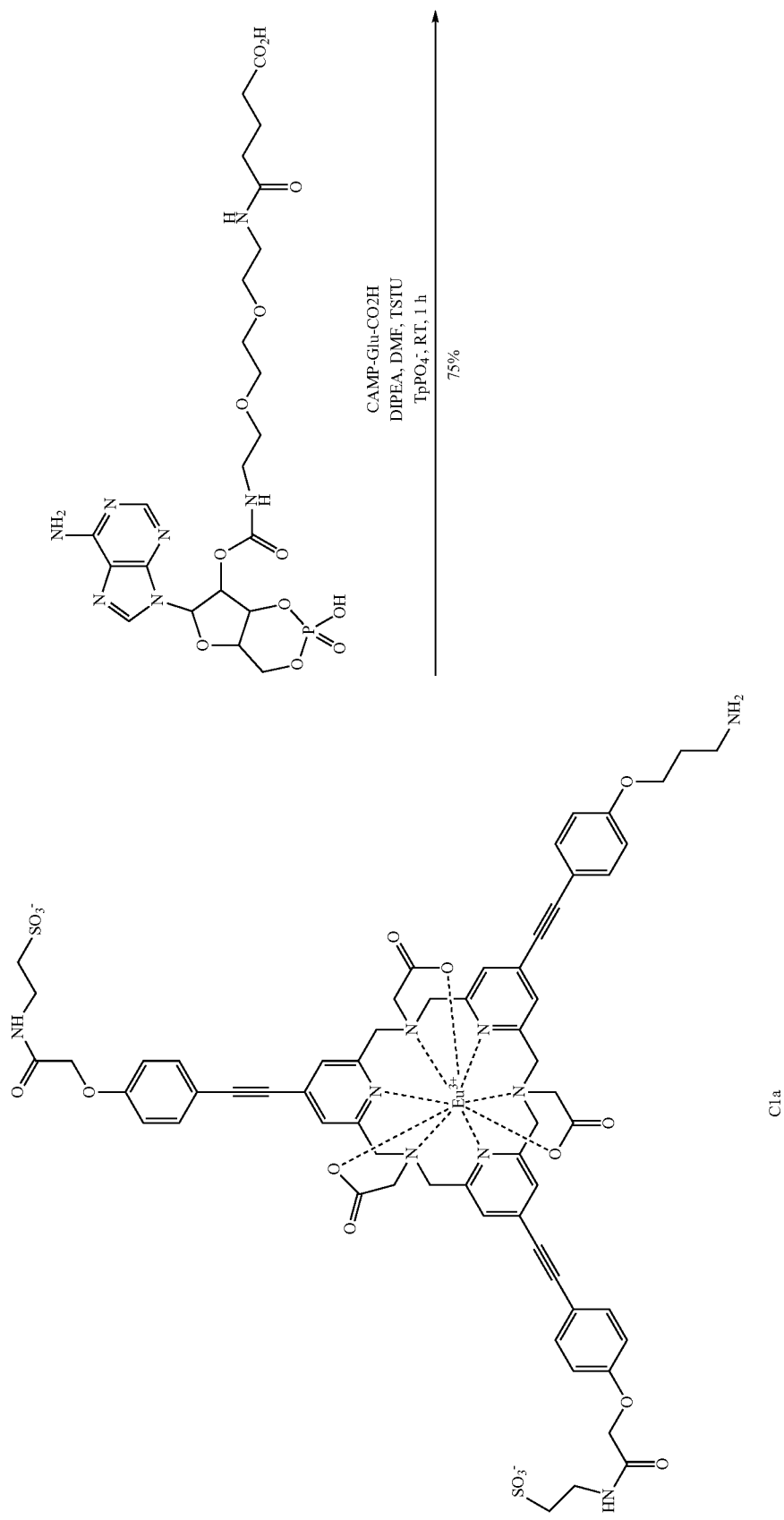
Scheme 12

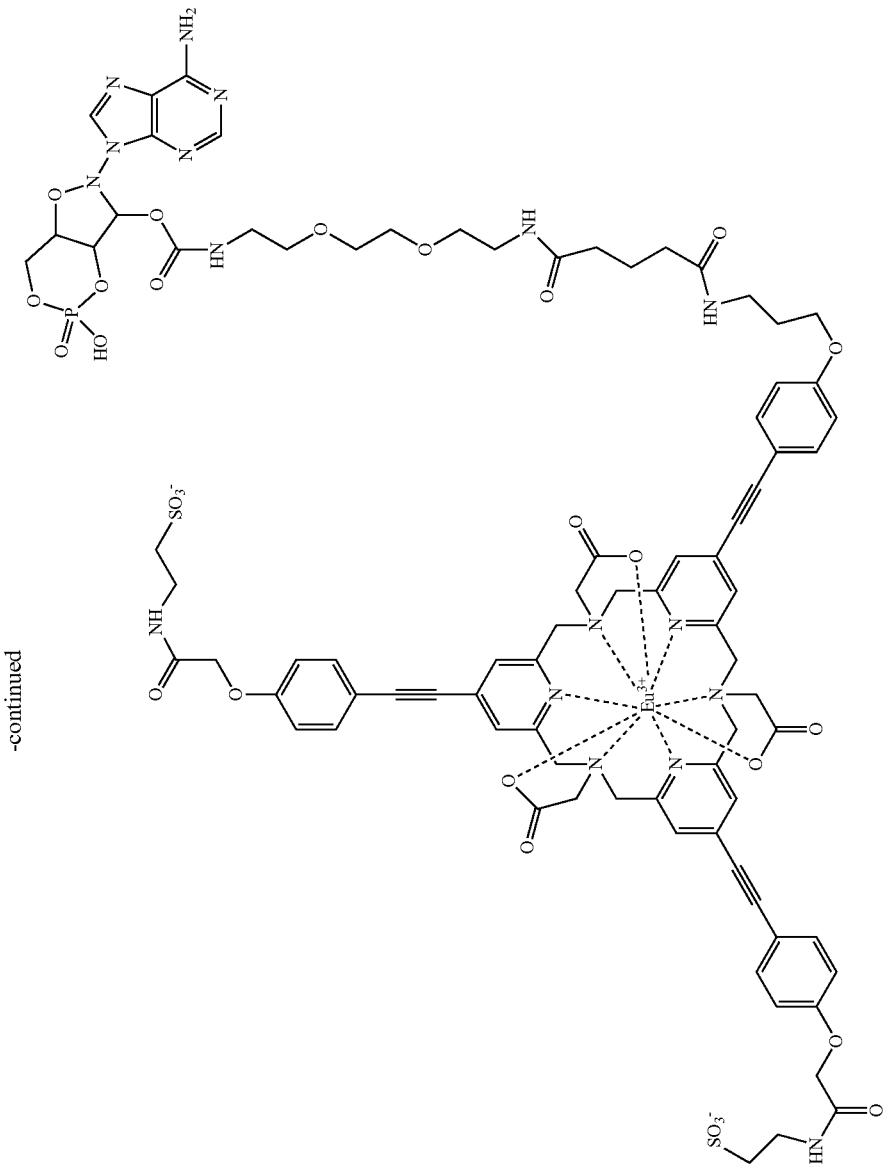

Synthesis of tri-antennae (pyridinyl-2,4,5-O-phenyl) systems

Pyridinyl trimethoxyphenyl systems are also chromophores compatible with FRET technology. Schemes 13-15 indicate the methodology which was followed to obtain the corresponding complexes (C8-C10 series). The procedures are identical to those described above or are available in the literature. The details are given in the experimental section.

Scheme 13

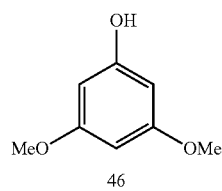
46

DCM, DMAP
TEA, RT, 5 h
99%

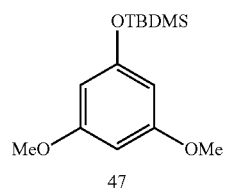
47

1) THF, n-BuLi
   -78° C.-RT, 5 h
2) THF,
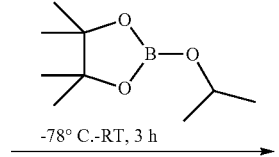
-78° C.-RT, 3 h
45%

48

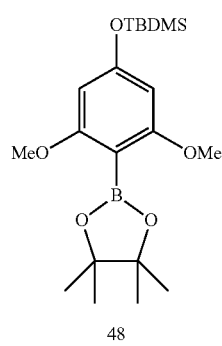
48

8
Pd(OAc)₂, SPhos
K₃PO₄, PhMe, H₂O
60° C., 17 h
80%

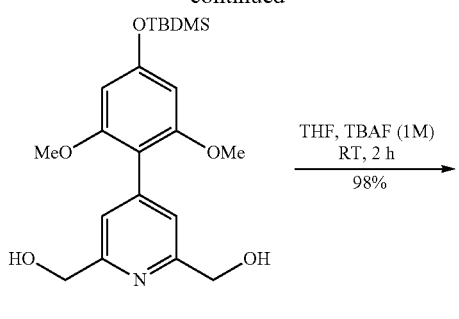
49

THF, TBAF (1M)
RT, 2 h
98%

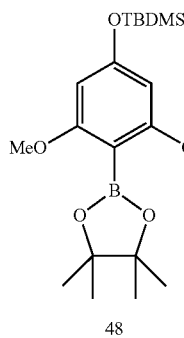
50

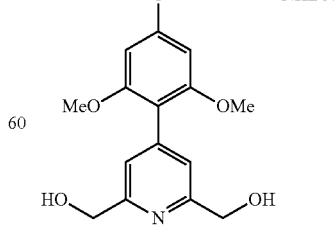
14
Cs₂CO₃, NaI
MeCN, 60° C., 24 h
85%

K₂CO₃, KI, Me₂CO
Reflux, 12 h
79%

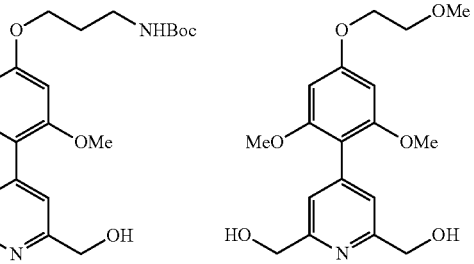

51    52

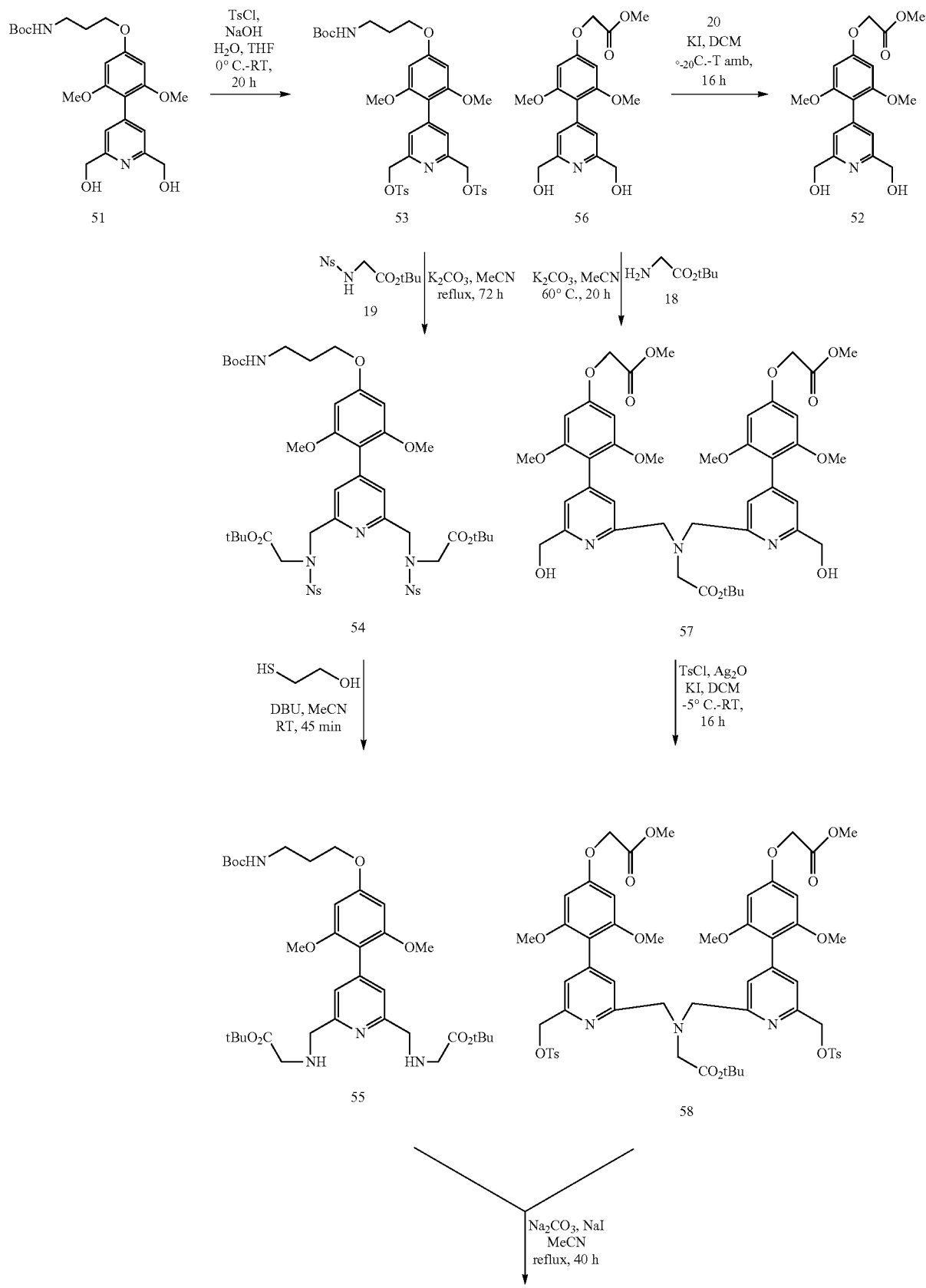

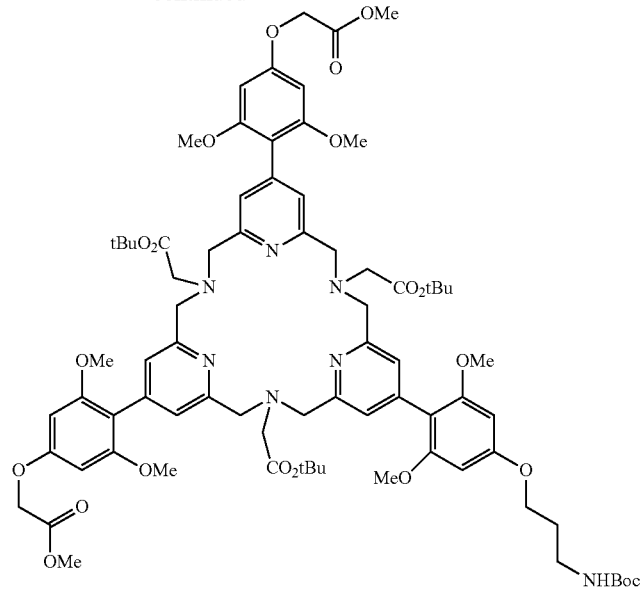

Scheme 15
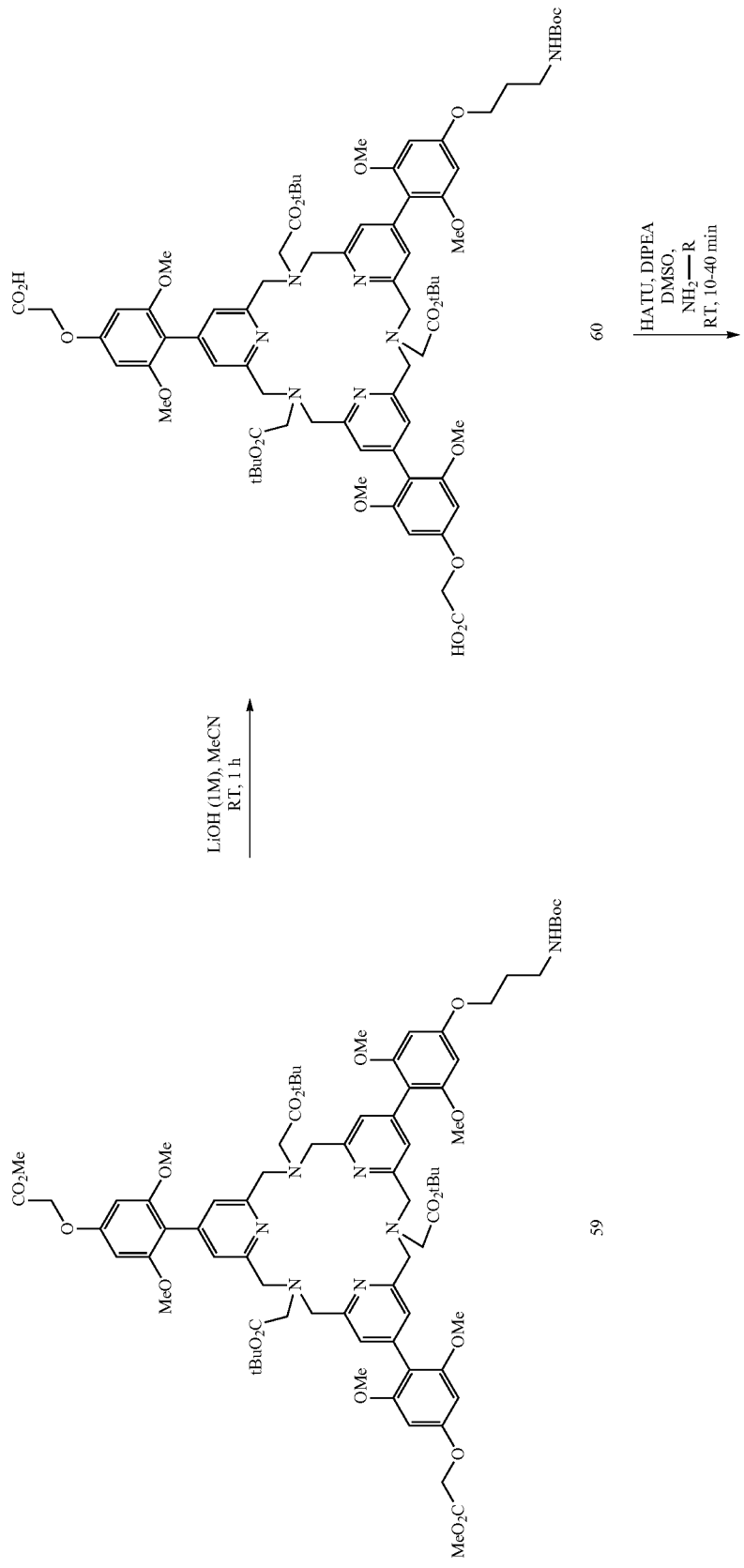

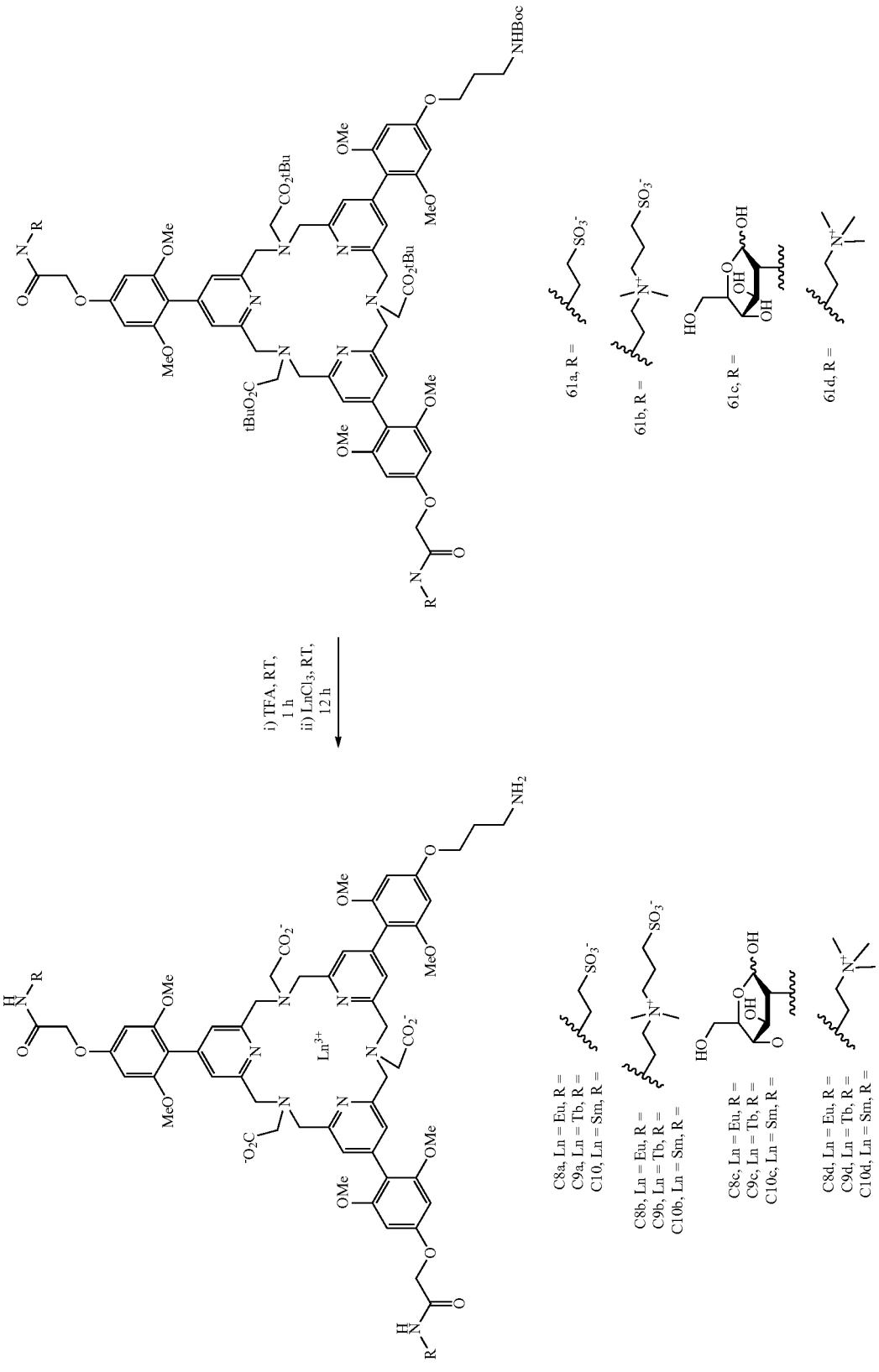

Experimental Section
General information

ABBREVIATIONS USED

Boc: tert-Butyloxycarbonyl
Boc-Osu: N-(tert-butoxycarbonyloxy)succinimide
cAMP: cyclic adenosylmonophosphate
m-CPBA: meta-chloroperbenzoic acid
d: day
DBU: 1,8-diazabicyclo[5.4.0]undec-7-ene
DCC: dicyclohexylurea
DCM: dichloromethane
δ: chemical shift
DIAD: diisopropyl azodicarboxylate
DIPEA: diisopropylethylamine
DMF: dimethylformamide
DMSO: dimethyl sulfoxide
EtOH: ethanol
ESI: electrospray ionization
h: hour
HATU: 1-[Bis(dimethylamino)methylene]-1H-1,2,3-triazolo[4,5-b]pyridinium-3-oxide hexafluorophosphate
HEPES: 4-(2-hydroxyethyl)-1-piperazineethanesulfonic acid
HPLC: high-performance liquid chromatography
HRMS: high-resolution mass spectroscopy
HTRF: Homogeneous Time Resolved Fluorescence
Hz: Hertz
MeCN: acetonitrile
MeOH: methanol
min: minute
Mops: 3-(N-morpholino)propanesulfonic acid
MP: melting point
MS: mass spectrometry
Ms: mesyl
NBS: N-bromosuccinimide
NHS: N-hydroxysuccinimide
NIS: N-iodosuccinimide
NMR: nuclear magnetic resonance
Ns: nosyl
PE: petroleum ether
PEG: polyethylene glycol
Ph: phenyl
ppm: parts per million
RT: room temperature
SMPH: succinimidyl-6-((beta-maleimidopropionamido)hexanoate
Sphos; 2-Dicyclohexylphosphino-2',6'-dimethoxybiphenyl
TEA or Et$_3$N: triethylamine
TFA: trifluoroacetic acid
THF: tetrahydrofuran
TLC: thin-layer chromatography
TMS: trimethylsilyl
TsCl: tosyl chloride
TSTU: O—(N-Succinimidyl)-1,1,3,3-tetramethyluronium tetrafluoroborate Chromatography The thin-layer chromatography techniques were performed on Merck 60 F$_{254}$ silica gel plates on a sheet of aluminum or on Merck 60 F$_{254}$ neutral aluminum oxide plates (type E) on a sheet of aluminum.

The analytical and preparative high-performance liquid chromatography (HPLC) techniques were performed on two machines:

Analytical HPLC: ThermoScientific, P4000 quaternary pump, UV 1000 detector with deuterium lamp (190-350 nm), Waters XBridge C18, 3.5 μm, 4.6×100 mm analytical column.

Preparative HPLC: Shimadzu, 2 LC-8A pumps, Varian-ProStar UV diode array detector, Waters XBridge Prep. C18, 5 μm: 19×100 mm or 50×150 mm preparative column.

The chromatography techniques on a silica column were performed on Merck 60 silica gel (0.040-0.063 mm). The chromatography techniques on an alumina column were performed on Brochmann I, activated, neutral Sigma-Aldrich aluminum oxide.

Gradient A:
Waters Xbridge C$_{18}$, 300 Å, 3.5 μm, 4.6×100 mm column, A/water 0.1% formic acid—B/acetonitrile 0.1% formic acid, t=0 min, 5% B—t=15 min 100% B—1 ml.min$^{-1}$.

Gradient B:
Waters Xbridge C$_{18}$, 5 μm, 19×100 mm column, A/water 0.1% formic acid B/acetonitrile t=0 min, 50% B—t=17 min, 100% B—20 ml.min$^{-1}$.

Gradient C:
Waters Xbridge C$_{18}$, 5 μm, 50×150 mm column, A/water 0.1% formic acid B/acetonitrile t=0 min, 15% B—t=2 min, 15% B—t=20 min, 100% B—100 ml.min$^{-1}$.

Gradient D
Waters Xbridge C$_{18}$, 5 μm, 19×100 mm column, A/water 0.1% formic acid B/acetonitrile t=0 min, 15% B—t=2 min 15% B—t=20 min 100% B—20 ml.min$^{-1}$.

Gradient E
Waters Xbridge C$_{18}$, 300 Å, 3.5 μm, 4.6×100 mm column, A/H$_2$O 5 mM ammonium acetate pH 6.5—B/acetonitrile—t=0 min 2% B—t=15 min 40% B. 1 ml.min$^{-1}$.

Gradient F
Waters Xbridge C$_{18}$, 5 μm, 50×150 mm column, A/water 25 mM triethylammonium acetate B/acetonitrile t=0 min 2% B—B—t=17 min 40% B—100 ml.min$^{-1}$.

Gradient G
Waters Xbridge C$_{18}$, 5 μm, 19×100 mm column, A/water 25 mM triethylammonium acetate B/acetonitrile t=0 min 5% B—B—t=17 min 40% B—20 ml.min$^{-1}$.

Gradient H
Waters Xbridge C$_{18}$, 300 Å, 5 μm, 10×100 mm column—water 25 mM triethylammonium acetate B/acetonitrile t=0 min 2% B—B—t=19 min 40% B—5 ml.min$^{-1}$ Gradient I
Waters Acquity C$_{18}$, 300 Å, 1.7 μm, 2.1×50 mm column—A/water 0.1% formic acid B/acetonitrile 0.1% formic acid t=0 min 5% B—t=0.2 min 5% B—t=5 min 100% B—0.6 ml.min$^{-1}$ Gradient J
Waters Xbridge C$_{18}$, 5 μm, 50×150 mm column—A/water 25 mM TEAAc pH 7 B/acetonitrile t=0 min 50% B—t=20 min 100% B—100 ml.min$^{-1}$ Gradient K
Waters Xbridge C$_{18}$, 5 μm, 50×150 mm column—A/water 25 mM TEAAc pH 7 B/acetonitrile t=0 min 15% B—t=19 min 80% B—80 ml.min$^{-1}$ Gradient L
Waters Xbridge C$_{18}$, 300 Å, 5 μm, 19×100 mm column—A/water 25 mM TEAAc pH 7 B/acetonitrile t=0 min 20% B—t=19 min 80% B—100 ml.min$^{-1}$ Gradient M
Waters Xbridge C$_{18}$, 5 μm, 50×150 mm column—A/water 25 mM TEAAc pH 7 B/acetonitrile t=0 min 2% B—t=18 min 40% B—80 ml.min$^{-1}$ Gradient N Waters Acquity $C_{18}$, 300 Å, 1.7 µm, 2.1×50 mm column—A/water 5 mM ammonium acetate pH 5 B/acetonitrile t=0 min 2% B—t=0.2 min 2% B—t=5 min 40% B—0.6 ml.min$^{-1}$ Gradient O Waters Xbridge $C_{18}$, 5 µm, 50×150 mm column—A/water 0.1% formic acid B/acetonitrile t=0 min 40% B—t=20 min 100% B—100 ml.min$^{-1}$ Spectroscopy a. Nuclear Magnetic Resonance The NMR spectra ($^1$H, $^{13}$C and $^{31}$P) were acquired using a Bruker Avance 400 MHz NanoBay spectrometer (9.4 Tesla magnet), equipped with a multinuclear BBFO measuring probe, 5 mm in diameter, of gradient Z and $^2$H lock. The chemical shifts (δ) are expressed in parts per million (ppm). The following abbreviations are used:

s: singlet, bs: broad singlet, d: doublet, t: triplet, q: quartet, m: multiplet, dd: doublet of doublets, dt: doublet of triplets, dq: doublet of quartets, ddd: doublet of doublet of doublets.

b. Mass Spectrometry

The (LC-MS) mass spectra were acquired using a single quadrupole Waters ZQ 2000 spectrometer with ESI/APCI multimode source equipped with a Waters XBridge $C_{18}$, 3.5 µm, 4.6×100 mm column.

c. High-Resolution Mass Spectrometry

The analyses were performed using a QStar Elite mass spectrometer (AppliedBiosystems SCIEX) equipped with a pneumatically-assisted atmospheric pressure ionization (API) source. The sample was ionized in positive electrospray mode under the following conditions: electrospray voltage (ISV): 5500 V; orifice voltage (OR): 20 V; spraying gas (air) pressure: 20 psi. The higher-resolution mass spectrum (MS) was obtained with a time-of-flight (TOF) analyzer. The measurement of the exact mass was performed in triplicate with an internal double calibration.

Miscellaneous

Melting point machine: the melting points were acquired using a B-540 BUCHI melting point machine.

Compound 1: commercially available.

Compound 2: the compound 2 was prepared according to the procedure described in WO 2004/094386.

Compound 3: the compound 3 was prepared according to the procedure described in the article: Journal of Medicinal Chemistry 2013, 56, 4990.

Compound 4

Anhydrous MeOH (30 ml) and anhydrous potassium carbonate (15.8 g, 114 mmol) were added successively at 0° C. to a solution of the compound 3 (20 g, 38.1 mmol) in anhydrous DCM (20 ml). The suspension was stirred at 0° C. for 15 min then at RT for 1 h then was filtered and concentrated under reduced pressure. The residue was diluted with DCM (100 ml) and then water (80 ml) was added. The organic phase was separated and the aqueous phase was extracted with DCM (2×60 ml). The organic phases were combined, dried over sodium sulfate, filtered and concentrated under reduced pressure in order to result in the compound 4 (12 g, 83%) as a slightly brown solid which was used in the remainder of the synthesis without additional purification. $^1$H NMR (CDCl$_3$, 400 MHz) δ 7.45 (d, J=8 Hz, 2H), 6.86 (d, J=8 Hz, 2H), 4.65 (s, 2H), 3.82 (s, 3H), 3.03 (s, 1H); $^{13}$C NMR (CDCl$_3$, 100 MHz) δ 168.9, 158.0, 133.6, 115.4, 114.6, 83.3, 76.3, 65.1, 52.3. LRMS (ESI+): calculated for $C_{11}H_{11}O_3$ [M+H]$^+$, m/z 191.07, found 191.70.

Compound 5: commercially available.

Compound 6: the compound 6 was prepared according to the procedure described in the article: Tetrahedron 2005, 61, 1755.

Compound 7: the compound 7 was prepared according to the procedure described in the article: Tetrahedron 2008, 64, 399.

Compound 8: the compound 8 was prepared according to the procedure described in the article: European Journal of Organic Chemistry 2002, 21, 3680.

Compound 9

Silver oxide (3.93 g, 17.0 mmol), potassium iodide (0.37 g, 2.2 mmol) then, in small portions, TsCl (2.37 g, 12.5 mmol) were added to a suspension of the compound 8 (3 g, 11.3 mmol) in anhydrous DCM (50 ml) cooled to −20° C. The mixture was stirred at RT for 16 h then filtered over Celite. The filtrate was concentrated under reduced pressure and the residual oil was purified by silica column chromatography using DCM as eluent to yield a white solid corresponding to the compound 9 (2.1 g, 44%). Melting pt: 97-98° C. $^1$H NMR (CDCl$_3$, 400 MHz) δ 7.84 (d, J=8.4 Hz, 2H), 7.64 (s, 1H), 7.62 (s, 1H), 7.38 (d, J=8.4 Hz, 2H), 5.10 (s, 2H), 4.67 (s, 2H), 3.20 (bs, 1H), 2.48 (s, 3H); $^{13}$C NMR (CDCl$_3$, 100 MHz) δ 160.0, 153.4, 145.4, 132.6, 130.0, 129.4, 129.3, 128.0, 106.9, 70.5, 63.4, 21.7. HRMS (ESI+): calculated for $C_{14}H_{15}NO_4IS$ [M+H]$^+$, m/z 419.9766, found 419.9759.

Compound 10

Anhydrous potassium carbonate (1.88 g, 13.6 mmol) was added to a suspension of tert-butyl glycinate hydrochloride (0.76 g, 4.5 mmol) in anhydrous MeCN (76 ml) and this mixture was heated at 55° C. for 30 min then cooled to RT. The compound 9 (4.0 g, 9 mmol) was added to this suspension then the mixture was heated at 60° C. for 20 h. When the mixture came back to RT, the mixture was filtered and the filtrate was concentrated under reduced pressure and the residue was purified by silica column chromatography using an AcOEt—MeOH solvent gradient of 97/3 up to 90/10 in increments of 1% to yield the compound 10 (2.5 g, 90%) in the form of a foam. $^1$H NMR (CDCl$_3$, 400 MHz) δ 7.79 (s, 2H), 7.53 (s, 2H), 4.70 (s, 4H), 3.96 (s, 4H), 3.86 (bs, 2H), 3.40 (s, 2H), 1.53 (s, 9H); $^{13}$C NMR (CDCl$_3$, 100 MHz) δ 170.1, 159.6, 158.8, 131.0, 128.3, 106.8, 81.6, 63.6, 59.2, 56.7, 38.2. HRMS (ESI+): calculated for $C_{20}H_{26}N_3O_4I$ [M+H]$^+$, m/z 626.0013, found 626.0015.

Compound 11

A solution of compound 10 (1.64 g, 2.62 mmol) and of compound 4 (1.5 g, 7.87 mmol) in a THF (7.5 ml) and TEA (7.5 ml) mixture was degassed by a stream of argon for 15 min. Then 1,1'-bis(diphenylphosphino)ferrocene]dichloropalladium(II) (0.64 g, 0.78 mmol) and copper iodide (0.3 g, 1.57 mmol) were added to this mixture. This mixture was irradiated under microwaves (100 W) for 30 min then cooled to RT and lastly filtered over a bed of Celite. The filtrate was concentrated under reduced pressure and the residue was purified by silica column chromatography using a DCM/AcOEt/MeOH solvent gradient of 1/0/0, 5/5/0, 0/1/0 up to 0/9/1 in increments of 5% to yield the desired compound 11 (1.39 g, 71%). $^1$H NMR (CDCl$_3$, 400 MHz) δ 7.51 (s, 2H), 7.48 (d, J=8.7 Hz, 4H), 7.19 (s, 2H), 6.87 (d, J=8.7 Hz, 4H), 4.75 (s, 4H), 4.68 (s, 4H), 4.16 (bs, 2H), 4.03 (s, 4H), 3.84 (s, 6H), 3.43 (s, 2H), 1.53 (s, 9H); $^{13}$C NMR (CDCl$_3$, 100 MHz) δ 170.4, 168.9, 158.5, 158.3, 158.0, 133.6, 132.6, 123.7, 120.5, 115.3, 114.7, 93.6, 86.2, 81.4, 65.1, 63.9, 59.5, 56.4, 52.3, 28.2. HRMS (ESI+): calculated for $C_{42}H_{44}N_3O_{10}$ [M+H]$^+$, m/z 750.3027, found 750.3022.

Compound 12

Potassium iodide (22 mg, 0.14 mmol) and silver oxide (231 mg, 1 mmol) were added to a solution of diol 11 (250 mg, 0.33 mmol) in DCM (8 ml). TsCl (190 mg, 1 mmol) was added in one go to this mixture cooled to −5° C. The mixture was then stirred at RT for 16 h. The progression of the reaction was monitored by TLC. After this period, the solvent was removed under pressure and the residue was purified by silica column chromatography using a DCM-MeOH eluent gradient of 99/1 up to 98/2 in increments of 0.2% to yield a beige oil (300 mg, 88%). $^1$H NMR (CDCl$_3$; 300 MHz) δ 1.46 (s, 9H); 2.4 (s, 6H), 3.32 (s, 2H), 3.80 (s, 6H), 3.87 (s, 4H), 4.65 (s, 4H), 5.07 (s, 4H), 6.83 (d, J=8.9 Hz, 4H), 7.28 (s, 2H), 7.29 (d, J=8.3 Hz, 4H), 7.44 (d, J=8.9 Hz, 4H), 7.52 (s, 2H), 7.79 (d, J=8.3 Hz, 4H). $^{13}$C NMR (CDCl$_3$; 75 MHz) δ 170.0, 168.8, 159.0, 158.3, 153.1, 145.0, 133.5, 133.0, 132.6, 129.8, 128.0, 124.2, 121.6, 115.1, 114.7, 94.1, 85.9, 81.2, 71.3, 65.0, 59.5, 56.0, 52.3, 28.1, 21.5. HRMS (ESI+): calculated for $C_{56}H_{56}N_3O_{14}S_2$ [M+H]$^+$, m/z 1058.3204, found 1058.3241.

Compound 13: commercially available.

Compound 14: commercially available.

Compound 15: the compound 15 was prepared according to the procedure described in the article: Organic Letters 2006, 8, 4251.

Compound 16: the compound 16 was prepared according to the procedure described in the article: Organic Letters. 2006, 8, 4251.

Compound 17: the compound 17 was prepared according to the procedure described in application WO 2014/111661.

Compound 18: commercially available.

Compound 19: the compound 19 was prepared according to the procedure described in the article: Organic Letters 2007, 9, 1635.

Compound 20

An aqueous solution of sodium hydroxide (1.36 g, 34 mmol dissolved in 10 ml of water) was added at RT to a solution of compound 8 (3.0 g, 11.3 mmol) in THF (10 ml). A solution of TsCl (6.47 g, 34 mmol) in THF (10 ml) was added to this mixture cooled to 0° C. and was stirred for 20 h at RT. DCM (100 ml) and a saturated solution of brine (50 ml) were added to this suspension. After decantation, the aqueous phase was extracted by DCM (2×100 ml). The organic phases were combined, dried over sodium sulfate, filtered and concentrated under reduced pressure. The crude product was purified by silica column chromatography with a cyclohexane/DCM eluent gradient of 50/50 up to 0/100 to yield the compound 20 (5.41 g, 84%) as a white solid. Melting pt.: 143.5-144.5° C. $^1$H NMR (CDCl$_3$, 400 MHz) δ 7.81 (d, J=8.2 Hz, 4H), 7.64 (s, 2H), 7.36 (d, J=8.2 Hz, 4H), 5.01 (s, 4H), 2.47 (s, 6H); $^{13}$C NMR (CDCl$_3$, 100 MHz) δ 154.1, 145.3, 132.6, 130.3, 130.0, 128.0, 106.9, 70.38, 21.72. HRMS (ESI+): calculated for $C_{21}H_{21}NO_6IS_2$ [M+H]$^+$, m/z 573.9855, found 573.9854.

Compound 21

Sodium carbonate (2.77 g, 26.2 mmol) was added to a solution of compound 19 (1.83 g, 5.75 mmol) in anhydrous MeCN (36 ml) then the suspension was stirred at 80° C. for 1 h. The compound 20 (1.5 g, 2.62 mmol) was added to this suspension cooled to RT and the mixture was stirred at 80° C. for 72 h. After this period, the reaction mixture was cooled to RT, filtered and the filtrate was concentrated under reduced pressure. The residue was purified by silica column chromatography using an AcOEt/MeOH eluent gradient of 98/2 up to 95/5 in increments of 0.5% to yield the compound 21 (2.0 g, 89%) as a yellowish oil. $^1$H NMR (CDCl$_3$, 400 MHz) δ 8.08 (dd, J=7.6 Hz, 1.6 Hz, 2H), 7.75-7.66 (m, 6H), 7.60 (s, 2H), 4.63 (s, 4H), 4.15 (s, 4H), 1.39 (s, 18H); $^{13}$C NMR (CDCl$_3$, 100 MHz) δ 167.3, 156.3, 147.7, 133.7, 133.5, 131.7, 130.8, 130.4, 124.2, 107.3, 82.6, 52.8, 49.2, 28.0. HRMS (ESI+): calculated for $C_{31}H_{37}N_5O_{12}IS_2$ [M+H]$^+$, m/z 862.0925, found 862.0927.

Compound 22

A solution of compound 17 (2.58 g, 9.4 mmol) and of compound 21 (8.2 g, 8.54 mmol) in a mixture of TEA (42 ml) and of anhydrous THF (42 ml) was degassed under a stream of argon for 15 min. Then 1,1'-bis(diphenylphosphino)ferrocene]dichloropalladium(II) (1.39 g, 1.70 mmol) and copper iodide (0.49 g, 1.57 mmol) were added to this mixture and it was heated at 60° C. with stirring for 20 h. This mixture was cooled to RT and filtered over a bed of Celite. The filtrate was concentrated under reduced pressure and the crude product was purified by silica column chromatography using a cyclohexane/DCM/AcOEt eluent gradient of 5/2/3 up to 2/5/3 to yield the compound 22 (4.9 g, 57%) as a yellow foam. $^1$H NMR (CDCl$_3$, 400 MHz) δ 8.10 (dd, J=7.6 Hz, 1.7 Hz, 2H), 7.75-7-65 (m, 6H), 7.49 (d, J=8.7 Hz, 2H), 7.32 (s, 2H), 6.92 (d, J=8.7 Hz, 2H), 4.76 (bs, 1H), 4.68 (s, 4H), 4.17 (s, 4H), 4.08 (t, J=6.0 Hz, 2H), 3.36 (m, 2H), 2.03 (m, 2H), 1.47 (s, 9H), 1.38 (s, 18H); $^{13}$C NMR (CDCl$_3$, 100 MHz) δ 167.4, 159.7, 156.0, 155.8, 147.9, 133.8, 133.6, 133.6, 131.8, 130.8, 124.2, 122.7, 114.7, 113.8, 95.3, 85.5, 82.4, 79.3, 65.9, 53.0, 49.2, 37.8, 29.5, 28.4, 27.9. HRMS (ESI+): calculated for $C_{47}H_{57}N_6O_{15}S_2$ [M+H]$^+$, m/z 1009.3323 found 1009.3322.

Compound 23

2-Mercaptoethanol (76 μl, 1.09 mmol) and 1,8-diazabicyclo[5.4.0]undec-7-ene (67 μl, 0.445 mol) were added, with stirring, to a solution of compound 22 (0.1 g, 0.099 mmol) in MeCN (4.3 ml). The reaction was stirred for 45 min at RT. The progression of the reaction was monitored by TLC. After this period, the reaction was complete. The solvent was removed under reduced pressure and the crude product was purified by silica column chromatography using an AcOEt/MeOH mixture (98/02 then 96/04) as eluent to yield the compound 23 (35 mg, 55%) as a beige oil. $^1$H NMR (CDCl$_3$, 300 MHz) δ 1.46 (s, 9H), 1.49 (s, 18H), 2.01 (m, 2H), 3.33 (m, 2H), 3.40 (s, 4H), 3.94 (s, 4H), 4.06 (m, 2H), 6.89 (d, J=8.8 Hz, 2H); 7.32 (s, 2H); 7.48 (d, J=8.8 Hz, 2H). $^{13}$C NMR (CDCl$_3$, 75 MHz) δ 171.3, 159.4, 159.0, 156.0, 133.4, 132.6, 122.0, 114.6, 114.3, 93.7, 86.1, 81.2, 79.2, 65.8, 54.3, 51.1, 37.8, 29.5, 28.3, 28.1, HRMS (ESI+): calculated for $C_{35}H_{51}N_4O_7$ [M+H]$^+$, m/z 639.3758, found 639.3784.

Compound 24

Sodium carbonate (312 mg, 2.95 mmol) and sodium iodide (4.4 mg, 0.0295 mmol) were added to a solution of ditosylated derivative 12 (312 mg, 0.295 mmol) and derivative 23 (188 mg, 0.295 mmol) in anhydrous MeCN (140 ml). The suspension was stirred at reflux for 40 h. The progression of the reaction was monitored by TLC. After this period, the reaction was complete. The reaction mixture was cooled to RT, filtered and the filtrate was concentrated under reduced pressure. The residue was purified by alumina column chromatography using a DCM/MeOH mixture (98/02 then 97/03) as eluent to yield the compound 24 (297 mg, 74%) as a beige oil. $^1$H NMR (CDCl$_3$, 300 MHz) δ 1.47 (s, 9H), 1.52 (s, 27H), 2.02 (m, 2H), 3.37 (m, 2H), 3.43 (s, 4H), 3.45 (s, 2H), 3.84 (s, 6H), 3.90 (m, 12H), 4.02 (m, 2H), 4.62 (s, 4H), 6.69 (m, 6H), 7.22 (m, 4H), 7.25 (s, 2H), 7.35 (m, 6H). $^{13}$C NMR (CDCl$_3$, 75 MHz) δ 170.6, 168.9, 159.1, 158.49, 158.45, 158.4, 157.8, 156.0, 133.43, 133.41, 132.0, 131.7, 123.0, 122.97, 122.8, 115.8, 114.6, 114.4, 114.3, 92.9, 92.4, 86.6, 86.4, 81.1, 79.2, 65.7, 65.0, 60.3, 60.2, 60.1, 59.0, 58.7, 52.3, 37.7, 29.4, 28.4, 28.2. HRMS (ESI+): calculated for $C_{77}H_{90}N_7O_{15}$ [M+H]$^+$, m/z 1352.6495, found 1352.6521.

Compound 25

A 1M aqueous solution of lithium hydroxide (156 µl, 156 µmol) was added to a solution of compound 24 (21.1 mg, 15.6 µmol) in MeCN (2.11 ml). The solution was stirred at RT for 1 h. The progression of the reaction was monitored by LC-MS (gradient A). After this period, the reaction was complete. The solution was directly purified by preparative HPLC (gradient B) and resulted in the compound 25 (9.4 mg, 45%) identified as the desired compound. HRMS (ESI+): calculated for $C_{75}H_{86}N_7O_{15}$ [M+H]$^+$, m/z 1324.6182, found 1324.6185. HPLC (gradient A) Rt=13.95 min.

Compound 26a

Taurine (12.85 mg, 102.7 µmol), DIPEA (26.4 µl, 19.9 mg, 154 µmol) and lastly HATU (39 mg, 102.7 µmol) were added to a solution of the compound 25 (34 mg, 25.7 µmol) in anhydrous DMSO (1275 µl). The solution was stirred at RT for 40 min. The progression of the reaction was monitored by LC-MS (gradient A). After this period, the reaction was complete. The solution was directly purified by preparative HPLC (gradient C) and resulted in the compound 26a (30 mg, 76%) identified as the desired compound. HRMS (ESI+): calculated for $C_{79}H_{97}N_9O_{19}S_2$ [M+2H]$^{2+}$, m/z 769.8171, found 769.8166. HPLC (gradient A) Tr=11.33 min.

Compound 26b
3-((2-Aminoethyl)dimethylammonio)propane-1-sulfonate was prepared according to the procedure described in WO 2011/146595 and in Organic & Biomolecular Chemistry 2012, 10, 1883.

3-((2-Aminoethyl)dimethylammonio)propane-1-sulfonate (15 mg, 71.58 µmol), DIPEA (11.6 µl, 8.8 mg, 67.9 µmol) and lastly HATU (17.2 mg, 45.3 µmol) were added to a solution of the compound 25 (15 mg, 11.3 µmol) in anhydrous DMSO (562 µL). The solution was stirred at RT for 10 min. The progression of the reaction was monitored by LC-MS (gradient A). After this period, the reaction was complete. The solution was directly purified by preparative HPLC (gradient D) and resulted in the compound 26b (11.6 mg, 60%) identified as the desired compound. HRMS (ESI+): calculated for $C_{89}H_{119}N_{11}O_{19}S_2$ [M+2H]$^{2+}$, m/z 854.9062, found 854.9054. HPLC (gradient A) Rt=11.14 min.

Compound 26c
Glucosamine (9.77 mg, 45.3 µmol), DIPEA (11.6 µl, 8.8 mg, 67.9 µmol) and lastly HATU (17.2 mg, 45.3 µmol) were added to a solution of the compound 25 (15 mg, 11.3 µmol) in anhydrous DMSO (562 µL). The solution was stirred at RT for 10 min. The progression of the reaction was monitored by LC-MS (gradient A). After this period, the reaction was complete. The solution was directly purified by preparative HPLC (gradient D) and resulted in the compound 26c (16.3 mg, 87%) identified as the desired compound. HRMS (ESI+): calculated for $C_{87}H_{108}N_9O_{23}$ [M+H]$^+$, m/z 1646.7558, found 1646.7558. HPLC (gradient A) Rt=11.62 min.

Compound 26d: this compound was prepared according to the same procedure as that used for the synthesis of 26a-c by selecting the corresponding amine.

Complexes C1a-C2a-C3a
TFA (500 µl) was added to the compound 26a (30 mg, 19.5 µmol). The solution was stirred at RT for 2 h. The progression of the reaction was monitored by LC-MS (gradient A). After this period, the reaction was complete. The solvent was removed under reduced pressure. The residue was divided into two parts. One part was used for the preparation of the europium complex C1a and the other part for the preparation of the terbium complex C2a.

C1a
Water (6 ml), MeCN (2 ml) and a 3 M aqueous solution of sodium hydroxide were added to the residue (22.2 mg, 18 µmol) in order to obtain a solution of pH 7. Europium chloride (26.4 mg, 72 µmol) and a 3 M aqueous solution of sodium hydroxide were added to this solution in order to obtain a solution of pH 6. The solution was stirred at RT overnight. The progression of the reaction was monitored by LC-MS (gradient E). After this period, the reaction was complete. The solution was directly purified by preparative HPLC (gradient F) and resulted in the complex C1a (9.7 mg, 38%) identified as the desired compound. HRMS (ESI+): calculated for $C_{62}H_{63}N_9O_{17}S_2Eu$ [M]$^{3+}$, m/z 473.4322, found 473.4319. HPLC (gradient E).

C2a
Water (375 µl), terbium chloride (2.24 mg, 6 µmol) and a 3 M aqueous solution of sodium hydroxide were added to the residue obtained during the first step (1.9 mg, 1.5 µmol) in order to obtain a solution of pH 6. The solution was stirred at RT overnight. The progression of the reaction was monitored by LC-MS (gradient E). After this period, the reaction was complete. The solution was directly purified by preparative HPLC (gradient G) and resulted in the complex C2a (107 µg, 5%) identified as the desired compound. HRMS (ESI+): calculated for $C_{62}H_{63}N_9O_{17}S_2Tb$ [M+3H]$^{3+}$, m/z 476.1012, found 476.1005. HPLC (gradient E).

C3a: this complex was prepared according to the same procedure as that used for the synthesis of C1a and C2a.

Complexes C1b-C2b-C3b
TFA (250 µl) was added to the compound 26b (11.6 mg, 7 µmol). The solution was stirred at RT for 2 h. The progression of the reaction was monitored by LC-MS (gradient A). After this period, the reaction was complete. The solvent was removed under reduced pressure. The residue was divided into two parts. One part was used for the preparation of the europium complex C1b and the other part for the preparation of the terbium complex C2b.

C1b
Water (3.15 ml), europium chloride (8.1 mg, 22 µmol) and a 3 M aqueous solution of sodium hydroxide were added to the residue obtained previously (7.9 mg, 5.5 µmol) in order to obtain a solution of pH 6. The solution was stirred at RT overnight. The progression of the reaction was monitored by LC-MS (gradient E). After this period, the reaction was complete. The solution was directly purified by preparative HPLC (gradient F) and resulted in the complex C1b (3.58 mg, 41%) identified as the desired compound. HRMS (ESI+): calculated for $C_{72}H_{83}N_{11}O_{17}S_2Eu$ [M+H]$^{3+}$, m/z 530.1540, found 530.1580. HPLC (gradient E) Rt=8.56 and 8.81 min (58%-42% mixture of isomers).

C2b
Water (857 µl), terbium chloride (2.24 mg, 6 µmol) and a 3 M aqueous solution of sodium hydroxide were added to the residue obtained during the first step (2.2 mg, 1.5 µmol) in order to obtain a solution of pH 6. The solution was stirred at RT overnight. The progression of the reaction was monitored by LC-MS (gradient E). After this period, the reaction was complete. The solution was directly purified by preparative HPLC (gradient G) and resulted in the complex C2b (231 µg, 10%) identified as the desired compound. HRMS (ESI+): calculated for $C_{72}H_{85}N_{11}O_{17}S_2Tb$ [M+3H]$^{3+}$, m/z 532.8273, found 532.8268. HPLC (gradient E) Rt=8.71 and 8.94 min (35%-65% mixture of isomers).

C3b: this complex was prepared according to the same procedure as that used for the synthesis of C1b and C2b.

Complexes C1c-C2c

TFA (250 µl) was added to the compound 26c (16.3 mg, 11.8 µmol). The solution was stirred at RT for 2 h. The progression of the reaction was monitored by LC-MS (gradient A). After this period, the reaction was complete. The solvent was removed under reduced pressure. Water (4 ml) and a 3 M aqueous solution of sodium hydroxide were added to the residue in order to obtain a solution of pH 7. This solution was divided into two parts. One part was used for the preparation of the europium complex C1c and the other part for the preparation of the terbium complex C2c.

C1c

Europium chloride (15.1 mg, 41.2 µmol) and a 3 M aqueous solution of sodium hydroxide were added to the solution obtained previously (16.3 mg, 11.8 µmol, 3.5 ml) in order to obtain a solution of pH 6. The solution was stirred at RT overnight. The progression of the reaction was monitored by LC-MS (gradient E). After this period, the reaction was complete. The solution was directly purified by preparative HPLC (gradient F) and resulted in the complex C1c (3.25 mg, 18%) identified as the desired compound. HRMS (ESI+): calculated for $C_{70}H_{72}N_9O_{21}Eu$ [M+]$^{2+}$, m/z 763.7027, found 763.7093. HPLC (gradient E) Rt=8.68 min.

C2c

Water (508 µl), terbium chloride (2.24 mg, 6 µmol) and a 3 M aqueous solution of sodium hydroxide were added to the solution obtained previously (2.1 mg, 1.5 µmol, 508 µL) in order to obtain a solution of pH 6. The solution was stirred at RT overnight. The progression of the reaction was monitored by LC-MS (gradient E). After this period, the reaction was complete. The solution was directly purified by preparative HPLC (gradient G) and resulted in the complex C2c (184 µg, 8%) identified as the desired compound. HRMS (ESI+): calculated for $C_{70}H_{74}N_9O_{21}Tb$ [M+2H]$^{2+}$, m/z 767.7126, found 767.7141. HPLC (gradient E) Rt=8.30 and 8.78 min (25%-75% mixture of isomers).

C3c: this complex was prepared according to the same procedure as that used for the synthesis of C1c and C2c.

C1d, C2d, C3d: these complexes were prepared according to the same procedure as that used for the synthesis of C1c and C2c.

C1a-maleimide

A solution of succinimidyl-6-((beta-maleimidopropionamido)hexanoate (0.23 mg, 600 nmol) in anhydrous DMF (50 µl) and DIPEA (0.2 µl, 155 µg, 1.2 µmol) was added to the pyridinophane complex C1a (0.56 mg, 400 nmol). The mixture was stirred at RT for 2 h. The progression of the reaction was monitored by LC-MS (gradient E) Rt=10.64 min. After this period, the reaction was complete. The solution was directly purified by preparative HPLC (gradient H) and resulted in the complex C1a-maleimide (353 µg, 210 nmol, 52%) identified as the desired compound. LRMS (ESI+): calculated for $C_{75}H_{77}N_{11}O_{21}S_2Eu$ [M+H]$^+$, m/z 1684.3933, found 1684.65. HPLC (gradient E) Rt=10.64 min.

C1a-CAMP

TSTU (0.13 mg, 440 nmol) in solution in anhydrous DMF (50 µl) and DIPEA (0.1 µl, 77.5 µg, 600 nmol) were added to the CAMP-Glu-acid (0.25 mg, 400 nmol). The mixture was stirred at RT for 1 h. The complex C1a (0.28 mg, 200 nmol) in solution in 50 mM pH 7 phosphate buffer (350 µl) was the added to this solution. The progression of the reaction was monitored by LC-MS (gradient E) Rt=9.1 min. After this period, the reaction was complete. The solution was directly purified by preparative HPLC (gradient H) and resulted in the complex C1a-CAMP (303 µg, 150 nmol, 75%) identified as the desired compound. LRMS (ESI+): calculated for $C_{84}H_{92}N_{16}O_{28}PS_2Eu$ [M+2H]$^{2+}$, m/z 1010.2329, found 1010.89. HPLC (gradient E) Rt=9.1 min.

Compound 27: commercially available.

Compound 28: the compound 28 was prepared according to the procedure described in EP-A-533131.

Compound 29

Triphenylphosphine (4.2 g, 16.1 mmol) was added to a suspension of the compound 28 (2.6 g, 13.4 mmol) in chloroform (265 ml). The mixture was stirred at RT until completely dissolved (30 min). Carbon tetrachloride (37 ml) was added to this solution and the mixture was stirred for 20 h at RT. The progression of the reaction was monitored by TLC. After this period, the reaction was complete. The solvent was removed under reduced pressure. The residue was purified by silica column chromatography using a 3/7 cyclohexane—AcOEt eluent to yield the desired compound (0.8 g, 28%) $^1$H NMR (CDCl$_3$, 300 MHz) δ 7.96 (s, 1H), 7.81 (s, 1H), 4.86 (s, 2H), 4.74 (s, 2H), 3.99 (s, 3H), 3.45 (sl 1H).

Compound 30

Sodium carbonate (1.25 g, 11.8 mmol) and the amine 18 (250 µl, 1.85 mmol) were added to a suspension of compound 29 (0.8 g, 3.7 mmol) in anhydrous MeCN (15 ml). The heterogeneous mixture was heated at reflux for 20 h then cooled to RT. A saturated aqueous solution of sodium bicarbonate (20 ml), water (15 ml) and then DCM (50 ml) were added to this mixture. The organic phase was separated and the aqueous phase was extracted with DCM (2×50 ml). The organic phases were combined, dried over sodium sulfate, filtered and concentrated under reduced pressure. The residue was purified by silica column chromatography using a DCM—MeOH eluent gradient of 97/3 up to 90/10 in increments of 1% to yield the compound 30 (0.6 g, 66%). $^1$H NMR (CDCl$_3$, 300 MHz) δ 7.97 (s, 2H), 7.67 (s, 2H), 4.82 (s, 2H), 4.81 (s, 2H), 4.12 (s, 4H), 4.02 (s, 2H), 3.98 (s, 6H), 3.43 (s, 2H), 1.53 (s, 9H).

Compound 31

Potassium iodide (7 mg, 42.5 µmol) and silver oxide (71 mg, 306 µmol) were added to a solution of diol compound 30 (50 mg, 102 µmol) in DCM (2 ml). TsCl (39 mg, 204 µmol) was added to this mixture cooled to −20° C. under an inert atmosphere. The solution was reheated to RT then stirred under an inert atmosphere for 20 h. After this period, the reaction mixture was purified directly by silica column chromatography using a 90/10 DCM—AcOEt eluent mixture to yield the ditosylated derivative 31 in the form of a colorless oil (57 mg, 71%). $^1$H NMR (CDCl$_3$): δ 1.46 (s, 9H); 2.42 (s, 6H); 3.33 (s, 2H); 3.94 (s, 6H); 3.96 (s, 4H); 5.13 (s, 4H); 7.31-7.33 (d, 4H, J=8.1 Hz); 7.75 (s, 2H); 7.80-7.83 (d, 4H, J=8.4 Hz); 7.96 (s, 2H). $^{13}$C NMR (CDCl$_3$): δ=21.7; 28.2; 52.8; 59.4; 56.1; 71.3; 81.4; 119.3; 122.1; 128.1; 129.9; 132.7; 138.9; 145.2; 154.4; 160.4; 165.3; 170.1. MS (ES+): m/z=798.5 [M+H$^+$] (100%). IR (cm$^{-1}$) v 3444, 2958, 1732, 1368, 1177.

Compound 32

The compound 23 (204 mg, 0.319 mmol), sodium carbonate (338 mg, 3.19 mmol) and sodium iodide (4.8 mg, 0.0319 mmol) were added under argon to the ditosylated compound 31 (255 mg, 0.319 mmol) in solution in anhydrous MeCN (160 ml). The suspension was stirred at reflux for 40 h. The mixture was filtered, evaporated under vacuum and the residue was purified by alumina column chromatography (100% $CH_2Cl_2$ up to 99/1 $CH_2Cl_2$/MeOH in increments of 0.5%). The fractions recovered, corresponding to a mixture of compound in free form and in the form of a sodium complex, were then redissolved in a minimum amount of DCM and washed several times with water. The desired compound 32 was obtained in the form of a yellow powder (208 mg, 60%). $R_f$=0.18 (alumina, $CH_2Cl_2$/MeOH 98/2). $^1$H NMR ($CDCl_3$, 300 MHz) δ 7.58 (s, 4H), 7.44 (d, J=8.7 Hz, 2H), 7.16 (s, 2H), 6.86 (d, J=8.7 Hz, 2H), 4.77 (s, 1H), 4.03 (t, J=6 Hz, 2H), 3.95 (s, 4H), 3.92 (s, 4H), 3.84 (s, 4H), 3.79 (s, 6H), 3.43 (s, 2H), 3.39 (s, 4H), 3.35-3.28 (m, 2H), 2.02-1.94 (m, 2H), 1.47 (s, 27H), 1.42 (s, 9H); $^{13}$C NMR ($CDCl_3$, 75 MHz) δ 170.4, 165.8, 159.6, 159.3, 158.4, 155.9, 137.6, 133.3, 131.8, 122.8, 120.5, 120.3, 114.6, 114.5, 92.8, 86.3, 81.19, 81.15, 79.2, 65.8, 60.0, 59.9, 58.9, 58.7, 52.3, 37.8, 29.5, 28.3, 28.1; HRMS (ESI+): calculated for $C_{59}H_{78}N_7O_{13}$ $[M+H]^+$, m/z 1092.5658, found 1092.5636; IR ($cm^{-1}$): v 3429, 2977, 2932, 2210, 1729, 1596, 1511, 1367, 1225, 1159.

Compound 34

In a 25 ml round-bottom flask the compound 32 (50.0 mg, 46 μmol) was dissolved in MeCN (1 ml) to give a colorless solution. Lithium hydroxide (11.19 mg, 458 μmol) in solution in water (458 μl) was added to the reaction mixture in one go. The solution was stirred at RT for 30 min. The progression of the reaction was monitored by UPLC-MS (gradient I). After this period, the reaction was complete. The solution was directly purified by preparative HPLC (gradient J) and resulted in the compound 34 (35 mg, 71%) identified as the desired compound. HRMS (ESI+): calculated for $C_{57}H_{74}N_7O_{13}$ $[M+H]^+$, m/z 1064.5339, found 1064.5341. UPLC-MS (gradient I) Rt=3.82 min.

Compound 35a

In a 50 ml round-bottom flask the compound 34 (35.0 mg, 33 μmol) was dissolved in a mixture of DMSO (1 ml) and MeCN (4 ml) to give a colorless solution. DIPEA (34 μl, 197 μmol), taurine (12.47 mg, 99 μmol) and HATU (25.8 mg, 65.8 μmol) were added to the reaction mixture in one go. The solution was stirred at RT for 2 h. The progression of the reaction was monitored by UPLC-MS (gradient I). After this period, the reaction was complete. The solution was directly purified by preparative HPLC (gradient K) and resulted in the compound 35a (31.7 mg, 75%) identified as the desired compound. HRMS (ESI+): calculated for $C_{61}H_{85}N_9O_{17}S_2$ $[M+2H]^{2+}$, m/z 639.7747, found 639.7747. UPLC-MS (gradient I) Rt=3.36 min.

Compound 35b 3-((2-Aminoethyl)dimethylammonio)propane-1-sulfonate was prepared according to the procedure described in WO 2011/146595 and in Organic & Biomolecular Chemistry 2012, 10, 1883. In a 5 ml round-bottom flask the 3-((2-aminoethyl)dimethylammonio)propane-1-sulfonate (10.56 mg, 50.0 μmol) and the compound 34 (10.64 mg, 10 μmol) were dissolved in DMSO (600 μl) to give a yellow solution. DIPEA (12.06 μl, 70.0 μmol) and HATU (15.21 mg, 40.0 μmol) were added to the reaction mixture in one go. The solution was stirred at RT for 15 min. The progression of the reaction was monitored by UPLC-MS (gradient I). After this period, the reaction was complete. The solution was directly purified by preparative HPLC (gradient L) and resulted in the compound 35b (8.6 mg, 59%) identified as the desired compound. HRMS (ESI+): calculated for $C_{71}H_{107}N_{11}O_{17}S_2$ $[M+2H]^{2+}$, m/z 724.8638, found 724.8644. UPLC-MS (gradient I) Rt=3.24 min.

Compound 35c: this compound was prepared according to the same procedure as that used for the synthesis of 35a and 35b.

Compound 35d

2-Trimethylammoniumethylamine hydrochloride was prepared according to the procedure described in Analytical Chemistry 2014, 86, 10006. In a 5 ml round-bottom flask the 2-trimethylammoniumethylamine hydrochloride (6.98 mg, 50.0 μmol) and the compound 34 (10.64 mg, 10 μmol) were dissolved in DMSO (600 μl) to give a yellow solution. DIPEA (16.68 μl, 100 μmol) and HATU (15.21 mg, 40.0 μmol) were added to the reaction mixture in one go. The solution was stirred at RT for 15 min. The progression of the reaction was monitored by UPLC-MS (gradient I). After this period, the reaction was complete. The solution was directly purified by preparative HPLC (gradient L) and resulted in the compound 35d (6.8 mg, 55%) identified as the desired compound. HRMS (ESI+): calculated for $C_{67}H_{99}N_{11}O_{11}$ $[M+2H]^{2+}$, m/z 616.8757, found 616.8759. UPLC-MS (gradient I) Rt=2.97 min.

Complex C4a

In a 50 ml round-bottom flask the compound 35a (31.7 mg, 25 μmol) was dissolved in TFA (200 μl) to give a yellow solution. The solution was stirred at RT for 30 min. The progression of the deprotection was monitored by UPLC-MS (gradient I). After this period, the deprotection was complete. The TFA was evaporated under reduced pressure. The residue was dissolved in water (6 ml) and MeCN (1 ml), adjusting the pH to 7 with a 3 M sodium hydroxide solution. Europium(III) hexahydrate chloride (36.3 mg, 99 μmol) was added to the reaction mixture, with stirring, in one go. The pH was adjusted to 7 by addition of 3 M sodium hydroxide. The solution was stirred at RT for 5 d. The progression of the reaction was monitored by UPLC-MS (gradient I). After this period, the reaction was complete. The solution was directly purified by preparative HPLC (gradient M) and resulted in the complex C4a (15.6 mg, 55%) identified as the desired compound. HRMS (ESI+): calculated for $C_{44}H_{50}N_9O_{15}S_2Eu$ $[M+2H]^{2+}$, m/z 579.6028, found 579.6026. UPLC-MS (gradient N), isomer 1 Rt=1.32 min and isomer 2 Rt=1.64 min.

Complex C5a: this complex was prepared according to the same procedure as that used for the synthesis of C4a.

Complex C4b

In a 25 ml round-bottom flask the compound 35b (8.6 mg, 5.93 μmol) was dissolved in TFA (130 μl) to give a yellow solution. The solution was stirred at RT for 30 min. The progression of the deprotection was monitored by UPLC-MS (gradient I). After this period, the deprotection was complete. The TFA was evaporated under reduced pressure. The residue was dissolved in 50 mM pH 7.4 HEPES buffer (2 ml). Europium(III) hexahydrate chloride (13.03 mg, 36 μmol) was added to the reaction mixture, with stirring, in one go. The solution was stirred at RT for 40 h. The progression of the reaction was monitored by UPLC-MS (gradient I). After this period, the reaction was complete. The solution was directly purified by preparative HPLC (gradient M) and resulted in the complex C4b (6.5 mg, 83%) identified as the desired compound. HRMS (ESI+): calculated for $C_{54}H_{73}N_{11}O_{15}S_2Eu$ $[M+3H]^{3+}$, m/z 444.1310, found 444.1309. UPLC-MS (gradient ORt=0.34 min.

Complex C5b: this complex was prepared according to the same procedure as that used for the synthesis of C4b.

Complex C4c: this complex was prepared according to the same procedure as that used for the synthesis of C4b.

Complex C5c: this complex was prepared according to the same procedure as that used for the synthesis of C4b.

Complex C4d

In a 25 ml round-bottom flask the compound 35d (6.8 mg, 5.51 µmol) was dissolved in TFA (200 µl) to give a yellow solution. The solution was stirred at RT for 5 h. The progression of the deprotection was monitored by UPLC-MS (gradient I). After this period, the deprotection was complete. The TFA was evaporated under reduced pressure. The residue was dissolved in 50 mM pH 7.4 HEPES buffer (2 ml). Europium(III) hexahydrate chloride (12.09 mg, 33 µmol) was added to the reaction mixture, with stirring, in one go. The solution was stirred at RT for 18 h. The progression of the reaction was monitored by UPLC-MS (gradient I). After this period, the reaction was complete. The solution was directly purified by preparative HPLC (gradient M) and resulted in the complex C4d (3 mg, 19%) identified as the desired compound. HRMS (ESI+): calculated for $C_{50}H_{64}N_{11}O_9Eu$ $[M+2H]^{2+}$, m/z 557.7048, found 557.7050. UPLC-MS (gradient I) Rt=0.32 min.

Complex C5d: this complex was prepared according to the same procedure as that used for the synthesis of C4b.

Complex C4e: this complex was prepared according to the same procedure as that used for the synthesis of C4b.

Complex C5e: this complex was prepared according to the same procedure as that used for the synthesis of C4b.

Compound 37

The compound 37 was prepared according to the procedure described in the article Chemistry—A European Journal 2008, 14, 1726. The chelidamic acid monohydrate 5 (3 g, 15 mmol) was heated at reflux in EtOH (60 ml) in the presence of 97% sulfuric acid (0.6 ml) for 16 h. The solvent was evaporated under reduced pressure, the white residue remaining was neutralized with a saturated aqueous solution of sodium bicarbonate and extracted with DCM. The organic phase was dried with magnesium sulfate, evaporated to dryness and the diester 37 was obtained in the form of a white solid (2.27 g, 63%). $R_f$=0.10 (silica, $CH_2Cl_2$/MeOH 99/1); $^1H$ NMR ($CDCl_3$, 300 MHz) δ 7.31 (s, 2H), 4.46 (q, J=7.1 Hz, 4H), 1.42 (t, J=7.1 Hz, 6H); $^{13}C$ NMR (DMSO-$d_6$, 62.5 MHz) δ 166.0, 164.3, 149.9, 115.2, 61.4, 14.1.

Compound 38

The compound 38 was prepared according to the procedure described in the article Organic & Biomolecular Chemistry 2012, 10, 9183. Triphenylphosphine (1.13 g, 4.31 mmol) and tert-butyl-(3-hydroxypropyl) carbamate (0.77 g, 4.41 mmol) diluted in anhydrous THF (10 ml) were added under argon to a solution of diethyl chelidamate 37 (0.5 g, 2.09 mmol) in anhydrous THF (50 ml). DIAD (0.83 ml, 4.19 mmol) was then added dropwise over 10 min and the reaction medium was stirred at 70° C. for 16 h. The medium was evaporated under reduced pressure and the yellow viscous residue obtained was purified by flash silica column chromatography (AcOEt/EP 50/50). The compound 38 was obtained in the form of a white powder (0.82 g, 99%), $R_f$=0.23 (silica, AcOEt/EP 50/50); $^1H$ NMR ($CDCl_3$, 300 MHz) δ 7.77 (s, 2H), 4.68 (s, 1H), 4.47 (q, J=7.1 Hz, 4H), 4.19 (t, J=5.9 Hz, 2H), 3.39-3.28 (m, 2H), 2.10-1.99 (m, 2H), 1.45 (t, J=7.1 Hz, 6H), 1.43 (s, 9H); $^{13}C$ NMR ($CDCl_3$, 75 MHz) δ 166.8, 164.7, 156.0, 150.2, 114.3, 79.4, 66.6, 62.4, 37.5, 29.4, 28.4, 14.2.

Compound 39

The compound 39 was prepared according to the procedure described in the article Organic & Biomolecular Chemistry 2012, 10, 9183. Sodium borohydride (817 mg, 21.595 mmol) was added in small portions to a solution of compound 38 (1.70 g, 4.30 mmol) in EtOH (85 ml). The reaction medium was heated at reflux for 2 h. The mixture was then cooled to RT and 70 ml of water were added and the ethanol was removed under reduced pressure. The aqueous phase was extracted with DCM (4×20 ml). The organic phase was washed with a saturated solution of ammonium chloride (20 ml) then with water (20 ml), dried over magnesium sulfate, and evaporated under reduced pressure. The compound 39 was then obtained in the form of a white solid (1.02 g, 76%). $R_f$=0.30 (silica, $CH_2Cl_2$/MeOH 90/10); $^1H$ NMR ($CDCl_3$, 300 MHz) δ 6.72 (s, 2H), 4.71 (s, 4H), 4.68 (s, 1H), 4.09 (t, J=6.1 Hz, 2H), 3.37-3.23 (m, 2H), 2.77 (s, 2H), 2.07-1.93 (m, 2H), 1.43 (s, 9H); $^{13}C$ NMR ($CDCl_3$, 75 MHz) δ 166.5, 161.2, 156.3, 105.6, 79.4, 65.7, 64.4, 37.6, 29.4, 28.5.

Compound 40

The compound 40 was prepared according to the procedure described in the article Organic & Biomolecular Chemistry 2012, 10, 9183. Sodium hydroxide (338 mg, 8.45 mmol) and a solution of TsCl (1.07 g, 5.64 mmol) in THF (23 ml) were added with stirring to a solution of the compound 39 (440 mg, 1.41 mmol) in a THF/water (1:1.17 ml) mixture at 0° C. The reaction mixture was stirred at RT for 16 h, then decanted, and the aqueous phase was washed with DCM (10 ml). The collected organic phases were washed with an aqueous solution of 5% sodium bicarbonate (10 ml), dried over magnesium sulfate, filtered and evaporated to dryness. The compound 40 was obtained in the form of a white powder (841 mg, 96%). $R_f$=0.40 (silica, $CH_2Cl_2$/MeOH 98/2); $^1H$ NMR ($CDCl_3$, 300 MHz) δ 7.80 (d, J=8.0 Hz, 4H), 7.33 (d, J=8.0 Hz, 4H), 6.81 (s, 2H), 4.98 (s, 4H), 4.68 (s, 1H), 4.03 (t, J=6.0 Hz, 2H), 3.36-3.23 (m, 2H), 2.44 (s, 6H), 2.06-1.91 (m, 2H), 1.45 (s, 9H); $^{13}C$ NMR ($CDCl_3$, 75 MHz) δ 166.7, 156.1, 153.3, 145.3, 132.8, 130.1, 128.2, 107.7, 79.6, 71.3, 66.1, 37.6, 29.4, 28.5, 21.8.

Compound 41

Cesium carbonate (1.01 g, 3.12 mmol) and the compound 40 (844 mg, 1.36 mmol) were added under argon to a solution of the compound 19 (943 mg, 2.98 mmol) in anhydrous DMF (26 ml). The reaction mixture was stirred at RT for 40 h, filtered, evaporated to dryness and the crude product obtained was purified by silica column chromatography (100% $CH_2Cl_2$ then 90/10 $CH_2Cl_2$/AcOEt) to yield the compound 41 in the form of white powder (980 mg, 79%). $R_f$=0.58 (silica, $CH_2Cl_2$/AcOEt 90/10); $^1H$ NMR ($CDCl_3$, 300 MHz) δ 8.11-8.04 (m, 2H), 7.72-7.60 (m, 6H), 6.76 (s, 2H), 4.70 (s, 1H), 4.60 (s, 4H), 4.12 (s, 4H), 4.02-3.92 (m, 2H), 3.35-3.21 (m, 2H), 2.03-1.87 (m, 2H), 1.45 (s, 9H), 1.35 (s, 18H); $^{13}C$ NMR ($CDCl_3$, 75 MHz) δ 167.4, 166.6, 157.2, 155.9, 147.9, 133.58, 133.55, 131.8, 130.9, 124.1, 107.6, 82.3, 79.4, 65.7, 53.2, 49.1, 37.5, 29.2, 28.4, 27.8; LRMS (ESI+): calculated for $C_{39}H_{53}N_6O_{15}S_2$ $[M+H]^+$, m/z 909.30, found 909.30.

Compound 42

2-Mercaptoethanol (949 µl, 13.574 mmol) and 1,8-diazabicyclo[5.4.0]undec-7-ene (828 µl, 5.55 mmol) were added with stirring to a solution of di-nosylated compound 41 (1.12 g, 1.23 mmol) in MeCN (54 ml). The mixture was stirred for 30 min at RT. The solvent was removed under reduced pressure then DCM (20 ml) was added and the mixture was washed with water (2×10 ml), dried over magnesium sulfate, filtered and evaporated under reduced pressure. The crude product obtained was purified by silica column chromatography (95/5 then 90/10 AcOEt/MeOH) to yield the compound 42 in the form of a yellow solid (523 mg, 79%). $R_f$=0.24 (silica, AcOEt/MeOH 90/10); $^1H$ NMR ($CDCl_3$, 300 MHz) δ 6.73 (s, 2H), 4.79-4-75 (m, 1H), 4.04 (t, J=6 Hz, 2H), 3.84 (s, 4H), 3.73 (s, 2H), 3.34 (s, 4H), 3.31-3.25 (m, 2H), 2.00-1.92 (m, 2H), 1.44 (s, 18H), 1.42 (s, 9H); $^{13}C$ NMR ($CDCl_3$, 75 MHz) δ 171.4, 166.1, 160.5, 156.0, 106.7, 81.2, 79.3, 65.5, 54.5, 51.2, 37.6, 29.3, 28.4, 28.1; MS (ESI+) calculated for $C_{27}H_{47}N_4O_7$ [M+H]+, m/z 539.3445, found 539.3445.

Compound 43

The compound 42 (480 mg, 0.893 mmol), sodium carbonate (947 mg, 8.93 mmol) and sodium iodide (13 mg, 0.0893 mmol) were added under argon to a solution of compound 12 (945 mg, 0.893 mmol) in MeCN (447 ml). The suspension was stirred at reflux for 65 h. The residue was filtered, evaporated under reduced pressure and purified by alumina column chromatography (100% DCM up to 95/5 DCM/MeOH in increments of 1%). The fractions recovered, corresponding to a mixture of compound in free form and in the form of a sodium complex, were then redissolved in a minimum amount of DCM and washed several times with water. The desired compound 43 was obtained in the form of a yellow powder (690 mg, 62%). $R_f$=0.33 (alumina, DCM/MeOH 97/3); $^1$H NMR (CDCl$_3$, 300 MHz) δ 7.40 (d, J=8.8 Hz, 4H), 7.24 (d, J=1.5 Hz, 2H), 7.20 (d, J=1.5 Hz, 2H), 6.79 (d, J=8.8 Hz, 4H), 6.64 (s, 2H), 4.71 (s, 1H), 4.64 (s, 4H), 4.01-3.96 (m, 2H), 3.86-3.83 (m, 12H), 3.81 (s, 6H), 3.39 (s, 6H), 3.17-3.08 (m, 2H), 1.82-1.70 (m, 2H), 1.48 (s, 9H), 1.46 (s, 18H), 1.41 (s, 9H); $^{13}$C NMR (CDCl$_3$, 75 MHz) δ 170.5, 168.9, 166.2, 158.5, 158.1, 155.9, 133.4, 131.7, 123.2, 122.9, 115.6, 114.7, 107.9, 92.6, 86.6, 81.2, 81.1, 79.0, 65.8, 65.1, 60.1, 59.8, 59.6, 58.31, 58.28, 52.3, 37.5, 29.6, 28.4, 28.2. MS (ESI+): m/z 626.8 [M+2H]$^{2+}$, 42%, 645.8 [M+K+H]$^{2+}$, 100%), 1252.6 ([M+H]+, 15%); HRMS (ESI+) calculated for $C_{69}H_{86}N_7O_{15}$ [M+H]+, m/z 1252.6182, found 1252.6194; IR (cm$^{-1}$): ν 3425, 2976, 2931, 2210, 1758, 1733, 1596, 1510, 1367, 1213, 1158.

Compound 44

In a 5 ml round-bottom flask the compound 43 (27.0 mg, 22 μmol) was dissolved in MeCN (1 ml) to give a colorless solution. Lithium hydroxide (2.66 mg, 109 μmol) in solution in water (500 μl) was added to the reaction mixture in one go. The solution was stirred at RT for 30 min. The progression of the reaction was monitored by UPLC-MS (gradient I). After this period, the reaction was complete. The solution was directly purified by preparative HPLC (gradient O) and resulted in the compound 44 (22.9 mg, 86%) identified as the desired compound. HRMS (ESI+): calculated for $C_{67}H_{82}N_7O_{15}$ [M+H]+, m/z 1224.5863, found 1224.5867. UPLC-MS (gradient I) Rt=3.87 min.

Compound 45a

In a 25 ml round-bottom flask the compound 44 (22.90 mg, 19 μmol) was dissolved in DMSO (1 ml) to give a colorless solution. Taurine (11.82 mg, 94 μmol), DIPEA (22 μl, 131 μmol) and then HATU (29.3 mg, 74.8 μmol) were added to the reaction mixture in one go. The solution was stirred at RT for 2 h. The progression of the reaction was monitored by UPLC-MS (gradient I). After this period, the reaction was complete. The solution was directly purified by preparative HPLC (gradient K) and resulted in the compound 26a (27 mg, 70%) identified as the desired compound. HRMS (ESI+): calculated for $C_{71}H_{93}N_9O_{19}S_2$ [M+2H]$^{2+}$, m/z 719.8009, found 719.8011. UPLC-MS (gradient I) Rt=3.22 min.

Compound 45b: this compound was prepared according to the same procedure as that used for the synthesis of 45a by selecting the corresponding amine.

Compound 45c: this compound was prepared according to the same procedure as that used for the synthesis of 45a by selecting the corresponding amine.

Compound 45c: this compound was prepared according to the same procedure as that used for the synthesis of 45a by selecting the corresponding amine.

Compound 45d: this compound was prepared according to the same procedure as that used for the synthesis of 45a by selecting the corresponding amine.

Complex C6a:

In a 10 ml round-bottom flask the compound 45a (18.9 mg, 13 μmol) was dissolved in TFA (200 μL) to give a yellow solution. The solution was stirred at RT for 30 min. The progression of the deprotection was monitored by UPLC-MS (gradient I). After this period, the deprotection was complete. The TFA was removed under reduced pressure. The residue was dissolved in 50 mM pH 7.4 HEPES buffer (6.2 ml). Europium(III) hexahydrate chloride (27.5 mg, 75 μmol) was added to the reaction mixture, with stirring, in one go. The solution was stirred at RT for 4 d. The progression of the reaction was monitored by UPLC-MS (gradient I). After this period, the reaction was complete. The solution was directly purified by preparative HPLC (gradient M) and resulted in the complex C6a (0.89 mg, 5%) identified as the desired compound. HRMS (ESI+): calculated for $C_{54}H_{58}N_9O_{17}S_2Eu$ [M+2H]$^{2+}$, m/z 660.6299, found 660.6299. UPLC-MS (gradient I), isomer 1 Rt=1.5 min and isomer 2 Rt=1.55 min.

Complex C7a: this complex was prepared according to the same procedure as that used for the synthesis of C6a.

Complex C7a: this complex was prepared according to the same procedure as that used for the synthesis of C6a.

Complex C6b: this complex was prepared according to the same procedure as that used for the synthesis of C6a.

Complex C7b: this complex was prepared according to the same procedure as that used for the synthesis of C6a.

Complex C6c: this complex was prepared according to the same procedure as that used for the synthesis of C6a.

Complex C6d: this complex was prepared according to the same procedure as that used for the synthesis of C6a.

Complex C7d: this complex was prepared according to the same procedure as that used for the synthesis of C6a.

Compound 46: commercially available.

Compound 47: the compound 47 was prepared according to the procedure described in Journal Organic Chemistry 1987, 52, 2029.

Compound 48: the compound 48 was prepared according to the procedure described in EP2216330.

Compound 49: the compound 49 was prepared according to the procedure described in EP2216330 for an analogous compound.

Compound 50: the compound 50 was prepared according to the procedure described in EP2216330 for an analogous compound.

Compound 51: this compound was prepared according to the same procedure as that used for the synthesis of 15.

Compound 52: the compound 52 was prepared according to the procedure described in Organic Letters 2014, 16, 1290.

Compound 53: this compound was prepared according to the same procedure as that used for the synthesis of 20.

Compound 54: this compound was prepared according to the same procedure as that used for the synthesis of 21.

Compound 55: this compound was prepared according to the same procedure as that used for the synthesis of 23.

Compound 56: this compound was prepared according to the same procedure as that used for the synthesis of 9.

Compound 57: this compound was prepared according to the same procedure as that used for the synthesis of 10.

Compound 58: this compound was prepared according to the same procedure as that used for the synthesis of 12.

Compound 59: this compound was prepared according to the same procedure as that used for the synthesis of 24.

Compound 60: this compound was prepared according to the same procedure as that used for the synthesis of 25.

Compound 61a-d: these compounds were prepared according to the same procedure as that used for the synthesis of 26a-d.

Complexes C8a-d: these complexes were prepared according to the same procedure as that used for the synthesis of C1a-d.

Complexes C9a-d: these complexes were prepared according to the same procedure as that used for the synthesis of C2a-d.

Complexes C10a-d: these complexes were prepared according to the same procedure as that used for the synthesis of C3a-d.

Photophysical Measurements

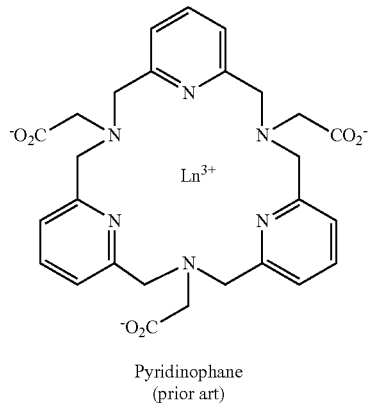

Pyridinophane
(prior art)

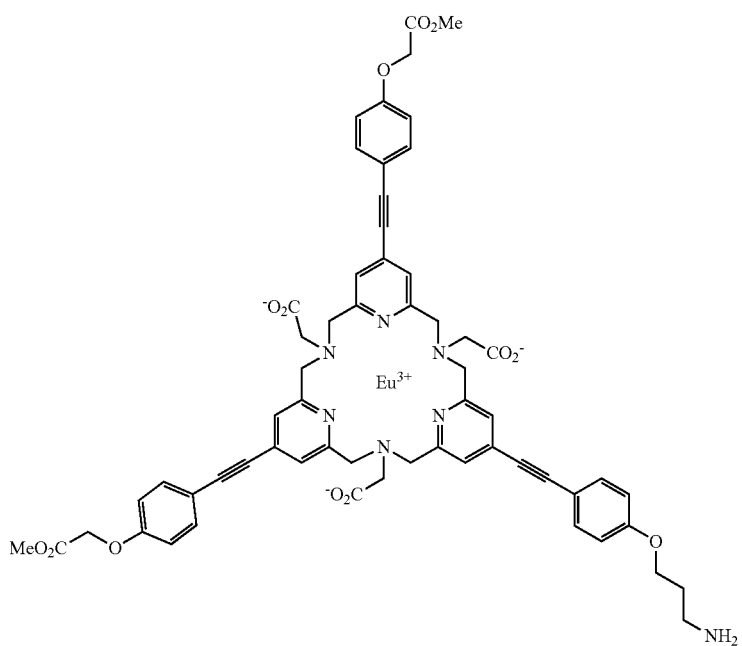

62

-continued

63

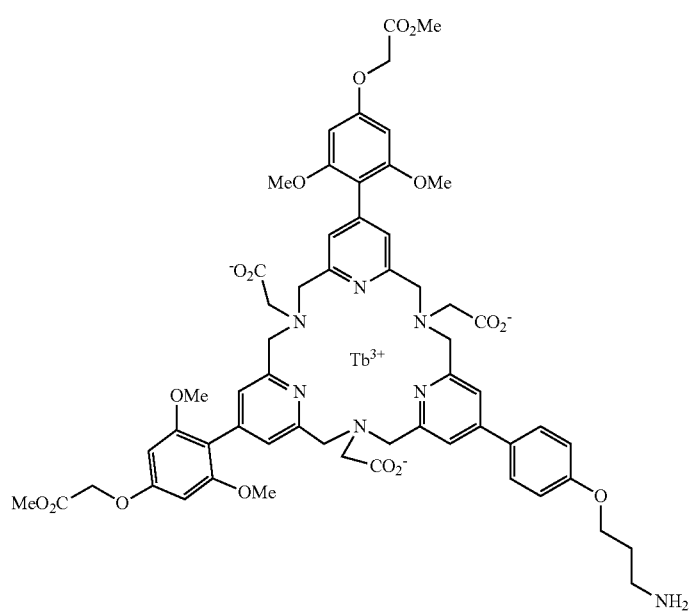

The photophysical properties of complexes representative of the invention have been reported in the table below.

TABLE 1

Photophysical properties of the complexes

| Complex | Lanthanide (Ln) | No. of Chrom[a] | Soluble group | Absorption λmax (nm) | Brightness ε × Φ (H$_2$O) | Lifetime τ$_{H_2O}$ (ms) | Solubility in H$_2$O |
|---|---|---|---|---|---|---|---|
| Pyridinophane | Eu | 0 | — | 267 | 564 | 0.78 | yes |
| 62 | Eu | 3 | — | 320 | — | — | no |
| 63 | Tb | 3 | — | 328 | — | — | no |
| C1a | Eu | 3 | Sulfo | 320 | 5100 | 0.74 | yes |
| C1b | Eu | 3 | Sulfobetaine | 320 | 6000 | 0.68 | yes |
| C1c | Eu | 3 | Sugar | 318 | 6000 | 0.70 | yes |
| C4a | Eu | 1 | Sulfo | 320 | 1400 | 0.69 | yes |
| C4b | Eu | 1 | Sulfobetaine | 321 | 1400 | 0.73 | yes |
| C4d | Eu | 1 | Ammonium | 320 | 1400 | 0.76 | yes |

[a]Chrom = chromophore

The base pyridinophane (prior art) is soluble in water (biological and buffer media) but the chromophore (pyridine) is not suitable for an excitation between 310-350 nm (excitation by flash lamp or nitrogen laser) since the maximum absorption of this complex is 267 nm. The introduction of the chromophores to these pyridinophane systems without a solubilizing group (compound 62, 63) makes these complexes compatible with the laser or flash excitation sources (absorption 62 and 63 around 320-330 nm) but these complexes are insoluble in water (biological and buffer media). This lack of solubility prohibits any use of 62 and 63 in an HTRF-type immunoassay. On the other hand, as soon as solubilizing groups are introduced to 62 and 63 corresponding to the complexes of the invention (examples C1a-c or C4a-b, C4d) then these compounds become soluble in biological and buffer media and the complexes may be used in an HTRF-type immunoassay, in microscopy or other life science applications.

Figure 2:
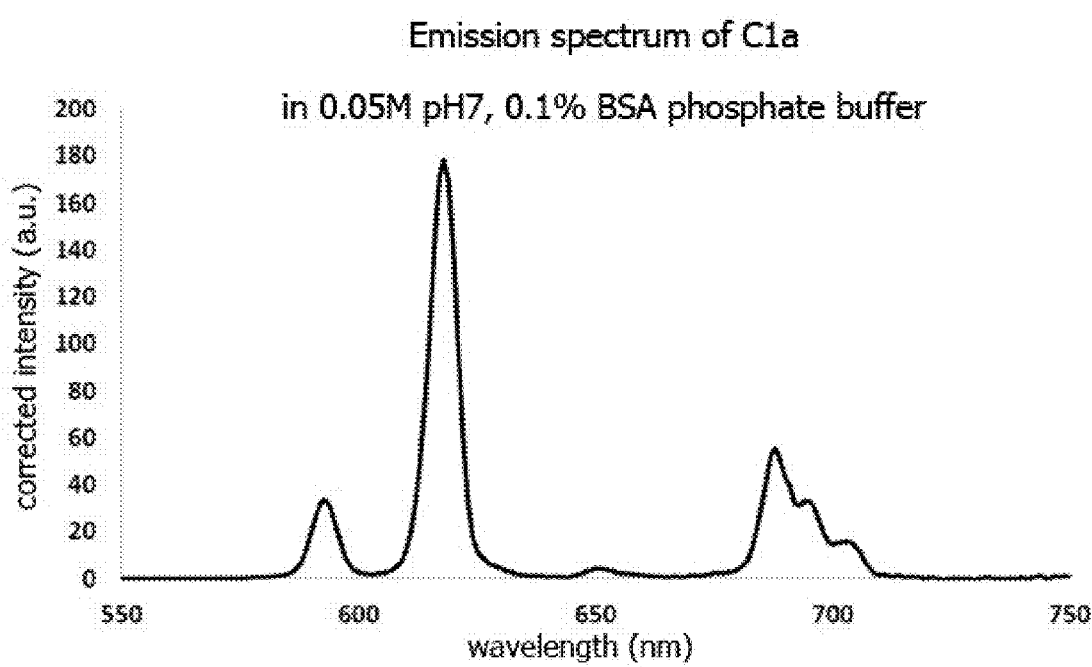
FIG. 2 shows the emission spectrum of a complex of the invention.

FIGS. 1 and 2 show the absorption and emission spectra of the complex C1a. The absorption spectrum has a maximum at 320 nm. Thus this complex series is perfectly compatible with laser and flash lamp excitation. The emission spectrum has a maximum at 620 nm which makes it possible to have an optimal overlap with a compatible acceptor.

The invention claimed is:

1. A complexing agent of formula (I):

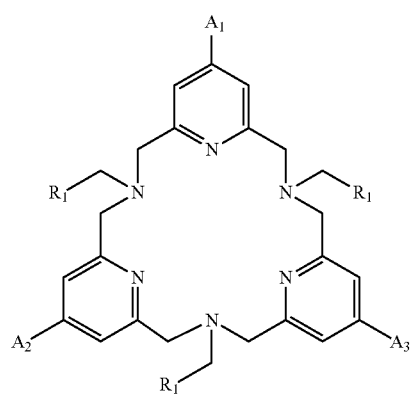

(I)

wherein:
the $R_1$ groups are identical and are either: —$CO_2H$, or —PO(OH)R, wherein R is selected from the group consisting of: phenyl optionally substituted by an —$SO_3H$ group benzyl, methyl, ethyl, propyl, n-butyl, sec-butyl, isobutyl, and tent-butyl;

the $A_1$, $A_2$ groups are identical or different and are selected from the group consisting of: a group of formula -$L_1$-E; a group of formula (II) and a group of formula (II');

the $A_3$ group is selected from the group consisting of: a group of formula —O-$L_3$-G, a group of formula (II), a group of formula (II'), a group of formula (III), and a group of formula (III');

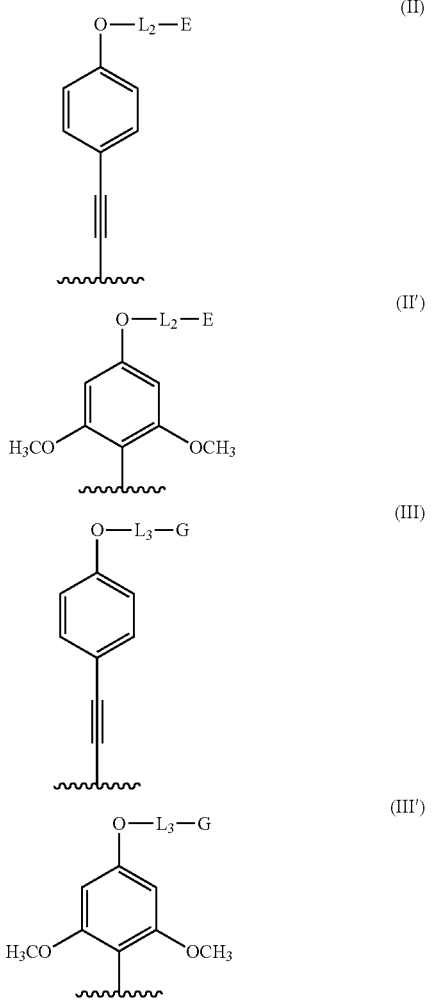

$L_1$, $L_2$ and $L_3$ are identical or different and each represent a divalent linkage group;

E is a group that renders the complexing agent water-soluble, chosen selected from the group consisting of: —$SO_3H$, —$PO(OH)_2$, —$CO_2H$, —$N^+Alk_1Alk_2Alk_3$, a carbohydrate residue, a sulfobetaine; and a PEG group;

G is a reactive group selected from the group consisting of: an acrylamide, an amine, an ester, an aldehyde, an alkyl halide, an anhydride, an aniline, an azide, an aziridine, a carboxylic acid, a diazoalkane, a haloacetamide, a halotriazine, dichlorotriazine, a hydrazine, an imido ester, an isocyanate, an isothiocyanate, a maleimide, a sulfonyl halide, a thiol, a ketone, an acid halide, a succinimidyl ester, a hydroxysuccinimidyl ester, a hydroxysulfosuccinimidyl ester, an azidonitrophenyl, an azidophenyl, a glyoxal, a triazine, and an acetylenic group;

$Alk_1$, $Alk_2$, $Alk_3$, which may be identical or different, each represent a ($C_1$-$C_6$)alkyl.

2. The complexing agent as claimed in claim 1, wherein $A_1$ and $A_2$ are identical and are a group of formula (II) and $A_3$ is a group of formula (III).

3. The complexing agent as claimed in claim 1, wherein $A_1$ is a group of formula (II), $A_2$ is an -$L_1$-E group and $A_3$ is a group of formula (III).

4. The complexing agent as claimed in claim 1, wherein $A_1$ and $A_2$ are identical and are groups of formula (II), and $A_3$ is a group of formula —O-$L_3$-G.

5. The complexing agent as claimed in claim 1, wherein $A_1$ and $A_2$ are identical and are groups of formula -$L_1$-E and $A_3$ is a group of formula (III).

6. The complexing agent as claimed in claim 1, wherein $A_1$ and $A_2$ are identical and are groups of formula (II') and $A_3$ is a group of formula (III').

7. The complexing agent as claimed in claim 1, wherein $A_1$ is a group of formula (II'), $A_2$ is an -$L_1$-E group and $A_3$ is a group of formula (III').

8. The complexing agent as claimed in claim 1, wherein $A_1$ and $A_2$ are identical and are groups of formula (II'), and $A_3$ is a group of formula —O-$L_3$-G.

9. The complexing agent as claimed in claim 1, wherein $A_1$ and $A_2$ are identical and are groups of formula -$L_1$-E and $A_3$ is a group of formula (III').

10. The complexing agent as claimed in claim 1, wherein $L_1$, $L_2$ and $L_3$ are selected from the group consisting of:

a linear or branched $C_1$-$C_{20}$ alkylene group optionally containing one or more double or triple bonds;

a $C_5$-$C_8$ cycloalkylene group, a $C_6$-$C_{14}$ arylene group, said alkylene, cycloalkylene or arylene groups optionally containing one or more hetero atoms, or one or more carbamoyl or carboxamido groups, and said alkylene, cycloalkylene or arylene groups being optionally substituted by $C_1$-$C_8$ alkyl, $C_6$-$C_{14}$ aryl, sulfonate or oxo groups; and a group having one of the following formulae:

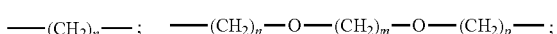
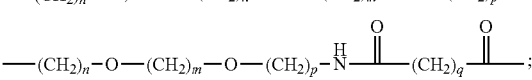
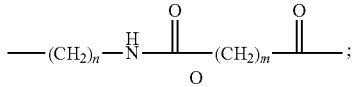
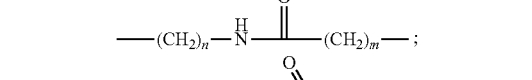
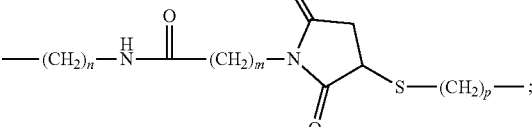

-continued

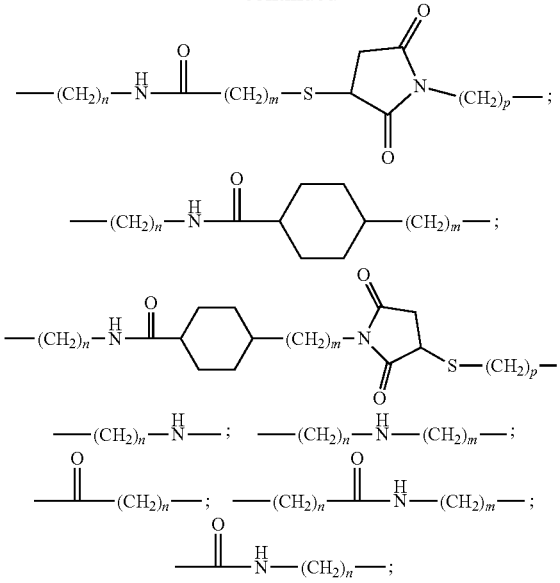

wherein n, m, p, q are integers from 1 to 5.

11. The complexing agent as claimed in claim 1, wherein the -$L_3$-G group consists of (i) a reactive group G selected from the group consisting of: a carboxylic acid, an amine, a succinimidyl ester, a haloacetamide, a hydrazine, an isothiocyanate, and a maleimide group, and (ii) a spacer arm $L_3$ consisting of an alkylene group comprising from 1 to 5 carbon atoms.

12. The complexing agent as claimed in claim 1, wherein $L_1$ is a divalent group of formula:

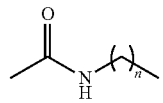

where n is an integer from 1 to 5.

13. The complexing agent as claimed in claim 1, wherein $L_2$ is a divalent group of formula:

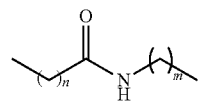

where n and m are integers from 1 to 5.

14. The complexing agent as claimed in claim 1, wherein $L_3$ is a divalent group of formula:

—$(CH_2)_n$— where n is an integer from 1 to 5.

15. A fluorescent lanthanide complex comprising a complexing agent as claimed in claim 1 and a lanthanide selected from the group consisting of: $Eu^{3+}$, $Sm^{3+}$, and $Tb^{3+}$.

16. A fluorescent lanthanide complex of formula (IV), (V), (VI) or (VII) below:

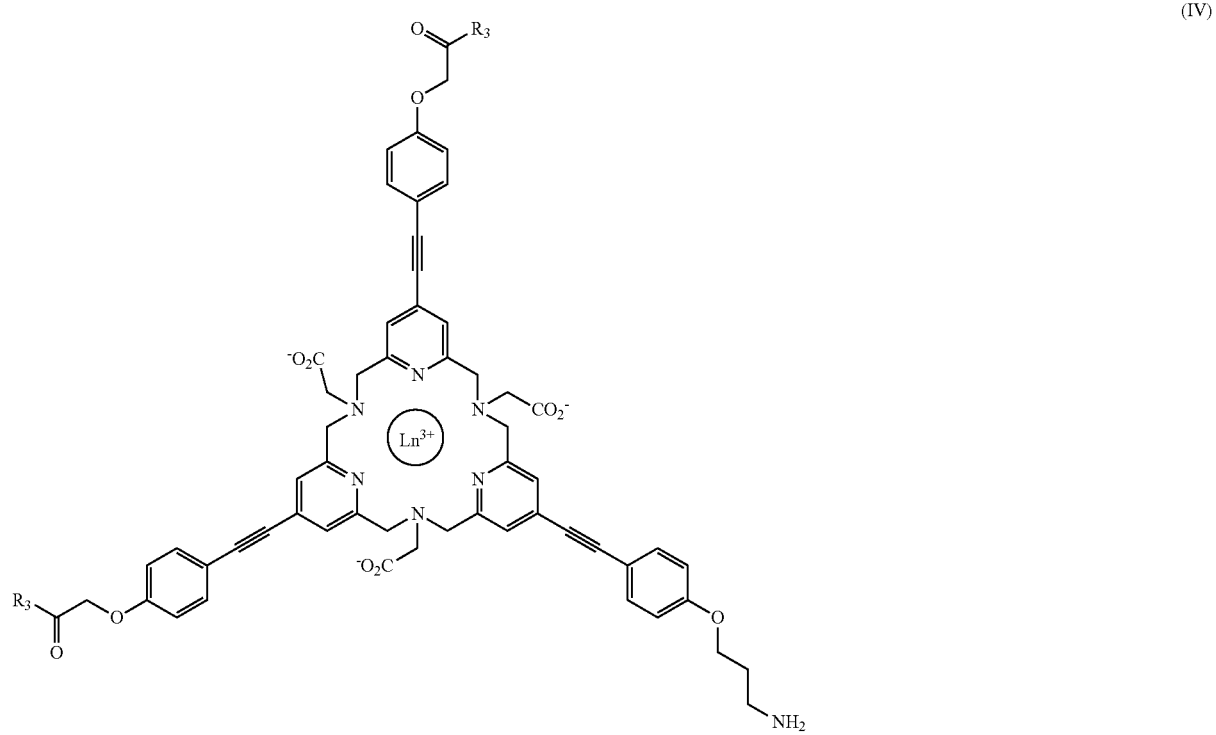

(IV)

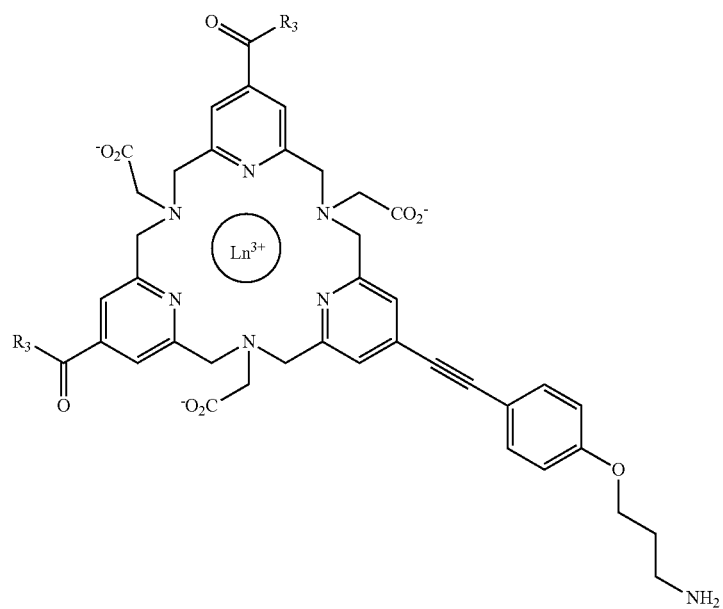
(V)
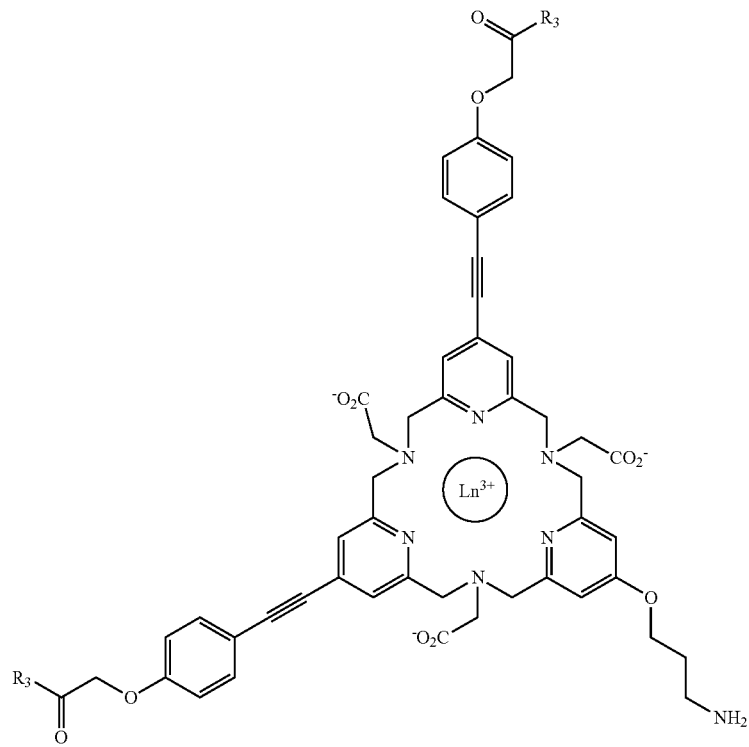
(VI)

(VII)

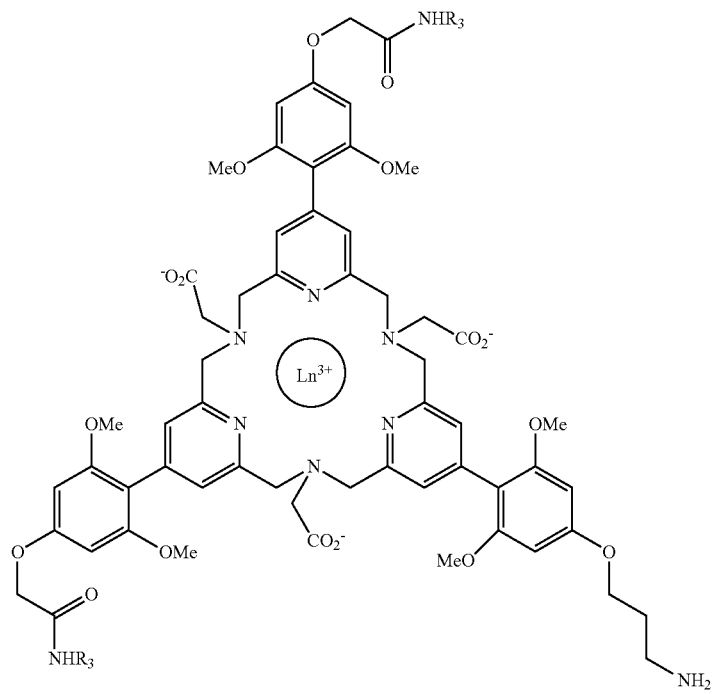

wherein:
$Ln^{3+}$ is chosen from: $Eu^{3+}$, $Tb^{3+}$, $Sm^{3+}$;
$R_3$ is chosen from the following groups: OH;

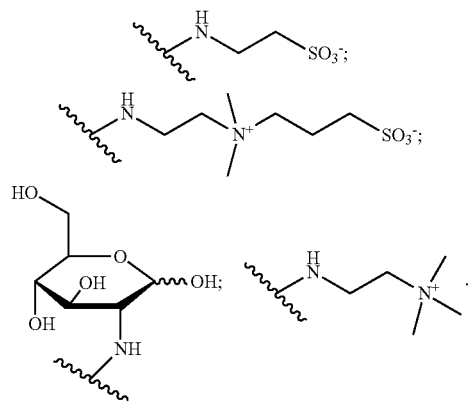

17. A fluorescent conjugate of a molecule of interest selected from the group consisting of: an amino acid, a peptide, a protein, an antibody, a sugar, a carbohydrate chain, a nucleoside, a nucleotide, an oligonucleotide, and an enzyme substrate, said molecule being covalently conjugated with a lanthanide complex as claimed in claim 15.

18. The complexing agent as claimed in claim 1, wherein the reactive group G is a group having one of the following formulae:

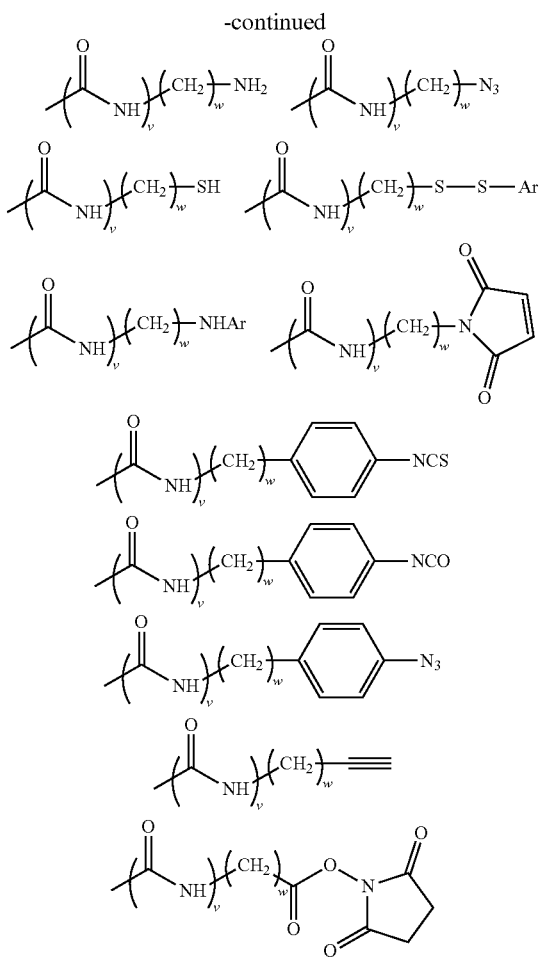

-continued

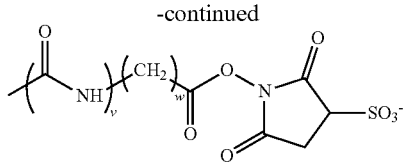
5

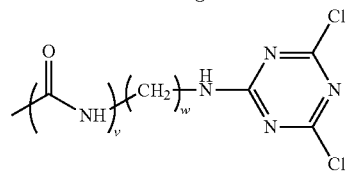
10 wherein w varies from 0 to 8 and v is equal to 0 or 1, and Ar is a saturated or unsaturated 5- or 6-membered heterocycle, comprising 1 to 3 heteroatoms, optionally substituted by a halogen atom.

19. The fluorescent conjugate of claim 17, wherein the molecule is the enzyme substrate and is selected from the group consisting of: a benzylguanine, a benzylcytosine, a chloroalkane and a coenzyme A.

* * * * *